(12) United States Patent
Wang et al.

(10) Patent No.: US 12,173,088 B2
(45) Date of Patent: Dec. 24, 2024

(54) ANTI-MICROBIAL PEPTIDES

(71) Applicant: BOARD OF REGENTS OF THE UNIVERSITY OF NEBRASKA, Lincoln, NE (US)

(72) Inventors: Guangshun Wang, Omaha, NE (US); Biswajit Mishra, Omaha, NE (US); Jayaram Lakshmaiah Narayana, Omaha, NE (US)

(73) Assignee: BOARD OF REGENTS OF THE UNIVERSITY OF NEBRASKA, Lincoln, NE (US)

(*) Notice: Subject to any disclaimer, the term of this patent is extended or adjusted under 35 U.S.C. 154(b) by 364 days.

(21) Appl. No.: 17/278,532

(22) PCT Filed: Jun. 28, 2019

(86) PCT No.: PCT/US2019/039792
§ 371 (c)(1),
(2) Date: Mar. 22, 2021

(87) PCT Pub. No.: WO2020/076381
PCT Pub. Date: Apr. 16, 2020

(65) Prior Publication Data
US 2022/0033437 A1    Feb. 3, 2022

Related U.S. Application Data

(60) Provisional application No. 62/743,695, filed on Oct. 10, 2018, provisional application No. 62/862,203, filed on Jun. 17, 2019.

(51) Int. Cl.
| | | |
|---|---|---|
| *C07K 7/06* | (2006.01) | |
| *A61K 38/00* | (2006.01) | |
| *A61K 45/06* | (2006.01) | |
| *A61L 27/54* | (2006.01) | |
| *A61L 29/16* | (2006.01) | |
| *A61L 31/16* | (2006.01) | |
| *C07K 7/08* | (2006.01) | |

(52) U.S. Cl.
CPC .............. *C07K 7/06* (2013.01); *A61K 45/06* (2013.01); *C07K 7/08* (2013.01); *A61K 38/00* (2013.01); *A61L 27/54* (2013.01); *A61L 29/16* (2013.01); *A61L 31/16* (2013.01); *A61L 2300/25* (2013.01); *A61L 2300/406* (2013.01)

(58) Field of Classification Search
CPC .......... A61K 38/00; A61K 45/06; C07K 7/06; C07K 7/08; A61L 27/54; A61L 29/16; A61L 31/16; A61L 2300/25; A61L 2300/406
See application file for complete search history.

(56) References Cited

U.S. PATENT DOCUMENTS

| | | |
|---|---|---|
| 7,465,784 B2 | 12/2008 | Wang |
| 7,985,836 B2 | 7/2011 | Wang |
| 8,722,616 B2 | 5/2014 | Wang |
| 9,580,472 B2 | 2/2017 | Wang |
| 9,707,282 B2 * | 7/2017 | Hancock ............... C07K 7/06 |
| 10,144,767 B2 | 12/2018 | Wang |
| 10,723,764 B2 | 7/2020 | Wang |
| 2009/0298707 A1 * | 12/2009 | Yarbrough ........... C07K 1/1077 506/14 |
| 2015/0315240 A1 | 11/2015 | Hancock et al. |
| 2016/0289272 A1 | 10/2016 | Otterlei et al. |

OTHER PUBLICATIONS

Oxidase ustYa [Colletotrichum higginsianum]—Protein—NCBI, Examiner generated pdf. https://www.ncbi.nlm.nih.gov/protein/TIC91808.1 (Year: 2020).*

Dathe et al., Cyclization Increases the Antimicrobial Activity and Selectivity of Arginine- and Tryptophan-Containing Hexapeptides t, Biochemistry 2004, 43, 9140-9150 (Year: 2004).*

Mishra, et al., "Low cationicity is important for systemic in vivo efficacy of database-derived peptides against drug-resistant Gram-positive pathogens" Proc. Natl. Acad. Sci. (2019) 116(27):13517-13522.

Bozelli, et al., "Membrane activity of two short Trp-rich amphipathic peptides" Biochim. Biophys. Acta Biomembr. (2020) 1862(7):183280.

Wang, et al., "Design of Antimicrobial Peptides: Progress Made with Human Cathelicidin LL-37" Adv. Exp. Med. Biol. (2019) 1117:215-240.

Narayana, et al., "Two distinct amphipathic peptide antibiotics with systemic efficacy" Proc. Natl. Acad. Sci. (2020) 117(32):19446-19454.

Wang, et al., "APD3: the antimicrobial peptide database as a tool for research and education" Nucleic Acids Res. (2016) 44(D1):D1087-93.

Mishra, et al., "Host defense antimicrobial peptides as antibiotics: design and application strategies" Curr. Opin. Chem. Biol. (2017) 38:87-96.

Mishra, et al., "Ab initio design of potent anti-MRSA peptides based on database filtering technology" J. Am. Chem. Soc. (2012) 134(30):12426-9.

Wang, et al., "APD2: the updated antimicrobial peptide database and its application in peptide design" Nucleic Acids Res. (2009) 37(Database issue):D933-7.

Wang, et al., "APD: the Antimicrobial Peptide Database" Nucleic Acids Res. (2004) 32(Database issue):D590-2.

Mishra, et al., "Design and surface immobilization of short anti-biofilm peptides" Acta Biomater. (2017) 49:316-328.

(Continued)

*Primary Examiner* — Lianko G Garyu
*Assistant Examiner* — John Cronin
(74) *Attorney, Agent, or Firm* — Robert C. Netter, Jr.; Dann, Dorfman, Herrell & Skillman

(57) ABSTRACT

Antimicrobial peptides and methods of use are provided.

33 Claims, 26 Drawing Sheets
Specification includes a Sequence Listing.

(56) References Cited

OTHER PUBLICATIONS

Wang, et al., "Transformation of human cathelicidin LL-37 into selective, stable, and potent antimicrobial compounds" ACS Chem. Biol. (2014) 9(9):1997-2002.

Wang, et al., "Correlation of three-dimensional structures with the antibacterial activity of a group of peptides designed based on a nontoxic bacterial membrane anchor" J. Biol. Chem. (2005) 280(7):5803-11.

Zarena, et al., "The π Configuration of the WWW Motif of a Short Trp-Rich Peptide Is Critical for Targeting Bacterial Membranes, Disrupting Preformed Biofilms, and Killing Methicillin-Resistant Staphylococcus aureus" Biochemistry (2017) 56(31):4039-4043.

Wang, et al., "High-quality 3D structures shine light on antibacterial, anti-biofilm and antiviral activities of human cathelicidin LL-37 and its fragments" Biochim. Biophys. Acta (2014) 1838(9):2160-72.

Wang, et al., "Amino Acid Composition Determines Peptide Activity Spectrum and Hot-Spot-Based Design of Merecidin" Adv. Biosyst. (2018) 2(5):1700259.

Mishra, et al.., "Antibacterial, antifungal, anticancer activities and structural bioinformatics analysis of six naturally occurring temporins" Peptides (2018) 106:9-20.

Narayana, et al., "Modulation of antimicrobial potency of human cathelicidin peptides against the ESKAPE pathogens and in vivo efficacy in a murine catheter-associated biofilm model" Biochim. Biophys. Acta Biomembr. (2019) 1861(9):1592-1602.

\* cited by examiner

FIG. 1A
| Designer peptides | | Lysine | In vivo efficacy |
|---|---|---|---|
| DFT565 | KLKLLLKLGLKLL | 4K | |
| DFT564 | GLKLLLKLGLKLL | 3K | |
| DFT561 | GLKLLLSLGLKLL | 2K | |
| DFT503 | GLSLLLSLGLKLL | 1K | |
| DFTamP1 | GLLSLLSLLGKLL | 1K | |
FIG. 1B
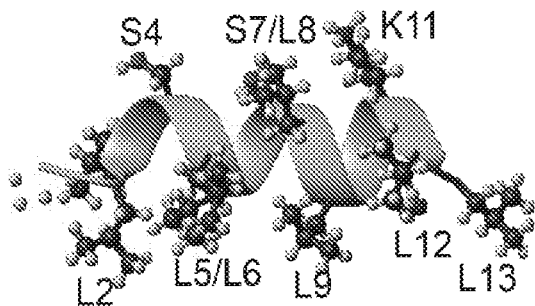
FIG. 1C
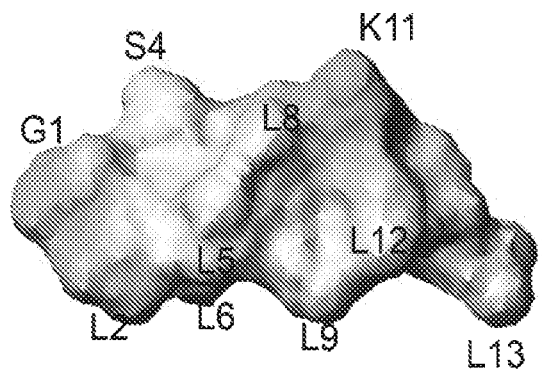
FIG. 1D
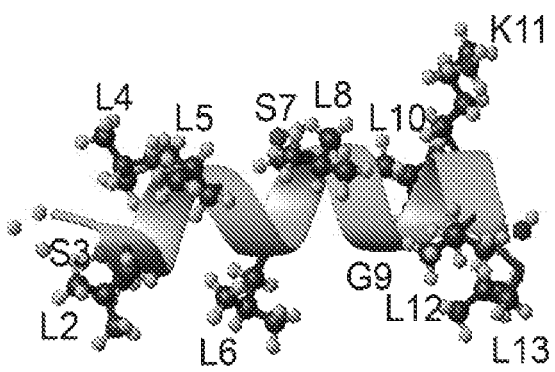
FIG. 1E
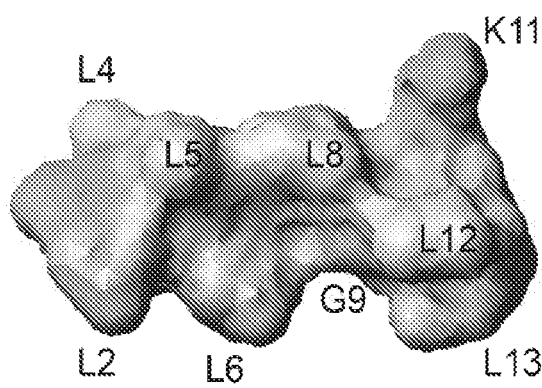
FIG. 1F

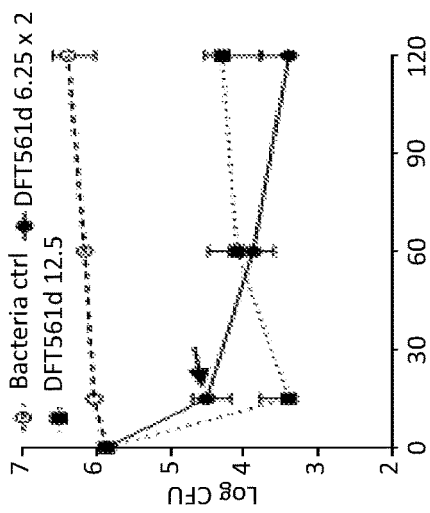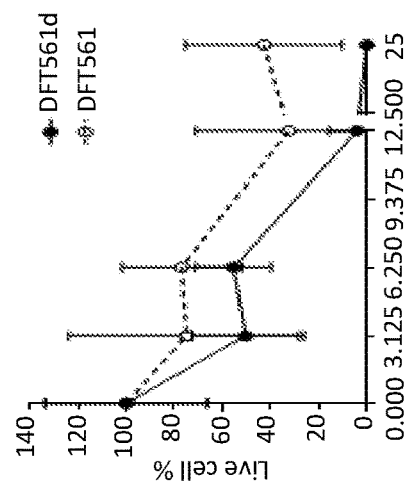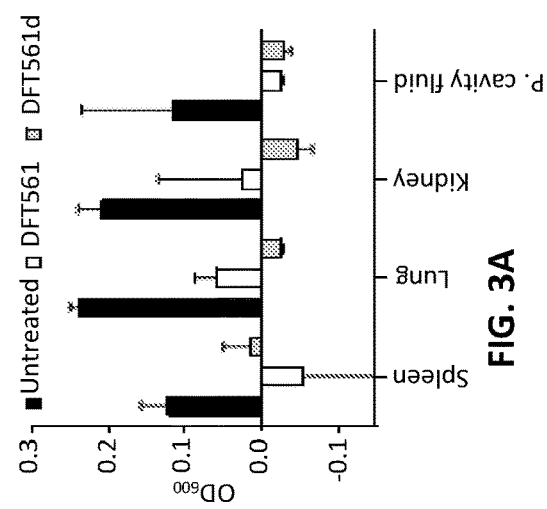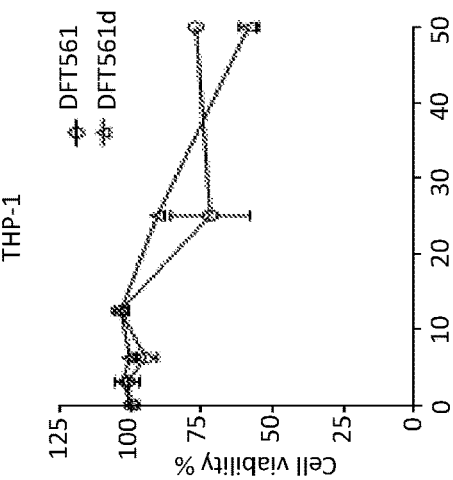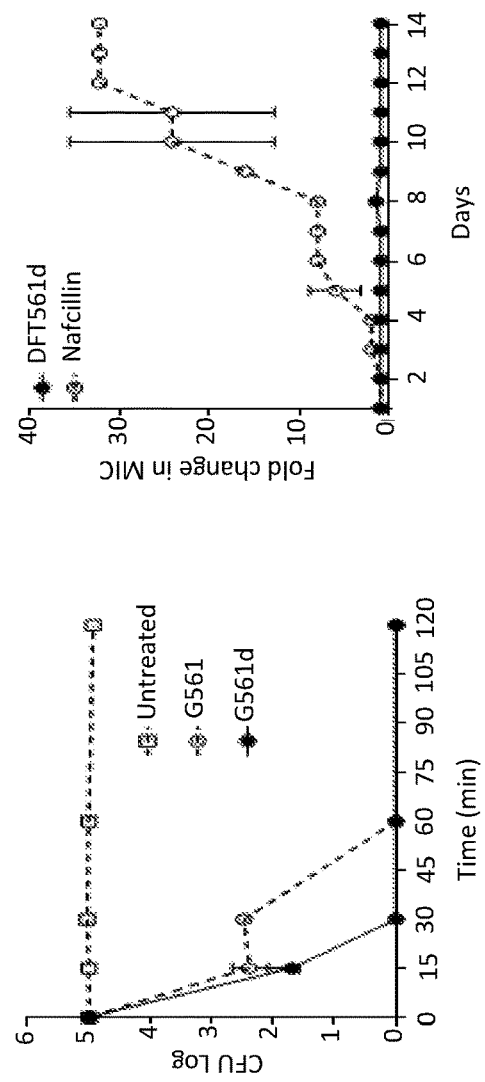

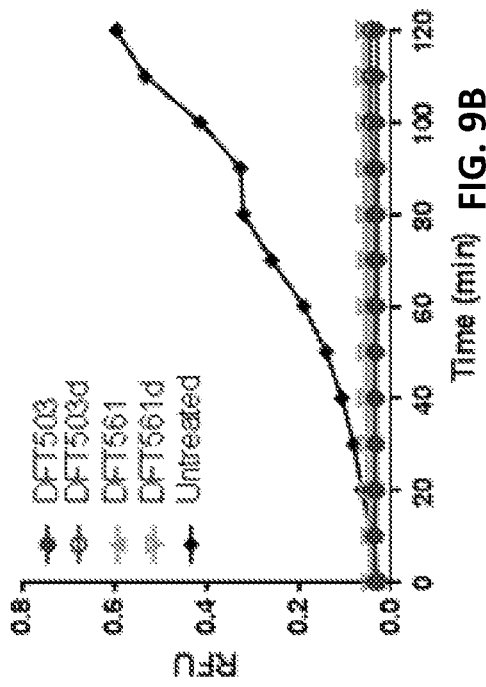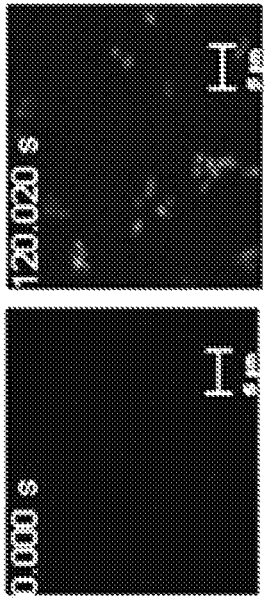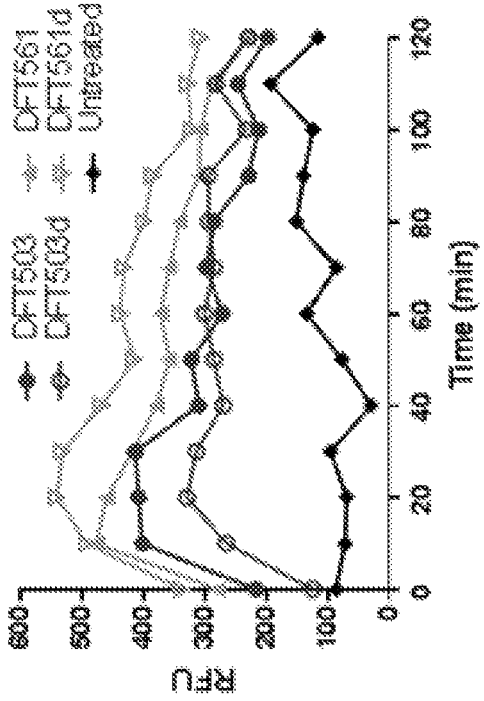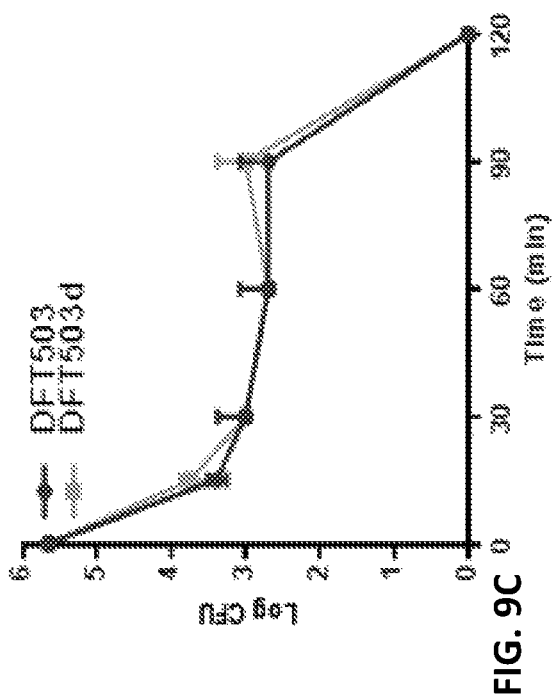

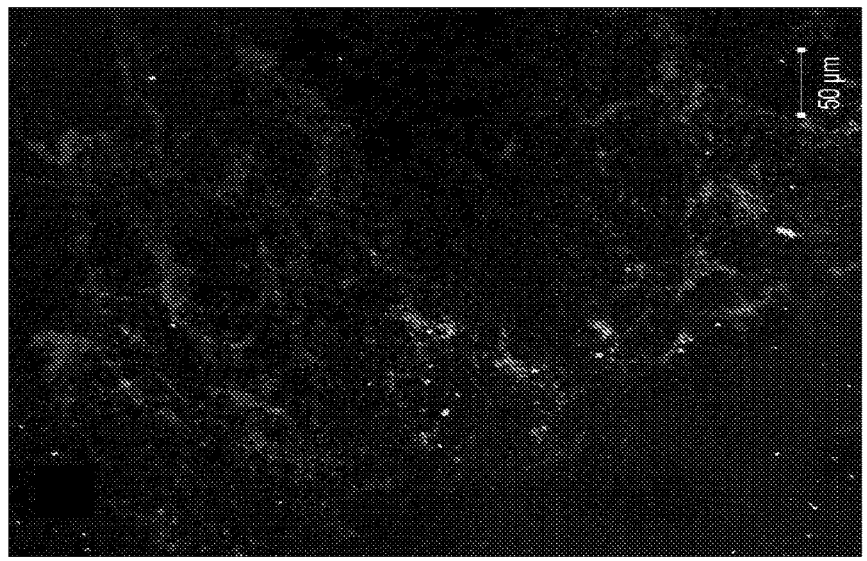
FIG. 12

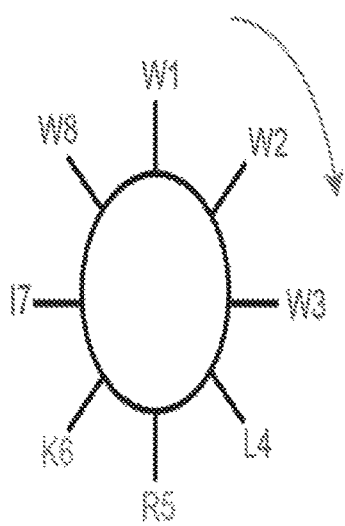
FIG. 15A
```
Start        Peptide    Sequence
Position 1:  WW291      +WWWLRKIW
Position 2:  WW292      +WWLRKIWW
Position 3:  WW293      +WLRKIWWW
Position 4:  WW294      +LRKIWWWW
Position 5:  WW295      +RKIWWWWL
Position 6:  WW296      +KIWWWWLR
Position 7:  WW297      +IWWWWLRK
Position 8:  WW298      +WWWWLRKI
```
FIG. 15B
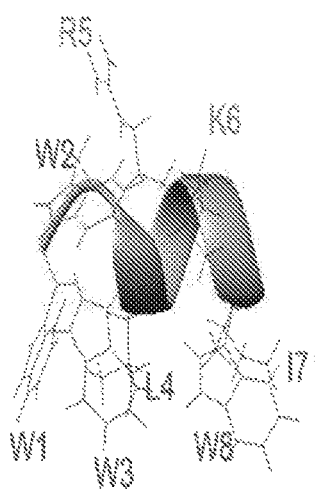
FIG. 15C
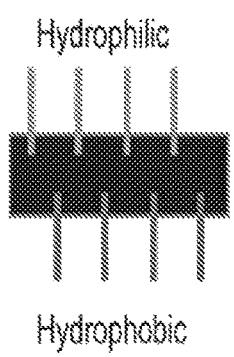
FIG. 15D
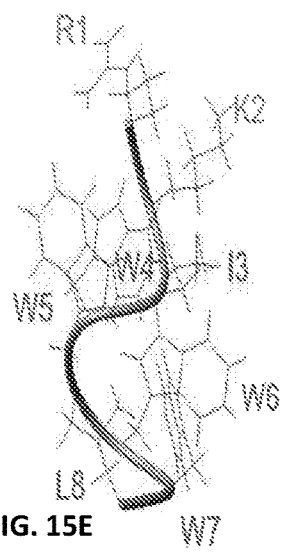
FIG. 15E
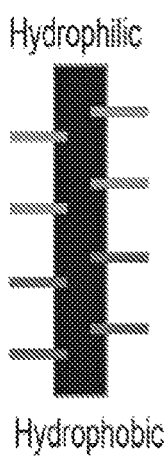
FIG. 15F
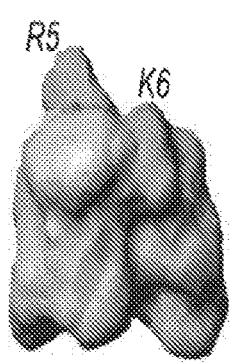
FIG. 15G
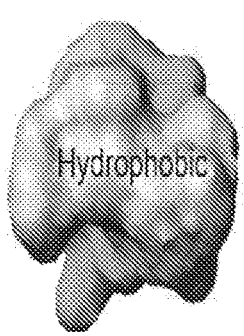
FIG. 15H
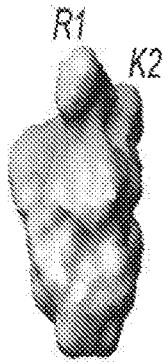
FIG. 15I
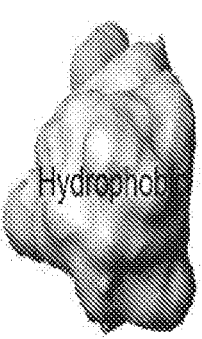
FIG. 15J

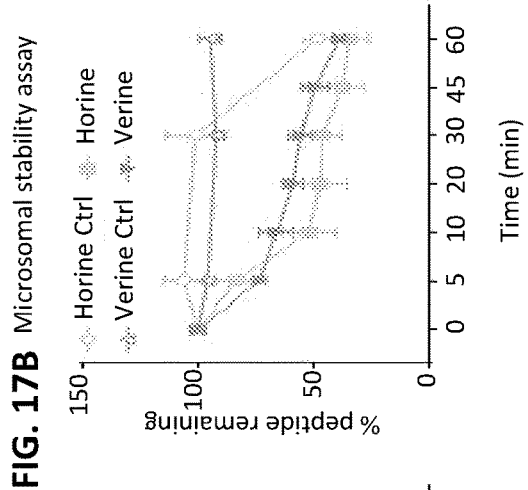
FIG. 17A
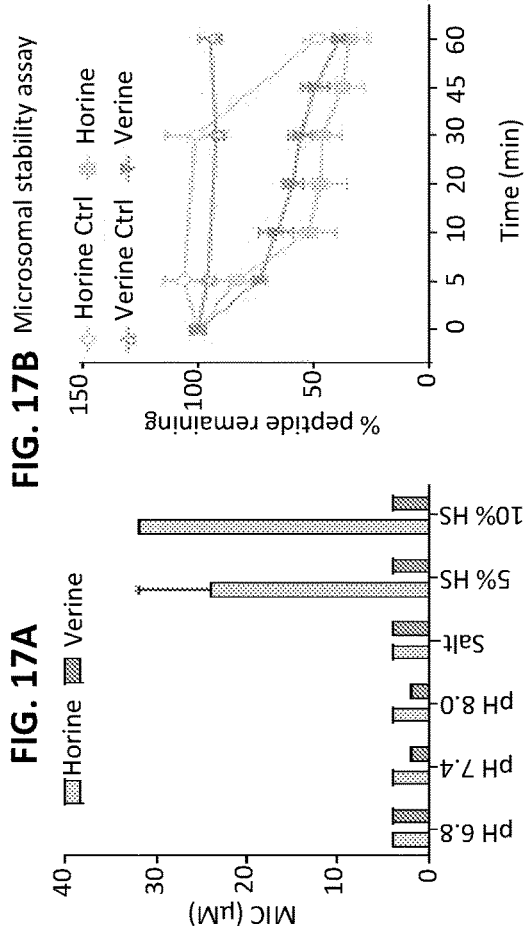
FIG. 17B
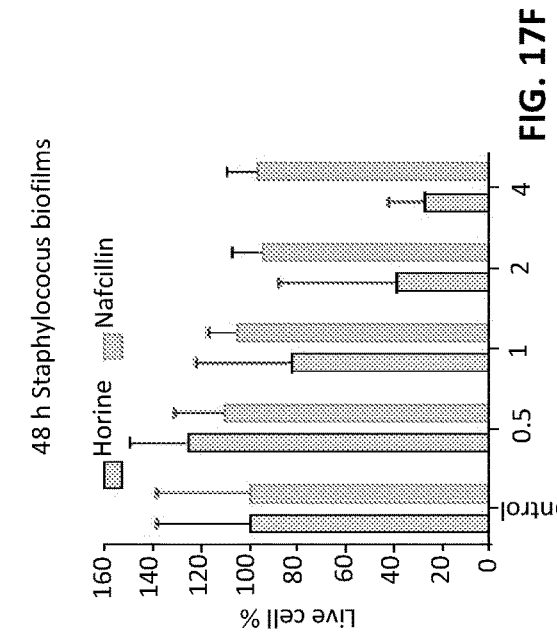
FIG. 17C
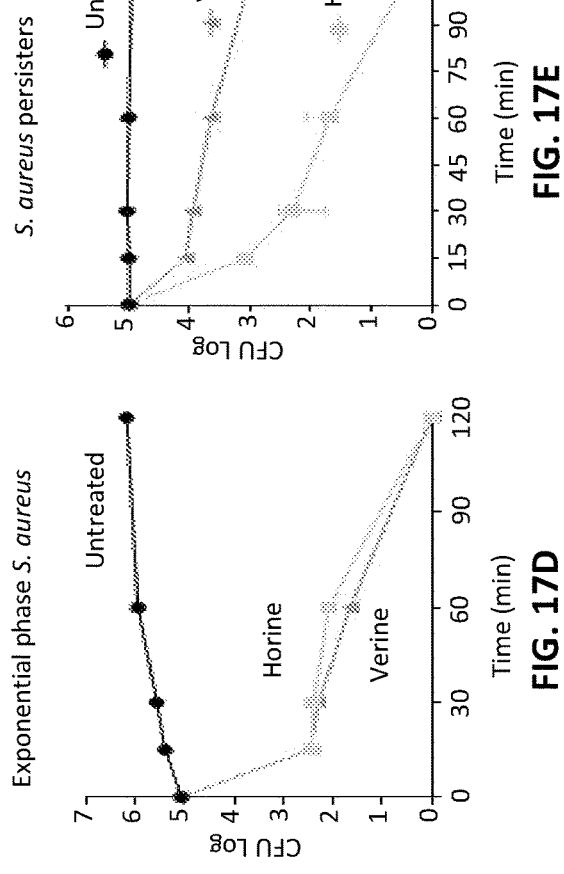
FIG. 17D
FIG. 17E
FIG. 17F

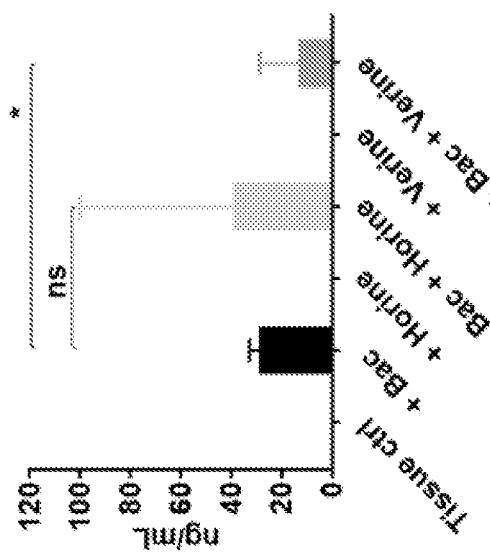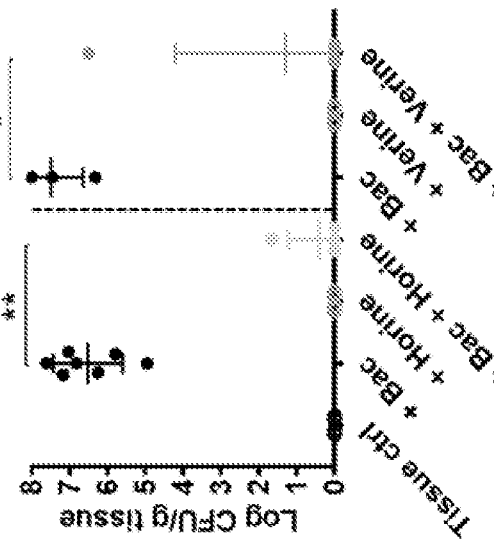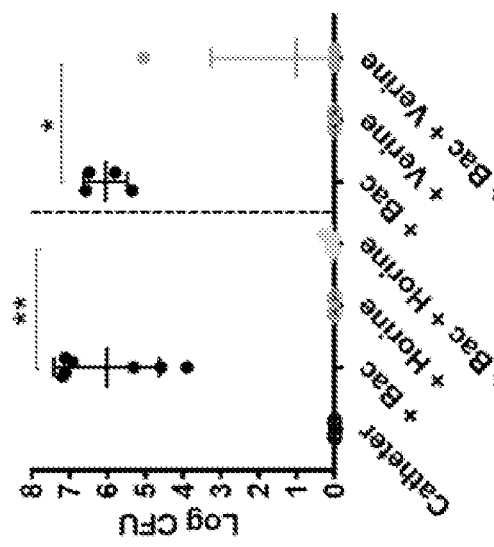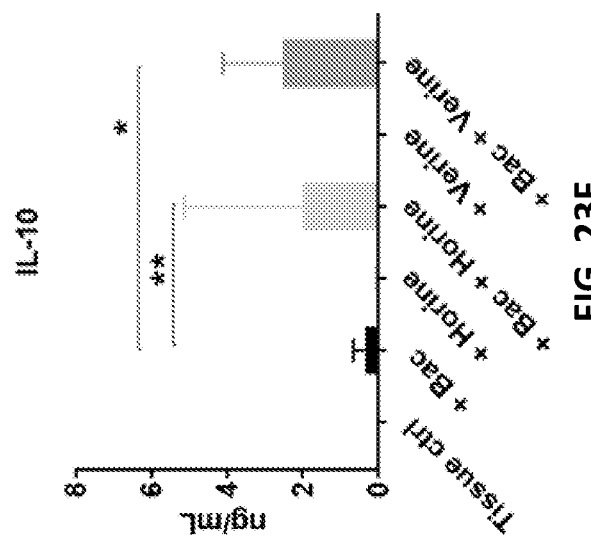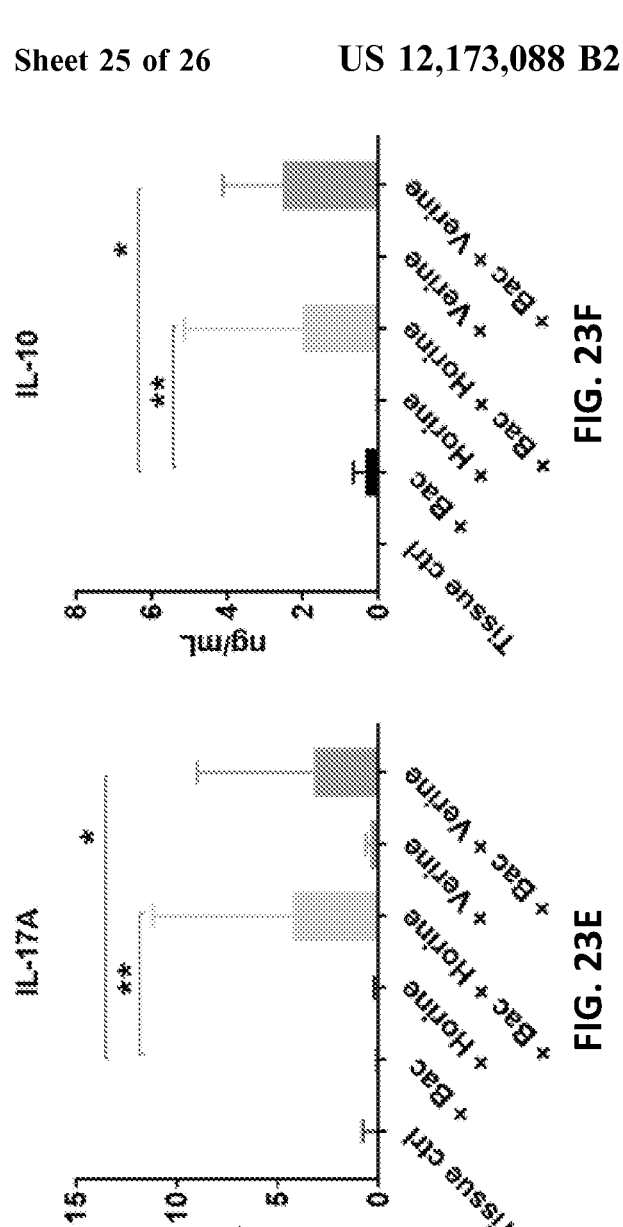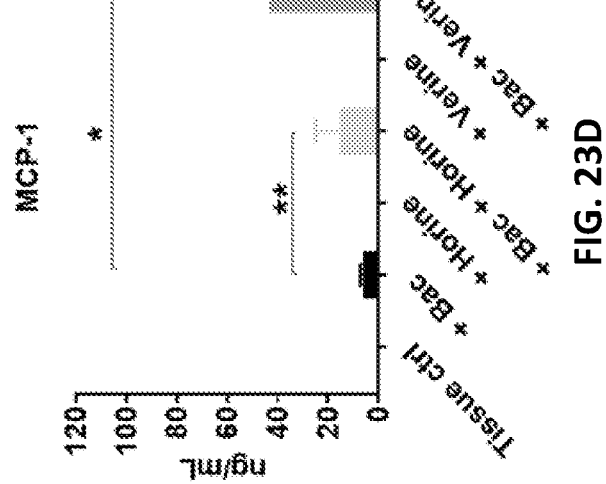

ANTI-MICROBIAL PEPTIDES

This application is a § 371 application of PCT/US2019/039792, filed Jun. 28, 2019, which claims priority under 35 U.S.C. § 119(e) to U.S. Provisional Patent Application No. 62/743,695, filed on Oct. 10, 2018, and U.S. Provisional Patent Application No. 62/862,203, filed on Jun. 17, 2019. The foregoing applications are incorporated by reference herein.

This invention was made with government support under RO1 AI105147 and RO1 AI128230 awarded by the National Institutes of Health. The government has certain rights in the invention.

FIELD OF THE INVENTION

The present invention relates to the field of antimicrobial peptides and the treatment of microbial infections. More specifically the invention provides anti-microbial peptides, anti-microbial biofilms, and methods of using such peptides and biofilms for the inhibition, treatment, and/or prevention of microbial infections.

BACKGROUND OF THE INVENTION

According to the 2013 report of the Centers for Disease Control and Prevention, antibiotic-resistant pathogens caused 23,488 deaths per year. Among them, methicillin-resistant *Staphylococcus aureus* (MRSA) alone caused 11,000 deaths per year (www.cdc.gov/drugresistance/threat-report-2013/index). Therefore, novel and potent antibiotics against MRSA are urgently needed. Antimicrobial peptides (AMPs) are important innate immune molecules that protect the host from the infection of invading pathogens. A majority of such peptides are cationic and amphipathic, allowing them to rapidly eliminate pathogens by targeting anionic membranes. Such a mechanism confers power to AMPs so that they can also kill persisters (dormant bacteria) and disrupt biofilms (bacterial community). In addition, cationic peptides regulate the host immune response to clear infection. The combination of these peptide actions renders it difficult for bacteria to develop resistance (Zasloff, M. (2002) Nature 415:389-395; Wade, et al. (1990) Proc. Natl. Acad. Sci., 87:4761-4765; Mishra, et al. (2017) Curr. Opin. Chem. Biol., 38:87-96; Wang G, Eds. (2017) Antimicrobial Peptides: Discovery, Design and Novel Therapeutic Strategies, CABI, Oxfordshire, UK, ed. 2).

SUMMARY OF THE INVENTION

In accordance with one aspect of the instant invention, antimicrobial peptides are provided. Compositions comprising at least one antimicrobial peptide of the instant invention and at least one pharmaceutically acceptable carrier are also provided. The compositions may further comprise at least one other antimicrobial compound (e.g., antibiotic). Medical devices and medical implants comprising an antimicrobial peptide (e.g., on its surface) are also provided, along with methods of making the same.

In accordance with another aspect of the instant invention, methods for inhibiting, treating, and/or preventing a microbial infection in a subject are provided. The methods comprise administering to a subject at least one antimicrobial peptide of the instant invention, particularly as a composition with a carrier or covalently attached to the surface of a medical device or implant. In a particular embodiment, the methods further comprise the administration at least one other antimicrobial treatment, such as the administration of at least one additional antibiotic.

BRIEF DESCRIPTIONS OF THE DRAWING

FIG. 1A provides a schematic of the in silico design of peptides based on a database filtering technology and subsequent optimization in vitro and in vivo efficacy test. FIG. 1B provides the amino acid sequences of major designer peptides investigated in vivo. The more lysines the peptide has, the less likely it works in vivo. DFTamP1 (SEQ ID NO: 1); DFT503 (SEQ ID NO: 23); DFT561 (SEQ ID NO: 30); DFT564 (SEQ ID NO: 33), DFT565 (SEQ ID NO: 34). FIG. 1C provides the backbone structure of DFTamP1. FIG. 1D provides the potential surface of DFTamP1. FIG. 1E provides the backbone structure of DFT503. FIG. 1F provides the potential surface of DFT503.

FIG. 2 provides a graph of the membrane depolarization of *S. aureus* USA300 by DFT503, DFT561, DFT564 and DFT565.

FIG. 3A provides the anti-staphylococcal activity of DFT561d in the presence of supernatants of mouse spleen, lung, kidney homogenized tissues and peritoneal cavity fluid (50%). FIG. 3B provides the antibiofilm capability of DFT561 and its D-form DFT561d in disrupting the 24-hour established *S. aureus* biofilms. FIG. 3C shows DFT561d is effective in rapidly killing of stationary phase *S. aureus* USA300 when treated at 12.5 µM once at 0 minutes or 6.25 µM twice at 0 and 15 minutes. FIG. 3D shows that DFT561 and its D-form rapidly kill nafcillin induced persistors cells of *S. aureus* USA300. FIG. 3E shows the resistance development of *S. aureus* USA300 under the selection pressure of DFT561d (filled circles) or nafcillin (open circles). While *S. aureus* developed resistance to nafcillin after 14 in vitro passages, no resistance to DFT561d was detected. FIG. 3F shows the cytotoxicity of DFT561 and its D-form to THP-1 monocytes. FIG. 3G shows the effects of *S. aureus* USA300 and DFT561d on the level of TNF-α secreted from the THP-1 monocytes. FIG. 3H shows the effects of *S. aureus* USA300 and DFT561d on the level of MCP-1 secreted from the THP-1 monocytes. FIG. 3I shows the effects of DFT503 treatment on the level of TNF-α and MCP-1 in mouse blood plasma. Statistical significance was analyzed using one tailed distribution student t-test with sample of equal variance, where $p<0.05$ is considered as significant (* $p<0.05$  $p<0.01$, * $p<0.001$).

FIG. 4 provides the killing kinetics of DFT561d on the exponential phase of *S. aureus* USA300. The peptide was treated either at 12.5 µM all at one time or twice 6.25 µM with a 15 minute interval. The optimized peptide DFT561d is able to rapidly kill *S. aureus* USA300.

FIG. 5 shows the in vivo efficacy of database designed peptides against *S. aureus* infection using neutropenic mice. Mouse neutropenia was induced by two injections of cyclophosphamide (150 mg/kg and 100 mg/kg) −4 and −1 days prior to infection and treatment. Animals infected with *S. aureus* USA300 ($2 \times 10^6$ CFU/mouse) were treated intraperitoneally 2 hours post infection with a single peptide dose (n=5 mice per group) of DFT503; DFT561; DFT564; and DFT565 at 5 mg/kg. Animals were euthanized 24 hours post treatment, organs harvested, weighed, and CFU enumerated in spleen, lung, kidney and liver. The bacterial loads from each mouse were plotted as individual dots and error bars represent the deviation from the average within the experimental group. Statistics was determined via Mann-Whitney test (*, $P<0.05$; **, $P<0.01$, and n.s., no significance).

FIG. 6 shows DFT561d dose-dependent efficacy against *S. aureus* USA300 infection in neutropenic mice. Animals (n=4 mice per group) were i.p. treated with a single dose of DFT561d 2 hours post infection at 1, 2.5, and 5 mg/kg doses. Cyclophosphamide induced neutropenic mice were infected with *S. aureus* USA300 at $2\times10^6$ CFU per mouse. Animals were sacrificed after 24 hours post infection and organs were harvested, weighed and CFU were determined in spleen, lungs, kidney and liver by plating and colony counting. The bacterial loads from each mouse were plotted as individual points and error bars represent the deviation within the experimental group. * $P<0.05$  $P<0.01$, *$P<0.001$ and n.s. represents no significance (determined by Mann-Whitney test).

FIG. 7 shows the comparison of in vivo efficacy between DFT561 and DFT561d. DFT561 and DFT561d efficacy against *S. aureus* USA300 infection in a neutropenic mouse model. Animals were treated with a single dose (i.p., 2 hours post infection, n=5 mice per group) of DFT561 or DFT561d at the 5 mg/kg dose. Cyclophosphamide induced neutropenic mice were infected with *S. aureus* USA300 at $2\times10^6$ CFU per mouse. Animals were sacrificed after 24 hours post infection and organs were harvested, weighed, and CFU were determined in spleen, lung, kidney and liver by plating and colony counting. The bacterial loads from each mouse are plotted as individual dots and error bars represent the deviation within the experimental group. Statistical analysis determined by Mann-Whitney test: * $P<0.05$, ** $P<0.01$, and n.s.=no significance.

FIG. 8 shows the improved efficacy of two injections of DFT503 against *S. aureus* USA300 in a neutropenic mouse model. Animals were treated with two peptide injections (i.p., 2 and 24 hours post infection, n=5 mice per group) of DFT503 at 5 mg/kg per mouse for each injection. Cyclophosphamide induced neutropenic mice were infected with *S. aureus* USA300 at $5.8\times10^5$ CFU per mouse. Animals were sacrificed after 48 hours post infection and organs were harvested, weighed, and CFU were determined in spleen, lungs, kidney and liver by plating and colony counting. The bacterial loads from each mouse are plotted as individual points and error bars represent the deviation within the experimental group. * $P<0.05$  $P<0.01$, *$P<0.001$ and n.s. represents no significance (determined by Mann-Whitney test).

FIG. 9A provides a propidium iodide based membrane permeation assay. DFT503 and DFT503d were less effective than DFT561 and DFT561d. The *S. aureus* USA300 wells without peptide treatment were used as background. All peptides were treated at a fixed concentration of 1.56 µM. FIG. 9B provides growth inhibition curves obtained simultaneously with the membrane permeation experiment. FIG. 9C shows the kinetic killing of *S. aureus* USA300 by DFT503 or its D-form at 3.1 µM. FIG. 9D provides images of live cell based FITC-fluorescence detection due to the membrane-damaging effect of DFT503 or DFT503d.

FIG. 10 provides the real time fluorescence measurement of *S. aureus* USA300 bacteria treated with 3.1 µM DFT506d or antibiotics. Fluorescence from the propidium iodide dye was measured using an excitation and emission wavelengths of 584 nm and 620 nm, respectively. Only membrane permeating DFT561d and daptomycin caused a fluorescence increase, while the curves for non-membrane targeting antibiotics (e.g., vancomycin and rifamycin) are similar to untreated.

FIGS. 11A and 11B show *S. aureus* USA300 membrane depolarization by DFT peptides: DFT503 and DFT503d (FIG. 11A) and DFT561 and DFT561d (FIG. 11B). Mid logarithmic phase grown cultures of *S. aureus* USA300 re-suspended in an energized PBS with glucose medium were incubated with the fluorescent indicator dye DiBAC4. Membrane depolarization was detected by measuring fluorescence change over time. Peptides and daptomycin were added after 20 minutes until fluorescence stabilization and observed for another 40 minutes. Plots were for 12.5 µM of peptides and daptomycin. Triton™ X-100 (0.1%) was used as a positive control. The D-forms are stronger in membrane depolarization than the L-forms of DFT503 or DFT561.

FIG. 12 shows the antibiofilm activities of DFT503 and DFT503d against established biofilms (24 hours) of *S. aureus* USA300 at 12.5 µM and assessed by confocal laser scanning microscopy using live and dead staining. Untreated control biofilms (left), biofilms treated with DFT503 (center) and DFT503d (right) at 12.5 µM, respectively. A stronger antibiofilm ability was observed for the D-form DFT503d than the L-form DFT503.

FIG. 13A shows the efficacy of DFT503 in normal mice (n=5 mice per group). The bacterial loads from each mouse were plotted as individual points and error bars represent the deviation from the average. * $P<0.05$, ** $P<0.01$, and n.s. represents no significance (determined by Mann-Whitney test). FIG. 13B provides the IL-17A and IL-10 cytokine levels in mouse plasma. Samples were collected from non-neutropenic mice infected with *S. aureus* USA300 with and without DFT503 treatment.

FIG. 14 provides a RK-Pho diagram depicting the correlation between peptide hydrophobic content and (R+K) %. In total, 3014 antimicrobial peptides in the current APD were used and separated into 10 bins based on hydrophobic contents (0-10, 11-20, 21-30, 31-40, 41-50, 51-60, 61-70, 71-80, 81-90, and 91-100%), which are represented as 10, 20, 30, 40, 50, 60, 70, 80, 90, and 100 on the X axis of the plot. The sum of the averaged R % and K % from each bin is represented on the Y axis. 80% of these 2D dots fall between 10 and 20% of (R+K) %. Also included in this plot are peptides that were tested for systemic efficacy in (neutropenic) mouse models.

FIGS. 15A and 15B show sequence permutation led to two distinct amphipathic models. WW291 to WW298 are SEQ ID NO: 41-48, respectively. FIGS. 15C and 15D show a classic helix of WW291 with a horizontal axis. FIGS. 15E and 15F show a non-classic spiral structure of WW295 with a vertical axis. FIGS. 15G-15J provide the potential surfaces for WW291 (FIGS. 15G, 15H) and WW295 (FIGS. 15I, 15J).

FIG. 16A shows the growth inhibition and FIG. 16B shows the propidium iodide-based membrane permeation of *S. aureus* USA300 in TSB media treated with 4 µM WW291 (horine patent peptide) and WW295 (verine parent peptide) at 37° C. with shaking at 100 rpm for 2 hours. The absorbance and fluorescence were recorded using a FLUOstar® Omega microplate reader. Both WW291 and WW295 can inhibit *S. aureus* growth and permeate bacterial membranes.

FIG. 17A shows the effects of physiological pH, salt and human serum (HS) on the antimicrobial activity of horine and verine. FIG. 17B shows the microsomal stability of horine and verine. FIG. 17C shows both peptides are stable to the proteolytic action of mouse plasma and peritoneal fluids. FIG. 17D shows horine kills the exponential phase of *S. aureus* USA300 rapidly. FIG. 17E shows that horine and verine kill nafcillin-induced persisters of *S. aureus* USA300. FIG. 17F shows that horine disrupts 48-hour established biofilms of *S. aureus*. FIG. 17G shows that verine is effective in disrupting 48-hour established *Klebsiella* biofilms.

Figure 20:
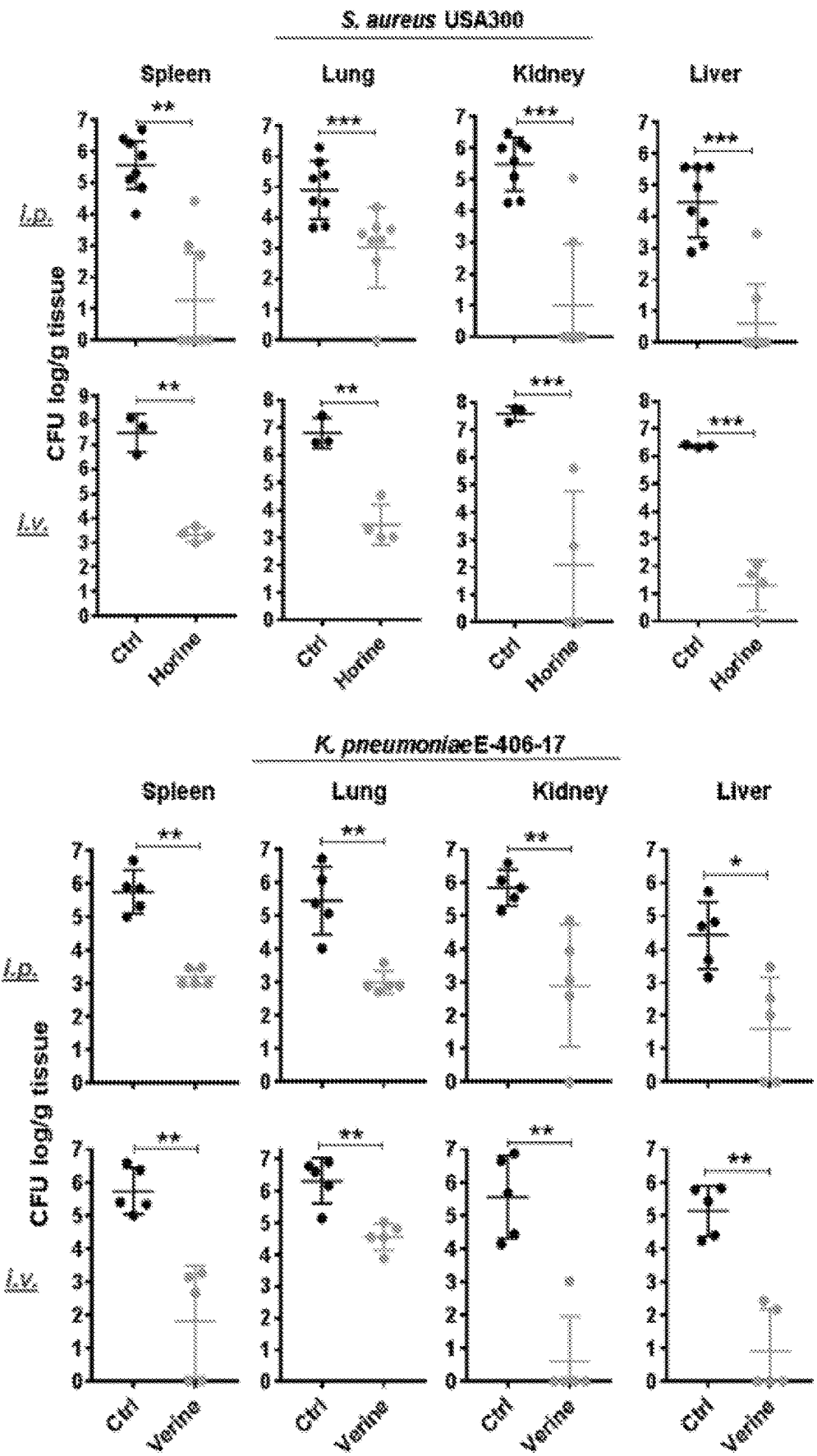

FIG. 20 shows the systemic in vivo efficacy of horine and verine in neutropenic mice. CFU loads in spleen, lungs, kidney and liver of neutropenic mice 24 hours after infection with S. aureus USA300 at $2\times10^6$ CFU per mouse with and without horine treatment (i.p., 2 hours post infection, n=8 C57BL/6 mice for i.p., and n=4 BALB/c mice per group for i.v. administration) at 10 mg/kg, and with K. pneumoniae E-406-17 at $5\times10^5$ CFU per mouse with and without verine treatment (i.p., 2 hours post infection, n=8 C57BL/6 mice for i.p., and n=4 BALB/c mice per group for i.v. administration) at 15 mg/kg. The bacterial loads from each mouse plotted as individual points and error bars represent the deviation within the experimental group. * $P<0.05$  $P<0.01$, and * $P<0.001$ (determined by Mann-Whitney test).

Figure 21:
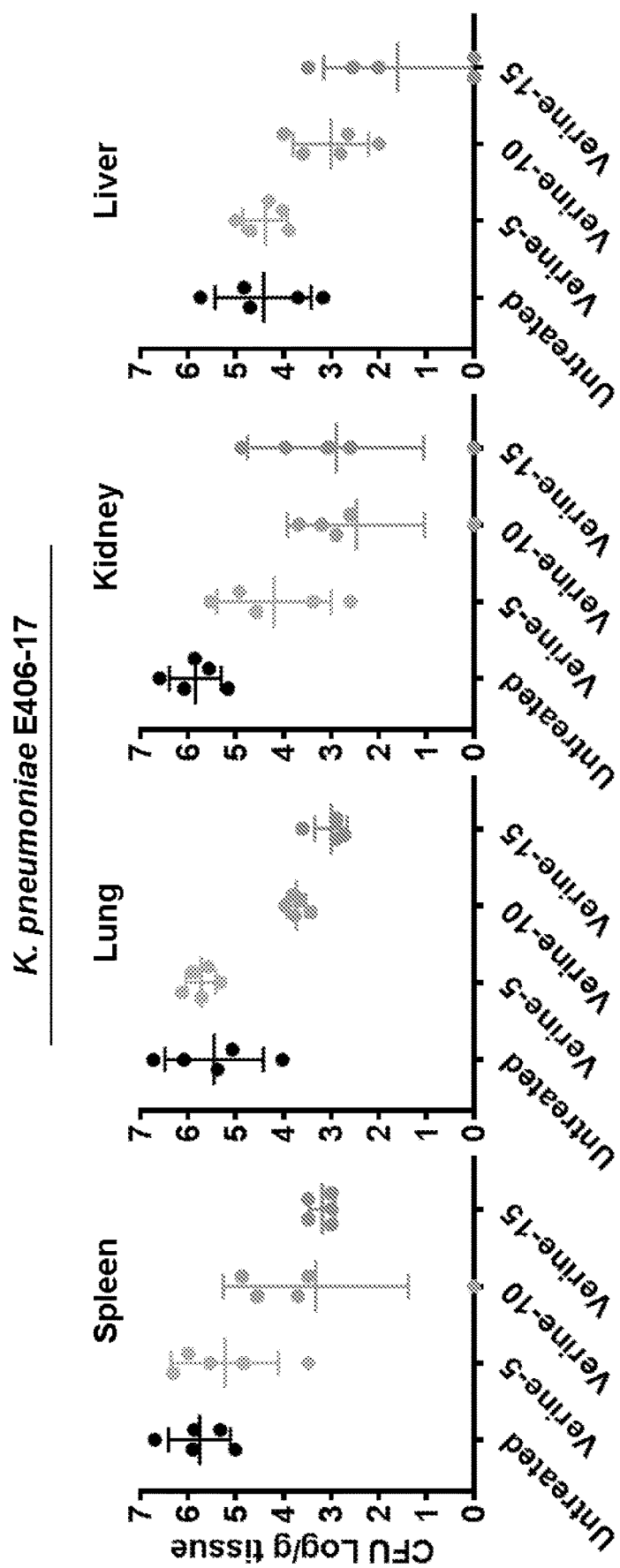

FIG. 21 shows the dose-dependent efficacy of verine in K. pneumoniae E406-17 infected C57BL/6 mice treated with a single dose at 5, 10, or 15 mg/kg per mouse.

Figure 22:
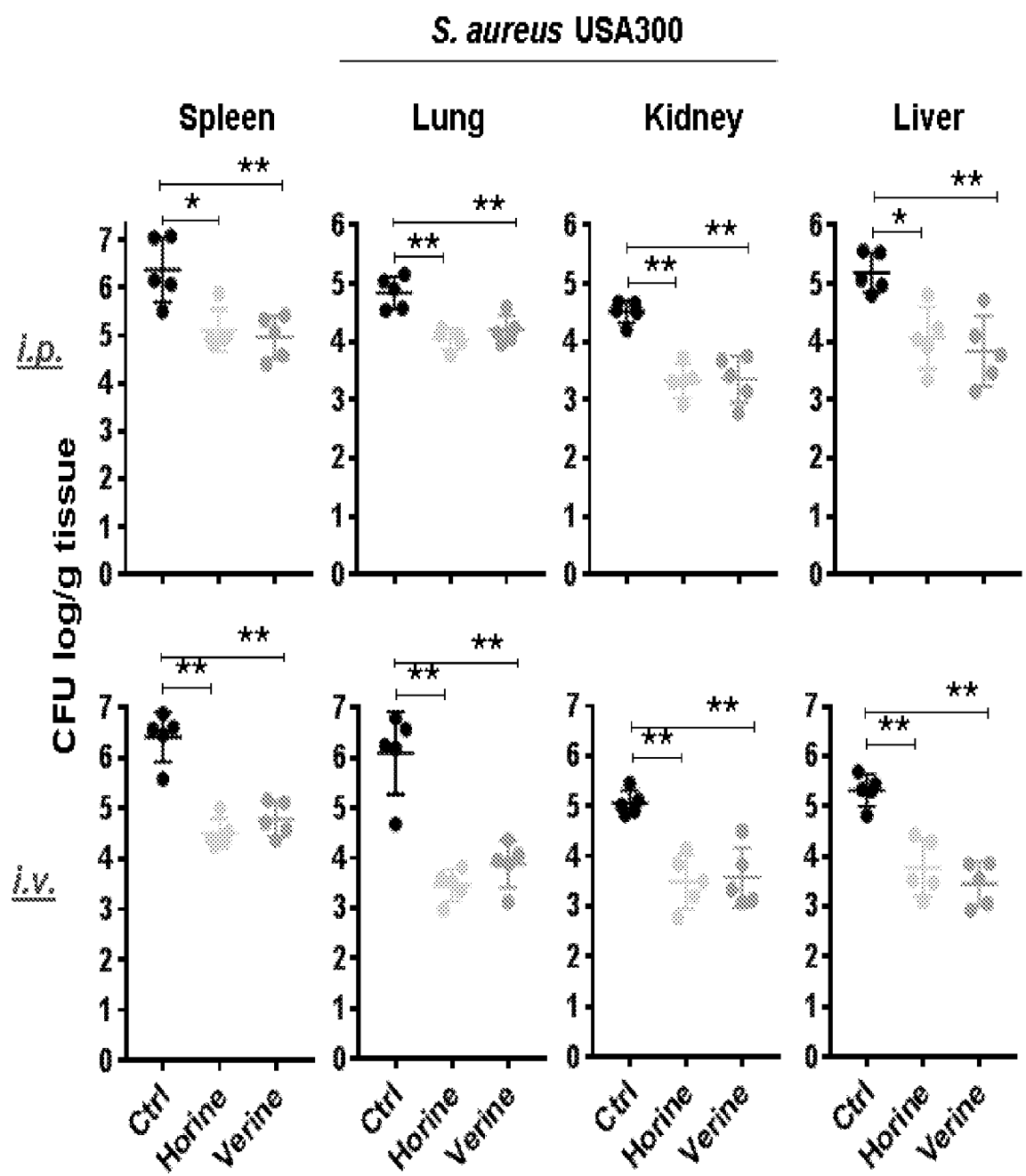

FIG. 22 shows the efficacy of horine and verine in normal C57BL/6 mice (i.e., non-neutropenic). Animals were treated with a single dose of peptide (i.p., 2 hours post infection, n=5 mice per group at 10 mg/kg per mouse). Mice were infected with S. aureus USA300 at $2\times10^8$ per mouse. Animals were sacrificed 24 hours post treatment. Vital organs were harvested and bacterial loads enumerated in spleen, lung, kidney, and liver by plating on blood agars and colony counting. The bacterial loads in tissues were plotted as individual points and error bars represent the deviation from the average. * $P<0.05$,  $P<0.01$, and * $P<0.001$ (determined by Mann-Whitney test).

FIGS. 23A-23F show the in vivo efficacy and immune modulatory properties of horine and verine on a catheter-associated mouse biofilm model. Three days post infection, peptide treatment significantly reduced S. aureus USA 300 biofilms on the mouse-associated catheter (FIG. 23A) and the surrounding tissues (FIG. 23B). Cytokine levels of TNF-α (FIG. 23C), MCP-1/CCL2 (FIG. 23D), IL-17 (FIG. 23F) and IL-10 (FIG. 23F) in homogenized tissue samples were also quantified using ELISA. Bacterial burdens experiment data were analyzed using Mann-Whitney test and for cytokine, an unpaired one-tailed student's t-test with sample of equal variance was used to determine statistical significance. Results were expressed as mean±error and data are considered as statistically significant when p<0.05 (* p<0.05,  p<0.005, *p<0.0001).

Figure 24A:
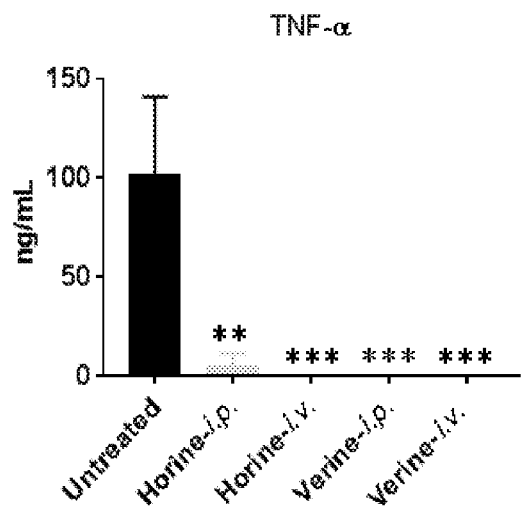
Figure 24B:
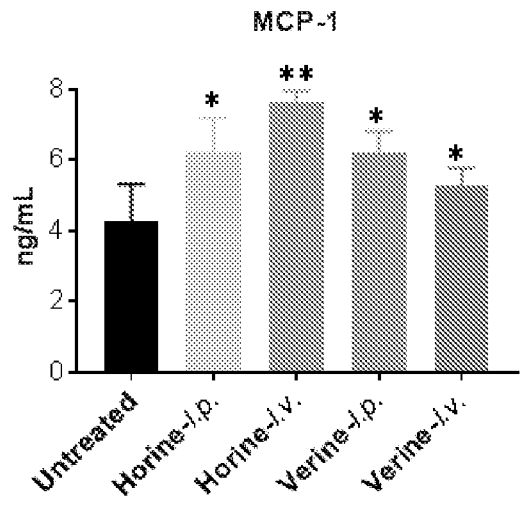
Figure 24C:
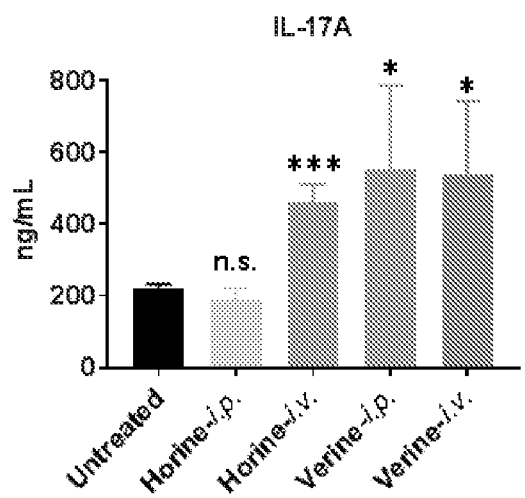
Figure 24D:
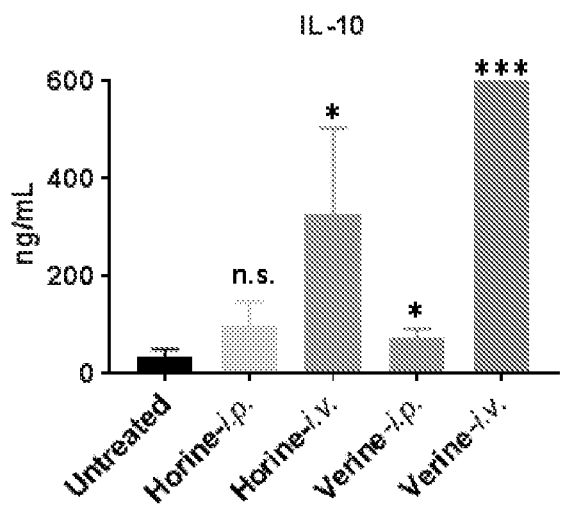

FIGS. 24A-24D show chemokines of S. aureus-infected normal mice after a single dose treatment with horine or verine. Both peptides suppressed TNFα (FIG. 24A) and stimulated MCP-1 (FIG. 24B), IL-17A (FIG. 24C), and IL-10 (FIG. 24D). The exceptions involved i.p. treatment of horine for IL-17A and IL-10 and verine for IL-10.

DETAILED DESCRIPTION OF THE INVENTION

The proliferation of drug resistant bacteria necessitates new bactericidal agents. The present invention provides a variety of short peptides that can kill a wide variety of bacteria including Staphylococcus. The peptides are further capable of chemical affixation to polymer implements and other kinds of materials.

In accordance with the instant invention, antimicrobial peptides are provided. In a particular embodiment of the instant invention, the peptide comprises the sequence: GLLSLLSLLGKLL (SEQ ID NO: 1), wherein at least one amino acid has been substituted, inserted, and/or deleted. In a particular embodiment, the peptide comprises the sequence: GLLSLLSLLGKLL (SEQ ID NO: 1), wherein at least one amino acid has been substituted and/or deleted. In a particular embodiment, the peptide comprises the sequence: GLLSLLSLLGKLL (SEQ ID NO: 1), wherein one or two amino acids has been substituted and/or deleted. In a particular embodiment, the peptide comprises the sequence: GLLSLLSLLGKLL (SEQ ID NO: 1), wherein one acid has been substituted and/or deleted. In a particular embodiment, at least one of the leucine amino acids, particularly at positions 5, 6, 8, 9, 12, or 13, of GLLSLLSLLGKLL (SEQ ID NO: 1) is substituted and/or deleted. In a particular embodiment, the amino acid substitutions are conservative amino acid changes. In a particular embodiment, hydrophobic amino acids (e.g., alanine, isoleucine, leucine, methionine, phenylalanine, valine, proline, or glycine; particularly alanine, isoleucine, leucine, valine, or glycine) are substituted into GLLSLLSLLGKLL (SEQ ID NO: 1). In a particular embodiment, alanine amino acids are substituted into GLLSLLSLLGKLL (SEQ ID NO: 1). In a particular embodiment, the peptide comprises any one of SEQ ID NOs: 2-15 and 18. In a particular embodiment, the peptide comprises any one of SEQ ID NOs: 2-12 and 18. In a particular embodiment, the peptide comprises any one of SEQ ID NOs: 2-9 and 18.

In a particular embodiment of the instant invention, the peptide comprises the amino acids of GLLSLLSLLGKLL (SEQ ID NO: 1) in a shuffled sequence. In other words, the peptide comprises an amino acid sequence comprising the same amino acid composition but in a different order. In a particular embodiment, the peptide comprises any one of SEQ ID NOs: 22-28. In a particular embodiment, the peptide comprises GLSLLLSLGLKLL (SEQ ID NO: 23).

In a particular embodiment of the instant invention, the peptide comprises the sequence: GLSLLLSLGLKLL (SEQ ID NO: 23), wherein at least one amino acid has been substituted, inserted, and/or deleted. In a particular embodiment, the peptide comprises the sequence: GLSLLLSLGLKLL (SEQ ID NO: 23), wherein at least one amino acid (particularly only one) has been substituted, particularly wherein the LLL sequence is retained. In a particular embodiment, lysine or arginine (particularly lysine) amino acids are substituted into GLSLLLSLGLKLL (SEQ ID NO: 23). In a particular embodiment, the peptide comprises any one of SEQ ID NOs: 29-34. In a particular embodiment, the peptide comprises GLKLLLSLGLKLL (SEQ ID NO: 30). In a particular embodiment, the peptide comprises GLKLLLKLGLKLL (SEQ ID NO: 33). In a particular embodiment, the peptide comprises KLKLLLKLGLKLL (SEQ ID NO: 34).

In a particular embodiment of the instant invention, the peptide comprises a sequence permutated peptide of the sequence: WWWLRKIW (SEQ ID NO: 41). In other words, the peptide comprises the same order of amino acids as SEQ ID NO: 41 except that the first or N-terminal amino acid is different. In a particular embodiment, the peptide comprises any one of SEQ ID NOs: 42-48.

In a particular embodiment of the instant invention, the peptide comprises the sequence: WWWLRRIW (SEQ ID NO: 49), wherein at least one amino acid (particularly only one) has been substituted, inserted, and/or deleted. In a particular embodiment, the peptide comprises the sequence: WWWLRRIW (SEQ ID NO: 49), wherein at least one amino acid has been substituted. In a particular embodiment, lysine or arginine amino acids (particularly arginine amino acids) are substituted into WWWLRRIW (SEQ ID NO: 49). In a particular embodiment, the peptide comprises any one of SEQ ID NOs: 50-55. In a particular embodiment, the peptide comprises WWWLRRRW (SEQ ID NO: 54).

In a particular embodiment of the instant invention, the peptide comprises the sequence: RRRWWW (SEQ ID NO: 60), RRRWWWW (SEQ ID NO: 61), or RRRWWWWX (SEQ ID NO: 62), wherein X is any amino acid (e.g., alanine, isoleucine, leucine, methionine, phenylalanine, valine, proline, or glycine; particularly alanine, isoleucine, leucine, valine, or glycine; particularly leucine, valine, or alanine). In a particular embodiment, the peptide comprises RRRWWW (SEQ ID NO: 60), RRRWWWW (SEQ ID NO: 61), or RRRWWWWX (SEQ ID NO: 62), optionally with 1 or 2 additional amino acids at either terminus. In a particular embodiment, the peptide comprises any one of SEQ ID NOs: 56-59. In a particular embodiment, the peptide comprises RRRWWWWV (SEQ ID NO: 57).

The amino acid sequence of the antimicrobial peptide of the instant invention may have at least 75%, at least 80%, at least 85%, at least 90%, at least 95%, at least 97%, at least 99%, or 100% homology or identity with any peptide described herein (e.g., SEQ ID NOs: 1-62) or any one of the above sequences, particularly at least 90% homology or identity (e.g., the sequence may contain additions, deletions, and/or substitutions). In a particular embodiment, the antimicrobial peptide of the instant invention may extend beyond any peptide described herein (e.g., SEQ ID NOs: 1-62) or any one of the above sequences at the amino and/or carboxyl terminus by 1, 2, 3, 4, 5, 6, 7, 8, 9, or 10 amino acids, particularly by 1, 2, 3, 4, or 5 amino acids, by 1, 2, or 3 amino acids, by 1 or 2 amino acids, or by 1 amino acid. In yet another embodiment, the antimicrobial inhibitory peptides of the instant invention may also be in reverse orientation (i.e., the sequence from amino terminus to carboxyl terminus is reversed).

In a particular embodiment, the peptides of the instant invention have fewer than about 50 amino acids, fewer than about 25 amino acids, fewer than about 20 amino acids, fewer than about 17 amino acids, fewer than about 15 amino acids, fewer than 12 amino acids, fewer than 10 amino acids, or fewer than 9 amino acids. In a particular embodiment, the peptides of the instant invention have more than about 6 amino acids, particularly more than about 7 amino acids. In a particular embodiment, the peptides of the instant invention are about 7 to about 12 amino acids in length, about 8-10 amino acids in length, about 8 or 9 amino acids in length, or about 8 amino acids in length.

In a particular embodiment, the antimicrobial peptide of the instant invention comprises any peptide described herein (e.g., SEQ ID NOs: 1-62) or any one of the above sequences and a terminal cysteine. In a particular embodiment, the cysteine is at the amino terminus. In a particular embodiment, the cysteine is at the carboxyl terminus. The presence of the cysteine provides functionality to allow the covalent linkage of the antimicrobial peptide to, for example, a solid surface (e.g., a medical implant).

As stated hereinabove, the antimicrobial peptide of the instant invention may contain substitutions for the amino acids of the provided sequence. These substitutions may be similar to the amino acid (i.e., a conservative change) present in the provided sequence (e.g., an acidic amino acid in place of another acidic amino acid, a basic amino acid in place of a basic amino acid, a hydrophobic amino acid in place of a hydrophobic amino acid, a polar amino acid for a polar amino acid, etc.). The substitutions may also comprise amino acid analogs and mimetics. In a particular embodiment, the substitutions are predicted to promote and/or retain helicity or helix formation.

The antimicrobial peptide of the instant invention may have capping, protecting and/or stabilizing moieties at the C-terminus and/or N-terminus. Such moieties are well known in the art and include, without limitation, amidation and acetylation. In a particular embodiment, the peptides of the instant invention are amidated The peptide template may also be lipidated or glycosylated at any amino acid (i.e., a glycopeptide). In particular, these peptides may be PEGylated to improve druggability. The number of the PEG units ($NH_2(CH_2CH_2O)CH_2CH_2CO$) may vary, for example, from 1 to about 50.

The antimicrobial peptide of the instant invention may also comprise at least one D-amino acid instead of the native L-amino acid. The antimicrobial peptide may comprise only D-amino acids. In a particular embodiment, the antimicrobial peptides comprise D-amino acids which are spaced apart by about 1, 2, 3, and/or 4 (e.g., 3) consecutive L-amino acids.

The antimicrobial peptides of the instant invention may contain at least one derivative of standard amino acids, such as, without limitation, fluorinated residues or nonstandard amino acids (e.g., beta-amino acids). In yet another embodiment, the peptide may also be circulated head to tail or locally involving a few residues.

The present invention also encompasses compositions comprising at least one antimicrobial peptide of the instant invention and at least one carrier (e.g., a pharmaceutically acceptable carrier). In a particular embodiment, the composition comprises at least two peptides of the instant invention (e.g., a peptide comprising SEQ ID NO: 54 and a peptide comprising SEQ ID NO: 62 (e.g., SEQ ID NO: 57). The present invention also encompasses methods for preventing, inhibiting, and/or treating microbial infections, including microbial/bacterial biofilms. The compositions of the instant invention can be administered to an animal, in particular a mammal (e.g., a human) in order to treat, inhibit, and/or prevent a microbial (e.g., bacterial such as by *E. coli, S. aureus*, any the ESKAPE pathogen (including *Enterococcus faecium, Staphylococcus aureus, Klebsiella pneumoniae, Acinetobacter baumannii, Pseudomonas aeruginosa*, and *Enterobacter* species), MRSA, etc.) infection (e.g., the composition may be administered before, during, and/or after a microbial infection). The compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time and/or at different times (e.g., sequentially). The composition(s) comprising at least one antimicrobial peptide of the instant invention and the composition(s) comprising at least one additional antibiotic may be contained within a kit.

The antimicrobial peptides of the present invention may be prepared in a variety of ways, according to known methods. In a particular embodiment, the antimicrobial peptides of the instant invention are chemically synthesized. For example, the peptides may be synthesized using a liquid-phase method or solid-phase method. The chemically synthesized peptides may then be purified (e.g., by HPLC).

The antimicrobial peptides may also be purified from appropriate sources (e.g., bacterial or animal cultured cells or tissues, optionally transformed) by immunoaffinity purification. The availability of nucleic acid molecules encoding the antimicrobial peptides enables production of the protein using in vitro expression methods and cell-free expression systems known in the art.

Larger quantities of antimicrobial peptides may be produced by expression in a suitable prokaryotic or eukaryotic system. For example, part or all of a DNA molecule encoding for an antimicrobial peptide may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Antimicrobial peptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemaglutinin epitope. Such methods are commonly used by skilled practitioners.

Antimicrobial peptides of the invention, prepared by the aforementioned methods, may be analyzed and verified according to standard procedures. For example, such protein may be subjected to amino acid sequence analysis, according to known methods.

Infections involving implanted medical devices cost billions of dollars a year. The development of preventative antimicrobial surfaces is considered as the most promising method to combat such infection. Surface coating materials include both metals (e.g., silver, zinc, copper, and zirconium) and non-metals (e.g., selenium and antibiotics). However, the effective use of metals such as silver is complicated by leaching and cytotoxicity issues, whereas a prolonged use of antibiotics results in reduced efficacy due to the emergence of multi-drug resistance pathogens. Surface coating with antimicrobial peptides is the best option to prevent biofilm formation. Antimicrobial peptides have the advantage of being potent against drug-resistant superbugs and will not leak into the surrounding tissues due to covalent immobilization. The antimicrobial peptides can be covalently immobilized to different surfaces ranging from plastics (e.g., polyethylene terephthalate) to metals (e.g., titanium).

In accordance with another aspect of the instant invention, medical devices or implants comprising at least one antimicrobial peptide are provided, along with methods of making the same. As used herein, the term "medical device" or "medical implant" includes devices, implants, and materials that are permanently implanted and those that are temporarily or transiently present in the patient. In a particular embodiment, at least part of the exposed surface of the medical device or implant is coated with at least one antimicrobial peptide of the instant invention. In a particular embodiment, the medical device or implant comprises a plastic (e.g., polyethylene terephthalate) or a metal (e.g., titanium). In a particular embodiment, the antimicrobial peptide is covalently attached to the surface of the medical implant or device. The antimicrobial peptide may be linked directly (e.g., via a bond) to the surface of the medical device or implant or covalently attached via a linker (e.g., a crosslinker).

The antimicrobial peptide attached to the surface of the medical device or medical implant may be any peptide having antimicrobial activity. In a particular embodiment, the antimicrobial peptide comprises one any peptide described herein (e.g., SEQ ID NOs: 1-62) or any one of the sequences specifically set forth above.

The instant invention also encompasses methods of synthesizing the coated medical device or medical implant of the instant invention. In a particular embodiment, the method comprises linking an antimicrobial peptide of the instant invention comprising a terminal cysteine to the medical device or medical implant with a sulfhydryl reactive crosslinker (e.g., a maleimide crosslinker). The crosslinker may be reacted with the antimicrobial peptide first, with the medical device or medical implant first, or with both simultaneously. In a particular embodiment, the antimicrobial peptide is linked to a biocompatible polymer (e.g., chitosan) with a sulfhydryl reactive crosslinker (e.g., a maleimide crosslinker), wherein the biocompatible polymer is attached to the medical device or medical implant.

The term "crosslinker" refers to a molecule capable of forming a covalent linkage between compounds. In a particular embodiment, the crosslinker forms a covalent linkage (e.g., a sulfide bond) via the sulfhydryl group of the terminal cysteine of the antimicrobial peptide. Crosslinkers are well known in the art. The cross-linker may be a bifunctional, trifunctional, or multifunctional crosslinking reagent. In a particular embodiment, the crosslinker is non-biodegradable or uncleavable under physiological conditions. In a particular embodiment, the crosslinker is a maleimide crosslinker.

In accordance with another aspect of the instant invention, nucleic acid molecules encoding the antimicrobial peptides are provided. Nucleic acid molecules encoding the antimicrobial peptides of the invention may be prepared by any method known in the art such as, without limitation: (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Antimicrobial peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the antimicrobial peptide nucleic acid molecules of the invention. Primers capable of specifically amplifying antimicrobial peptides encoding nucleic acids described herein are also contemplated herein. Such oligonucleotides are useful as probes and primers for detecting, isolating or amplifying antimicrobial peptide encoding nucleic acids.

The present invention also encompasses compositions comprising at least one nucleic acid encoding an antimicrobial peptide of the instant invention and at least one carrier (e.g., pharmaceutically acceptable carrier). The present invention also encompasses methods for preventing, inhibiting, and/or treating microbial infections, including microbial/bacterial biofilms. The compositions of the instant invention can be administered to an animal, in particular a mammal (e.g., a human) in order to treat, inhibit, and/or prevent a microbial (e.g., bacterial such as by *E. coli*, *S. aureus*, any the ESKAPE pathogen (including *Enterococcus faecium*, *Staphylococcus aureus*, *Klebsiella pneumoniae*, *Acinetobacter baumannii*, *Pseudomonas aeruginosa*, and *Enterobacter* species), MRSA, etc.) infection (e.g., the composition may be administered before, during, and/or after a microbial infection). The compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time or at different times (e.g., sequentially). The composition(s) comprising at least one anti-microbial peptide of the instant invention and the composition(s) comprising at least one additional antibiotic may be contained within a kit.

As stated hereinabove, the present invention also encompasses compositions comprising at least one antimicrobial peptide of the instant invention and at least one carrier (e.g., pharmaceutically acceptable carrier). The compositions comprising the antimicrobial peptides of the instant invention may be conveniently formulated for administration with any pharmaceutically acceptable carrier(s). For example, the antimicrobial peptides may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the antimicrobial peptide in the chosen medium may be varied and the medium may be chosen based on the desired route of administration of the pharmaceutical composition. Except insofar as any conventional media or agent is incompatible with the antimicrobial peptide to be administered, its use in the pharmaceutical composition is contemplated.

The present invention also encompasses methods for preventing, inhibiting, and/or treating microbial infections (e.g., viral or bacterial), particularly a bacterial infection such as *S. aureus* infections (e.g., MRSA). The method comprises administering at least one antimicrobial peptide of the instant invention (optionally within a composition with a carrier) to the subject. The method may further comprise administering at least one additional antimicrobial (e.g., antibiotic). In a particular embodiment, the microbe is an antibiotic-resistant bacteria or an ESKAPE pathogen. In a particular embodiment, the microbe is in a biofilm. In a particular embodiment, the microbe is selected from the group consisting of *Enterococcus faecium*, *Staphylococcus aureus*, *Klebsiella pneumoniae*, *Acinetobacter baumannii*, *Pseudomonas aeruginosa*, and *Enterobacter* species. The compositions of the instant invention can be administered to an animal, in particular a mammal, more particularly a human, in order to treat, inhibit, and/or prevent a microbial infection (e.g., the composition may be administered before, during, and/or after a microbial infection). The pharmaceutical compositions of the instant invention may also comprise at least one other antimicrobial agent, particularly at least one other antibiotic. The additional antimicrobial agent may also be administered in a separate composition from the antimicrobial peptides of the instant invention. The compositions may be administered at the same time and/or at different times (e.g., sequentially).

In a particular embodiment, the antimicrobial peptides of the instant invention are administered to the subject as a coating on a medical device or implant.

Bacterial infections that may be treated using the present methods include Gram-positive bacterial infections and Gram-negative bacterial infections. In a particular embodiment, the bacteria is a Gram-positive bacteria. In a particular embodiment, the bacteria is a staphylococcal strain. In yet another embodiment, the bacteria is *Staphylococcus aureus*. More particularly, the bacteria is MRSA. In a particular embodiment, the bacteria is an antibiotic-resistant bacteria or an ESKAPE pathogen. In a particular embodiment, the bacteria is selected from the group consisting of *Enterococcus faecium*, *Staphylococcus aureus*, *Klebsiella pneumoniae*, *Acinetobacter baumannii*, *Pseudomonas aeruginosa*, and *Enterobacter* species.

The antimicrobial peptides described herein will generally be administered to a patient as a pharmaceutical composition. The term "patient" as used herein refers to human or animal subjects. These antimicrobial peptides may be employed therapeutically, under the guidance of a physician.

The dose and dosage regimen of antimicrobial peptides according to the invention that are suitable for administration to a particular patient may be determined by a physician considering the patient's age, sex, weight, general medical condition, and the specific condition for which the antimicrobial peptides are being administered and the severity thereof. The physician may also take into account the route of administration, the pharmaceutical carrier, and the antimicrobial peptide's biological activity.

Selection of a suitable pharmaceutical composition will also depend upon the mode of administration chosen. For example, the antimicrobial peptides of the invention may be administered by direct injection or intravenously. In this instance, a pharmaceutical composition comprises the antimicrobial peptide dispersed in a medium that is compatible with the site of injection.

Antimicrobial peptides of the instant invention may be administered by any method. For example, the antimicrobial peptides of the instant invention can be administered, without limitation by injection, parenterally, subcutaneously, orally, nasally, topically, pulmonarily, rectally, vaginally, intravenously, intraperitoneally, intrathecally, intracerbrally, epidurally, intramuscularly, intradermally, intracarotidly, or other modes of administration such as controlled release devices. In a particular embodiment, the antimicrobial peptides are administered intramuscularly, subcutaneously, or to the bloodstream (e.g., intravenously). In a particular embodiment, the antimicrobial peptides are administered by injection. The composition may be directly administered (e.g., by injection) to the site of microbial infection. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween™ 80, polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science and Practice Of Pharmacy" by Alfonso R. Gennaro (Lippincott Williams & Wilkins) which are herein incorporated by reference. The compositions of the present invention can be prepared, for example, in liquid form, or can be in pill or dried powder form (e.g., lyophilized).

Pharmaceutical compositions for injection are known in the art. If injection is selected as a method for administering the antimicrobial peptide, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing an antimicrobial peptide of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, topical, oral, direct injection, intracranial, and intravitreal.

In yet another embodiment, the compositions of the present invention can be delivered in a controlled release system, such as using an intravenous infusion, an implantable osmotic pump, a transdermal patch, liposomes, or other modes of administration. In a particular embodiment, a pump may be used.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect (e.g., curing, relieving, treating, and/or preventing the microbial infection, the symptoms of it, or the predisposition towards it) in association with the selected pharmaceutical carrier. The dosage should not be so large as to cause adverse side effects, such as unwanted cross-reactions, anaphylactic reactions, and the like. Procedures for determining the appropriate dosage unit are well known to those skilled in the art. Generally, the dosage will vary with the age, weight, condition, sex and extent of the disease in the patient and can be determined by one of skill in the art. Appropriate concentrations for alleviation of a particular pathological condition may be determined by dosage concentration curve calculations, as known in the art. The dosage can be adjusted by the individual physician in the event of any counter indications.

In accordance with the present invention, the appropriate dosage unit for the administration of antimicrobial peptides may be determined by evaluating the toxicity of the molecules or cells in animal models. Various concentrations of antimicrobial peptides in pharmaceutical composition may be administered to mice, and the minimal and maximal dosages may be determined based on the beneficial results and side effects observed as a result of the treatment. Appropriate dosage unit may also be determined by assessing the efficacy of the antimicrobial peptide treatment in combination with other standard drugs. The dosage units of antimicrobial peptide may be determined individually or in combination with each treatment according to the effect detected.

The pharmaceutical composition comprising the antimicrobial peptides may be administered at appropriate intervals until the pathological symptoms are reduced or alleviated, after which the dosage may be reduced to a maintenance level. The appropriate interval in a particular case would normally depend on the condition of the patient. In a particular embodiment, the method comprises at least two administrations of the peptides or compositions.

The instant also encompasses delivering the antimicrobial peptides of the instant invention to a cell in vitro (e.g., in culture). The antimicrobial peptide may be delivered to the cell in at least one carrier.

The instant invention also encompasses methods for generating antimicrobial peptides, particularly antimicrobial peptides having in vivo efficacy. In a particular embodiment, the method comprises 1) identifying a peptide having inhibitory activity against a microbe; 2) increasing the hydrophobicity of the peptide (e.g., by substituting amino acids with more hydrophobic amino acids and/or adding hydrophobic amino acids to the peptide); and 3) lowering the cationicity of the peptide (e.g., by deleting cationic amino acids or substituting cationic amino acids with less or non-cationic amino acids. The methods may further comprise synthesizing the designed peptide and testing the peptide for the desired antimicrobial properties, particularly in vivo efficacy.

In one embodiment, the peptides may be obtained from the antimicrobial peptide database (aps.unmc.edu/AP/main.html). In a particular embodiment, the antimicrobial activity of the designed peptide is compared to the antimicrobial activity of the original/initial peptide. The antimicrobial activity of the modified peptides may be measured by any method, such as measuring the ability of the peptide to kill the microbe.

Definitions

The following definitions are provided to facilitate an understanding of the present invention.

The singular forms "a," "an," and "the" include plural referents unless the context clearly dictates otherwise.

The term "isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight of a given material (e.g., nucleic acid, oligonucleotide, protein, etc.). Particularly, the preparation comprises at least 75% by weight, at least 80% by weight, at least 90% by weight, or at least 95% or more by weight of the given compound. Purity may be measured by methods appropriate for the given compound (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween™ 80, polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3$^{rd}$ Ed.), American Pharmaceutical Association, Washington, 1999.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., microbial (e.g., bacterial) infection) resulting in a decrease in the probability that the subject will develop the condition.

A "therapeutically effective amount" of a compound or a pharmaceutical composition refers to an amount effective to prevent, inhibit, treat, and/or lessen the symptoms of a particular disorder or disease. The treatment of a microbial infection (e.g., a bacterial infection such as a *S. aureus* infection) herein may refer to an amount sufficient to inhibit microbial growth or kill the microbe and/or curing, relieving, and/or preventing the microbial infection, the symptom of it, or the predisposition towards it.

As used herein, the term "antibiotic" refers to antimicrobial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, the term "subject" refers to an animal, particularly a mammal, particularly a human.

The term "promoter" as used herein refers to a DNA sequence which directs transcription of a polynucleotide sequence operatively linked thereto (e.g., in a cell). The promoter may also comprise enhancer elements which stimulate transcription from the linked promoter. The term "enhancer" refers to a DNA sequence which binds to the transcription initiation complex and facilitates the initiation of transcription at the associated promoter.

A "vector" is a nucleic acid molecule such as a plasmid, cosmid, bacmid, phage, or virus, to which another genetic sequence or element (either DNA or RNA) may be attached/inserted so as to bring about the replication and/or expression of the sequence or element (e.g., under the control of a promoter contained within the vector).

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. An isolated nucleic acid (either DNA or RNA) may further represent a molecule produced directly by biological or synthetic means and separated from other components present during its production.

"Linker" refers to a chemical moiety comprising a covalent bond or a chain of atoms that covalently attach at least two compounds. The linker can be linked to any synthetically feasible position of the compounds, but preferably in such a manner as to avoid blocking the compounds desired activity. Linkers are generally known in the art. In a particular embodiment, the linker may contain from 0 (i.e., a bond) to about 50 atoms, from 0 to about 10 atoms, or from about 1 to about 5 atoms.

The term "antimicrobials" as used herein indicates a substance that kills or inhibits the growth of microorganisms such as bacteria, fungi, viruses, or protozoans, particularly bacteria.

The following examples describe illustrative methods of practicing the instant invention and are not intended to limit the scope of the invention in any way.

Example 1

Bacterial peptides have found practical applications clinically or as food preservatives (Mishra, et al. (2017) Curr. Opin. Chem. Biol., 38:87-96; Wang G, Eds. (2017) Antimicrobial Peptides: Discovery, Design and Novel Therapeutic Strategies, CABI, Oxfordshire, UK, ed. 2). To facilitate the discovery of new peptide antibiotics, the Antimicrobial Peptide Database (APD) was constructed (Wang, et al. (2016) Nucleic Acids Res., 44:D1087-93). The systematic annotation of peptides not only facilitated information retrieval and analysis but also enabled a unified peptide classification method irrespective of peptide source, activity, and 3D structure (Wang, G. (2015) Methods Mol. Biol., 1268:43-66). The APD also allowed innovative methods for identifying useful candidates with desired antimicrobial activity. One natural method was to screen the representative candidates from the database against dangerous pathogens such as human immunodeficiency virus type 1 (HIV-1) and MRSA (Wang, et al. (2010) Antimicrob. Agents Chemother., 54:1343-1346; Menousek, et al. (2012) Int. J. Antimicrob. Agents, 39:402-406). Using an ab initio approach, pathogen-specific peptides were also designed by developing a database filtering technology (DFT) (Mishra, et al. (2012) J. Am. Chem. Soc., 134:12426-12429). In this approach, thousands of database peptide sequences can pass through multiple filters (FIG. 1A), each of which rejects one unwanted feature and retains the needed parameter. A major algorithm used in that design is the most probable principle that selects the maximum in each step for peptide parameters such as length, charge, hydrophobicity, and structure. A combination of these parameters defines the peptide DFTamP1, which effectively kills gram-positive MRSA USA300 (Mishra, et al. (2012) J. Am. Chem. Soc., 134:12426-12429), a major community-associated resistant pathogen. In addition, other peptide discovery approaches have been developed based on the data from the APD (Loose, et al. (2006) Nature 443: 867-869; Torrent, et al. (2011) Angew. Chem. Int. Ed Engl., 50:10686-10689; Schmidt, et al. (2011) J. Am. Chem. Soc., 133:6720-6727).

However, there is a great gap from peptide discovery to successful implementation as an antimicrobial agent. Most of the current AMP developments focus on topical treatment (Wang, et al. (2014) ACS Chem. Biol., 9:1997-2002; de Breij, et al. (2018) Sci. Transl. Med., 10(423):eaan4044; Ge, et al. (1999) Antimicrob. Agents Chemother., 43:782-788; Cirioni, et al. (2008) Crit. Care Med., 36:2629-2633; Szabo, et al. (2010) Int. J. Antimicrob. Agents, 35:357-361; Edde, et al. (2001) Am. J. Physiol. Gastrointest. Liver Physiol., 281:G1140-50), and what determines peptide systemic in vivo efficacy is poorly understood. Serum/plasma binding may be responsible for the loss of activity in vivo for cationic AMPs (Starr, et al. (2016) ACS Chem. Biol., 11:3391-3399; Hancock, et al. (2006) Nat. Biotechnol., 24:1551-1557). Indeed, recent studies have attempted to identify cationic peptides with reduced plasma binding (de Breij, et al. (2018) Sci. Transl. Med., 10(423):eaan4044; Ge, et al. (1999) Antimicrob. Agents Chemother., 43:782-788). However, the advantage of reduced plasma binding in vivo was not shown.

Herein, peptides with efficacy in mice were identified by overcoming both in vitro and in vivo barriers (FIG. 1A). The in vitro barriers include peptide cytotoxicity, stability, effects of physiological salts, pH, and serum binding, which could compromise peptide activity (Abou Alaiwa, et al. (2014) Proc. Natl. Acad. Sci., 111:18703-18708; Wang, et al. (1998) J. Biol. Chem., 273:33115-33118). By using various sequence-modulating methods, numerous new peptides were generated based on a database designed peptide template (FIG. 1). One of the designed peptides crossed multiple in vitro barriers, allowing for the testing of this peptide in in vivo models. The in vivo evaluation of a series of peptides with a varying number of lysines (FIG. 1B) led to the discovery that the more lysines in the peptide, the more likely it will fail to reduce bacterial burden in murine models.

Materials and Methods

Peptides Property Calculations and Measurements of Hydrophobicity and Stability

All peptides were chemically synthesized and purified to >95% (Genemed Synthesis, TX). The quality of each peptide was confirmed by mass spectrometry and HPLC. Peptide molecular weight, net charge, hydrophobic content, and Boman index were calculated using the APD website (aps.unmc.edu/AP/prediction/prediction_main.php) (Wang, et al. (2009) Nucleic Acids Res., 37:D933-7; Wang, et al. (2004) Nucleic Acids Res. 32:D590-D592). Fresh stock solutions were made by solubilizing peptides in autoclaved distilled water and their concentrations were determined by UV spectroscopy (Waddell, W. J. (1956) J. Lab. Clin. Med., 48:311-314). The retention time of the peptide was measured on an HPLC system (Waters, Milford, MA) equipped with an analytical reverse-phase C18 column (4.6×250 mm) (Waters). The peptide detected at 220 nm was eluted with a gradient of acetonitrile (containing 1% TFA) from 5% to 95% at a flow rate of 1 mL/minute. Other chemicals were purchased from Sigma (St. Louis, MO) unless specified.

Protease stability of the peptides was tested in the presence of mammalian trypsin, chymotrypsin, bacterial S. aureus V8 protease and the fungal Proteinase K (Wang, et al. (2014) ACS Chem. Biol., 9:1997-2002; Mishra, et al. (2017) Acta Biomater., 49:316-328). Briefly, a solution (100 µL) of peptide/protease molar ratio, 40:1 was made in 10 mM PBS buffer (pH 8.0) and was incubated at 37° C. Aliquots (10 µL) of the reaction solutions were taken after 1, 3 and 6 days and immediately mixed with 20 µL of 2×SDS loading buffer and boiled in a water bath to stop the reaction. For the SDS gel analysis, 10 µL of each sample was loaded to the well of a 5% stacking/18% resolving tricine gel and run at a constant current of 35 mA.

Antimicrobial Activity and Hemolytic Ability.

The bacterial strains used include the Gram-positive strains *Staphylococcus aureus* USA300 LAC, *S. epidermidis* 1457, and *Bacillus subtilis* 168, as well as the Gram-negative isolates *Escherichia coli* K12 and *Acinetobacter baumannii* B2367-12. Additional, drug resistance strains include Gram-positive *Enterococcus faecium* V286-17 (VRE) and *S. aureus* M838-17 (MRSA) and Gram-negative *E. coli* E423-17, *E. coli* E416-17 (ampC), and *P. aeruginosa* E411-17. Bacteria were cultivated in tryptic soy broth (TSB) (BD Bioscience, MD).

The antibacterial activity of peptides was evaluated using a standard broth microdilution protocol with minor modifications as described (Mishra, et al. (2012) J. Am. Chem. Soc., 134:12426-12429). In brief, logarithmic phase bacterial cultures (i.e., optical density at 600 nm≈0.5) were diluted to $OD_{600}$ 0.001 and partitioned into a 96-well polystyrene microplate at 90 µL per well. After treatment with 10 µL of peptide solutions two fold diluted to various concentrations, microplates were incubated at 37° C. overnight and read on a ChroMate® 4300 Microplate Reader at 630 nm (GMI, Ramsey, MN). The minimal inhibitory concentration (MIC) is the lowest peptide concentration that fully inhibited bacterial growth. To study the influence of medium conditions on the antimicrobial activity of peptides against *S. aureus* USA300, up to 200 mM sodium chloride (NaCl), 2 mM of calcium chloride, 5-10% of human serum, mouse plasma, fluid, or supernatants of tissue homogenates were included into the assays.

Killing kinetics experiments were conducted similar to antibacterial assays described above with the following modifications. Aliquots of cultures (~$10^5$ CFU) treated with different peptides were taken at 15, 30, 50, 90, and 120 minutes, diluted 100-fold, and plated on Luria-Bertani agar plates. Colonies were counted after overnight incubation at 37° C.

Hemolytic assays of peptides were performed as described (Wang, et al. (2014) ACS Chem. Biol., 9:1997-2002). Briefly, human red blood cells (hRBCs) were washed three times with phosphate buffer saline (PBS) and diluted to a 2% solution (v/v). After peptide treatment, incubation at 37° C. for one hour, and centrifugation at 5000 rpm for 10 minutes, aliquots of the supernatant were carefully transferred to a fresh 96-well microplate. The amount of hemoglobin released was measured at 545 nm. The percent lysis was calculated by assuming 100% release when human blood cells were treated with 2% Triton™ X-100, and 0% release when incubated with PBS buffer. The peptide concentration that caused 50% lysis of hRBCs is defined as $HL_{50}$. The cell selectivity index (CSI) was calculated as the ratio between $HL_{50}$ and MIC of the corresponding peptide against a select pathogenic species.

Bacterial Membrane Permeation and Polarization

The membrane permeation experiment was performed as described with minor modifications (Wang, et al. (2005) J. Biol. Chem., 280:5803-5811). Serially diluted 10× peptides (10 µL each well) were created in 96-well microtiter plates. Propidium iodide (2 µL) at a fixed concentration of 20 µM were added to each well followed by 88 µL of the S. aureus USA300 culture (a final $OD_{600}$~0.1 in TSB media). The plate was incubated at 37° C. with continuous shaking at 100 rpm in a FLUOstar® Omega (BMG LABTECH, Cary, NC) microplate reader. The fluorescence from the plate was read every 5 minutes for a total duration of 2 hours with an excitation and emission wavelengths of 584 nm and 620 nm, respectively. Plots were made using average values of duplicated experiments with MARS software.

To view the entrance of a fluorescent dye into bacteria, confocal microscopy was also performed. A freshly inoculated S. aureus USA300 culture was grown to the exponential phase. Bacteria were then washed twice with fresh 1×PBS (pH 7.2) and the final cell density was adjusted to $1 \times 10^8$ CFU/mL. 1500 µL of the culture was added to the chambers of cuvette (Borosilicate cover glass systems, Nunc Cat. No: 155380) with peptide DFT503 or DFT533 at 12.5 µM and fluorescein isothiocyanate (FITC) at 6.25 µM. The samples were examined with a confocal laser scanning microscope (Zeiss 710) with live time series of pictures taken every 5 seconds for 5 minutes and the data were processed using the Zen 2010 software.

For bacterial membrane potential measurements, overnight culture of S. aureus USA300 was grown in TSB media to the exponential phase. Cells were then pelleted and washed with PBS twice, and re-suspended in twice the volume of PBS containing 25 mM glucose for 15 minutes at 37° C. For membrane depolarization measurements, 500 nM (final concentration) of the dye DiBAC4(3) bis-(1,3-dibutyl-barbituric acid) trimethine oxonol (ANASPEC, CA, USA) was added, and vortexed gently. Ninety microliters of the energized bacteria solution were loaded to the wells and the plate (Corning COSTAR) was immediately placed into a FLUOstar® Omega (BMG LABTECH) microplate reader. Fluorescence was read for 20 minutes at excitation and emission wavelengths of 485 nm and 520 nm, respectively, until no changes. Then 10 µL of peptide solutions was added and the fluorescence was observed for another 40 minutes. Triton™ X-100 (0.1%) was used as a positive control (Marks, et al. (2013) PLoS One, 8:e63158).

Disruption of Established Bacterial Biofilms

The antibiofilm activity of the peptide against 24 hours established biofilms was evaluated. In short, S. aureus USA300 ($10^5$ CFU/mL) was made from exponential phase bacteria in TSB media and 200 µL was distributed to each well of the microtiter plate (Corning Costar Cat No. 3595). The plates were incubated at 37° C. for 24 hours to form biofilm. Culture treated with water served as a positive control while media without bacterial inoculation served as the negative control. Media was then pipetted out and the attached biofilms were washed with 1×PBS to remove the planktonic bacteria. Each well of the plate was then filled with 20 µL of 10× peptide solution and 180 µL of fresh TSB media and the plates were further incubated at 37° C. for 24 hours. Media was then pipetted out and the wells were washed with 1×PBS to remove planktonic cells. Live cells in the biofilms were then quantitated using XTT [2,3-bis(2-methyloxy-4-nitro-5-sulfophenyl)-2H-tertazolium-5-carboxanilide] assay by following the manufacturer's instructions with modifications. 180 µL of fresh TSB and 20 µL of XTT solution was added to each well and the plates were again incubated at 37° C. for 2 hours. Absorbance at 450 nm (only media with XTT containing wells served as the blank) was obtained using a ChroMate® microtiter plate reader. Percentage biofilm growth for the peptide was plotted by assuming 100% biofilm growth is achieved on the bacterial wells without peptide treatment.

To observe live and dead bacteria in established biofilms after peptide treatment, live and dead cell staining was utilized. S. aureus USA300 ($10^5$ CFU/mL) was made from exponentially growing bacteria. Two mL was added to the chambers of cuvette (Borosilicate cover glass systems, Nunc Cat. No: 155380) and was incubated for 37° C., 24 hours for biofilm formation. Media were then pipetted out and chambers were washed with 1×PBS to remove non-adhered cells. To test the peptide effect on the preformed biofilms, 200 µL of 10× stocks of the peptide was added followed by 1800 µL of TSB. Control cuvettes contained water instead of peptide. The cuvettes were again incubated for another 24 hours at 37° C. The next day the supernatant was pipetted out and the chambers were washed with 1×PBS. The biofilms were stained with 10 µL of the LIVE/DEAD kit (Invitrogen Molecular Probes) according to the manufacturer's instructions. The samples were examined with a confocal laser scanning microscope (Zeiss 710) and the data were processed using Zen 2010 software.

Bacterial Resistance Development to the Peptide

The experiment was carried out similar to the MIC determination with a few modifications (Ge, et al. (1999) Antimicrob. Agents Chemother., 43:782-788; Ling, et al. (2015) Nature 520:388). In short, an exponential phase S. aureus USA300 culture (i.e., optical density at 600 nm≈0.5) was diluted and partitioned into a 96-well polystyrene microplate with ~$10^5$ colony forming units (CFU) per well (90 µL aliquots). After treatment with 10 µL of peptide or antibiotics solutions at various concentrations, microplates were incubated at 37° C. overnight and read on a ChroMate® 4300 Microplate Reader at 630 nm (GMI). The minimal inhibitory concentration (MIC) was defined as the lowest peptide concentration that fully inhibited bacterial growth. The wells with sub-MIC levels of the peptides that retained growth approximately half the growth of the control wells were again re-inoculated in fresh TSB with sub-MIC concertation of peptides or antibiotics to attain the exponential phase for MIC determination. Up to 15 serial passages of the bacteria cultures were done. Plots were made to determine the increase in the fold change (MIC on given passage/MIC recorded in first day of passage).

Peptide Efficacy in Mice

All animal studies were performed with local ethical committee clearance following protocols approved by the institutional animal care and use committee (IACUC #16-076-08-FC). On the study termination day, animals were euthanized humanely using $CO_2$ followed by harvesting vital organs for laboratory analysis.

To achieve the best outcome, mice were randomized and the compound identities remained unknown during the experiment. The sample size was calculated using a power analysis. Since the peptide effects were clear, 4-5 mice per group were sufficient. Animal cages (5 per cage) were kept individually in ventilated cages (IVCs) at a temperature of 20 to 24° C., humidity of 50 to 60%, 60 air exchanges per hour and a 12/12-hour light/dark cycle. Mice were fed with standardized mice food (Teklad Laboratory diet for rodents) and water (Hydropac® Alternative Watering System) from an animal's ad libitum (free feeding). All materials, including IVCs, lids, feeders, bottles, bedding, and water, were autoclaved before use. Experimental and control mice were kept in IVCs under a negative pressure and the conditions stated above. All animal manipulations were performed in a class II laminar flow biological safety cabinet.

Female C57BL/6 mice (6 weeks old) were purchased from Charles River. After environment adaptation, mice were induced neutropenic by administering two doses of cyclophosphamide on day 1 (150 mg/kg) and Day 4 (100 mg/kg). This cyclophosphamide administration was skipped for experiments using non-neutropenic mice (i.e., normal mice). On day 5, mice were infected with S. aureus USA300 LAC (~2×10$^6$ CFU per mouse) via intraperitoneal injection (i.p.). For the treatment groups, mice were i.p. treated 2 hours post infection with peptides at a single dose of 5 mg/kg. Both positive and negative controls were included. At the end of the experiments, all animals were sacrificed according to institutional guidelines. Organs, including spleen, lung, kidney, and liver, were harvested, weighed, placed in sterile PBS and stored on ice. Harvested animal organs were subsequently homogenized using homogenizer (Omni, Kennesaw, GA). Proper dilutions, especially for untreated control groups, were made to get countable colonies. Blood agar plates were then incubated overnight at 37° C. The bacteria grown on plates were enumerated and plotted using the Graph pad Prism software.

Immune Modulatory Role of the Peptide

Peptides were assayed for potential in vitro toxicity to human THP-1 cells. THP-1 monocytes were differentiated into macrophages by adding 30 ng/mL of phorbol 12-myristate 13-acetate (PMA; Sigma-Aldrich) to RPMI-1640 supplemented with 10% fetal calf serum (FBS) culture medium for 16 hours. Briefly, cells were seeded at a density of 1×10$^4$ per well in a tissue culture 96-well plate in RPMI-1640 supplemented with 10% FBS, and incubated at 37° C. in a 5% $CO_2$ atmosphere for 24 hours. Wells were replaced with serum free media and treated with peptides at different concentrations for 1 hour. After incubation, the cells were washed and incubated with 100 µL of DMEM media containing 20 µL of MTS reagent for 2 hours at 37° C. Absorbances were measured using a ChroMate® microplate reader (GMI) at 492 nm.

Cytokines released from human macrophages were also measured. THP-1 cells were differentiated into macrophages as described above and were infected at a multiplicity of infection (MOI) ratio of 10 bacteria per macrophage. The bacteria were allowed for 3 hour invasion at 37° C., 5% $CO_2$. The peptide at 4.4 µM was added into uninfected/infected culture wells and incubated for 1 hour. Post peptide incubation, the conditioned supernatants were collected and stored at −80° C. for further processing. For in vivo samples, mouse plasma was collected and stored at −80° C. as well. Using cytokine ELISA kits, chemokines in THP-1 cells or mouse plasma were quantified by following the manufacturer's instructions (Invitrogen, Carslbad, CA).

Structural Basis of Membrane Targeting and Cell Selectivity

Because of the difficulty in crystallizing membrane bound peptides, two-dimensional solution nuclear magnetic resonance (2D NMR) spectroscopy was used (Wuthrich, K. (1986) NMR of Proteins and Nucleic Acids, John Wiley & Sons, New York). For NMR measurements, DFT503 (2 mM) was solubilized in 0.3 ml of aqueous solution of 90% $H_2O$ and 10% $D_2O$ containing deuterated sodium dodecylsulfate (SDS) at pH 5.5. The peptide/SDS molar ratio was 1:61. The pH of each sample was adjusted and measured directly in the 5-mm NMR tube with a micro-pH electrode (Wilmad-Labglass). All proton NMR data (NOESY, TOCSY and DQF-COSY) were collected using a spectral width of 8,000 Hz in both dimensions at 25° C. on a Bruker 600 MHz NMR spectrometer equipped with a triple-resonance cryoprobe. The water signal was suppressed by low power presaturation during the relaxation delay in NOESY, TOCSY and DQF-COSY experiments. To obtain backbone $^{15}N$, $^{13}C\alpha$, and $^{13}C\beta$ chemical shifts, natural abundance HSQC spectra were recorded. All NMR data were processed on an Octane workstation using the NMRPipe software (Delaglio, et al. (1995) J. Biomol. NMR, 6:277-293). NMR data were apodized by a 630 shifted squared sine-bell window function in both dimensions, zero-filled prior to Fourier transformation to yield a data matrix of 2,048×1,024. NMR data were analyzed with PIPP (Garrett, et al. (2011) J. Magn. Reson., 213:357-363). The peptide proton signals were assigned using the standard procedure (Wuthrich, K. (1986) NMR of Proteins and Nucleic Acids, John Wiley & Sons, New York) and validated using $^{15}N$ and $^{13}C$ chemical shifts of the peptides (Wang, et al. (2005) J. Biol. Chem., 280:5803-5811).

The 3D structure of DFT503 was determined based on both distance and angle restraints by using the NIH-Xplor program (Schwieters, et al. (2003) J. Magn. Reson., 160: 65-73). The distance restraints were obtained by classifying the nuclear Overhauser enhanced (NOE) cross peak volumes into strong (1.8-2.8 Å), medium (1.8-3.8 Å), weak (1.8-5.0 Å), and very weak (1.8-6.0 Å) ranges. Peptide backbone angle restraints were predicted based on backbone $^1H\alpha$, $^{13}C\alpha$, $^{13}C\beta$, and $^{15}N$ chemical shifts (Cornilescu, et al. (1999) J. Biomol. NMR, 13:289-302). In total, 100 structures were calculated. An ensemble of 20 structures with the lowest total energy was chosen. This final ensemble of the accepted structures satisfies the following criteria: no distance violations greater than 0.30 Å, root mean squared deviations (rmsd) for bonds from the ideal less than 0.01 Å, and rmsd for angles from the ideal less than 5°.

Statistical Analysis

Experiments were replicated and repeated. The results were represented as mean+standard deviation. However, MIC values were reported as a range, indicating the maximal and minimal concentrations needed to fully inhibit the growth of pathogens. For in vivo studies, the bacterial loads from mouse tissues were plotted as individual points and error bars represent the deviations from the average within the experimental group. * $P<0.05$,  $P<0.01$, *$P<0.001$ and n.s. represents no significance (determined by Mann-Whitney test).

Results
Peptide Optimization and In Vitro Testing

Peptides that display in vivo efficacy in a systemic mouse model were sought (outlined in FIG. 1A). There are multiple hurdles one must overcome toward the development of novel peptide antibiotics. One of them is peptide cytotoxicity. To minimize hemolysis of the peptide template DFTamP1, its amino acid sequence (FIG. 1B) was altered in three manners (sequences and properties of new peptides in Table 1). First, a single alanine was used to substitute each of the eight leucines. The resulting analogs DFT506-DFT513 retained high antimicrobial activity against *S. aureus* USA300 with a minimal inhibitory concentration (MIC) ranging from 0.78 to 1.56 µM (Table 2). Two variants, DFT507 (L3A) and DFT510 (L8A), were found to have the same antibacterial activity spectrum against *S. aureus* as the original peptide DFTamP1. Other alanine-substituted analogs showed good activity against gram-negative *Escherichia coli* and *Klebsiella pneumoniae*. In addition, DFT506 and DFT511 were also active against *Pseudomonas aeruginosa* PAO1. Interestingly, the double alanine substitution analogs DFT514-DFT516 (L5A and L8A) were only active against *S. aureus, E. coli* and *K. pneumoniae* (Table 2). They were also less hemolytic to human red blood cells (hRBCs). Triple substituted analogs (DFT521, DFT528, and DFT529) of DFTamP1 only retained moderate activity (MIC 12.5-25 µM) against *S. aureus*. Finally, quadruple alanine substitution led to inactive peptides DFT522 and DFT530 at 25 µM (Table 2). These results indicate the limitation of the alanine scanning method for obtaining highly selective peptides.

TABLE 1

Physical parameters of new peptides designed based on the template DFTamP1.

| Peptide | Sequence | Net Charge | pho % | WWH | GRAVY | Boman Index (kcal/mol) | HM (µH) |
|---|---|---|---|---|---|---|---|
| 1. Alanine substitution | | | | | | | |
| Single alanine substitution | | | | | | | |
| DFTamP1 | GLLSLLSLLGKLL (SEQ ID NO: 1) | 1 | 61 | -3.21 | 1.8 | -2.22 | 0.576 |
| DFT506 | GALSLLSLLGKLL (SEQ ID NO: 2) | 1 | 61 | -2.48 | 1.7 | -1.98 | 0.473 |
| DFT507 | GLASLLSLLGKLL (SEQ ID NO: 3) | 1 | 61 | -2.48 | 1.7 | -1.98 | 0.628 |
| DFT508 | GLLSALSLLGKLL (SEQ ID NO: 4) | 1 | 61 | -2.48 | 1.7 | -1.98 | 0.507 |
| DFT509 | GLLSLASLLGKLL (SEQ ID NO: 5) | 1 | 61 | -2.48 | 1.7 | -1.98 | 0.521 |
| DFT510 | GLLSLLSALGKLL (SEQ ID NO: 6) | 1 | 61 | -2.48 | 1.7 | -1.98 | 0.614 |
| DFT511 | GLLSLLSLAGKLL (SEQ ID NO: 7) | 1 | 61 | -2.48 | 1.7 | -1.98 | 0.470 |
| DFT512 | GLLSLLSLLGKAL (SEQ ID NO: 8) | 1 | 61 | -2.48 | 1.7 | -1.98 | 0.541 |
| DFT513 | GLLSLLSLLGKLA (SEQ ID NO: 9) | 1 | 61 | -2.48 | 1.7 | -1.98 | 0.492 |
| Double alanine substitution | | | | | | | |
| DFT514 | GLLSALKALGKLL (SEQ ID NO: 10) | 2 | 61 | -0.89 | 1.30 | -1.57 | 0.614 |
| DFT515 | GLLSALOALGKLL (SEQ ID NO: 11) | 2 | 61 | -0.89 | 1.30 | -1.57 | 0.614 |
| DFT516 | GLLSALOALGOLL (SEQ ID NO: 12) | 2 | 61 | -0.89 | 1.30 | -1.57 | 0.614 |
| Triple alanine substitution | | | | | | | |
| DFT521 | GLLSALKAAGKLL (SEQ ID NO: 13) | 2 | 61 | -0.16 | 1.15 | -1.33 | 0.515 |
| DFT528 | GALSALKALGKLL (SEQ ID NO: 14) | 2 | 61 | -0.16 | 1.15 | -1.33 | 0.507 |
| DFT529 | GLLSALKALGKAL (SEQ ID NO: 15) | 2 | 61 | -0.16 | 1.15 | -1.33 | 0.604 |

TABLE 1-continued

Physical parameters of new peptides designed based on the template DFTamP1.

| Peptide | Sequence | Net Charge | pho % | WWH | GRAVY | Boman Index (kcal/mol) | HM (µH) |
|---|---|---|---|---|---|---|---|
| Quadruple alanine substitution | | | | | | | |
| DFT522 | GLLSAAKAAGKLL (SEQ ID NO: 16) | 2 | 61 | 0.57 | 1.0 | -1.09 | 0.433 |
| DFT530 | GALSALKALGKAL (SEQ ID NO: 17) | 2 | 61 | 0.57 | 1.0 | -1.09 | 0.499 |
| 2. Sequence deletion | | | | | | | |
| DFT523 | GLLSL-SLLGKLL (SEQ ID NO: 18) | 1 | 58 | -2.65 | 1.69 | -1.99 | 0.266 |
| DFT524 | GLLSL-SL-GKLL (SEQ ID NO: 19) | 1 | 54 | -2.09 | 1.5 | -1.73 | 0.325 |
| DFT525 | GLLS--SL-GKLL (SEQ ID NO: 20) | 1 | 50 | -1.53 | 1.27 | -1.41 | 0.699 |
| DFT526 | GL-S--SL-GKLL (SEQ ID NO: 21) | 1 | 44 | -0.97 | 0.98 | -1.02 | 0.651 |
| 3. Local sequence shuffling | | | | | | | |
| DFT502 | GLSLLLSLLGKLL (SEQ ID NO: 22) | 1 | 61 | -3.2 | 1.85 | -2.2 | 0.557 |
| DFT503 | GLSLLLSLGLKLL (SEQ ID NO: 23) | 1 | 61 | -3.2 | 1.85 | -2.2 | 0.385 |
| DFT504 | GLSLLLSLLLGKL (SEQ ID NO: 24) | 1 | 61 | -3.2 | 1.85 | -2.2 | 0.366 |
| DFT505 | GLLSSLLLLGKLL (SEQ ID NO: 25) | 1 | 61 | -3.2 | 1.85 | -2.2 | 0.394 |
| DFT527 | GKLLSLLSLLGLL (SEQ ID NO: 26) | 1 | 61 | -3.2 | 1.85 | -2.2 | 0.267 |
| DFT531 | GLLSLLSLGLKLL (SEQ ID NO: 27) | 1 | 61 | -3.2 | 1.85 | -2.2 | 0.459 |
| DFT532 | LLGSLLSLGLKLL (SEQ ID NO: 28) | 1 | 61 | -3.2 | 1.85 | -2.2 | 0.511 | pho %, hydrophobic percent;
O, ornithine;
WWH, Wimley-White whole-residue hydrophobicity (i.e. the sum of whole-residue free energy of transfer of the peptide from water to POPC interface) (Wimley, et al. (1996) Nat. Struct. Biol., 3:842-848);
GRAVY, the grand average hydropathy value of the peptide (Kyte, et al. (1982) J. Mol. Biol., 157:105-132);
HM, hydrophobic moment (Eisenberg, et al. (1982) Nature 299:371-374).

TABLE 2

Minimal inhibitory concentrations of alanine substituted peptides. All peptides are amidated at their carboxyl termini and quantified by UV.

| Peptide | MIC (µM) | | | | |
|---|---|---|---|---|---|
| | S. aureus USA 300 | P. aeruginosa PAO1 | E. coli ATCC 25922 | K. pneumoniae | $HL_{50}$[b] |
| DFTamP1 | 0.78 | >25 | >25 | >25 | <3.1 |
| DFT506 | 0.78 | 12.5 | 3.1 | 6.2 | 4 |
| DFT507 | 0.78 | >25 | >25 | >25 | <3.1 |
| DFT508 | 0.78 | >25 | 3.1 | 3.1 | 6 |
| DFT509 | 0.78 | 6.2-12.5 | 1.5-3.1 | 3.1 | 4 |
| DFT510 | 1.56 | >25 | >25 | >25 | 19 |
| DF1511 | 0.78 | 12.5 | 3.1 | 3.1 | 14 |
| DFT512 | 0.78 | >25 | 3.1 | 3.1 | 4 |
| DFT513 | 1.56 | >25 | 1.5-3.1 | 12.5-25 | <3.1 |
| DF1514 | 1.56 | >25 | 3.1 | 3.1 | 36 |
| DFT515 | 1.56 | >25 | 3.1 | 3.1 | 36 |
| DFT516 | 1.56 | >25 | 3.1-6.25 | 3.1 | 36 |

TABLE 2-continued

Minimal inhibitory concentrations of alanine substituted peptides. All peptides are amidated at their carboxyl termini and quantified by UV.

| | MIC (µM) | | | | |
|---|---|---|---|---|---|
| Peptide | S. aureus USA 300 | P. aeruginosa PAO1 | E. coli ATCC 25922 | K. pneumoniae | HL$_{50}$[b] |
| DFT521 | 12.5 | >25 | 12.5 | ND [c] | >50 |
| DFT528 | 25 | >25 | 25 | >25 | >50 |
| DFT529 | 75 | >25 | 25 | >25 | >50 |
| DF1522 | >25 | >25 | >25 | ND | 50 |
| DFT530 | >25 | >25 | >25 | >25 | >100 |

[b] HL$_{50}$ is the hemolytic concentration of the peptide that causes the lysis of 50% hRBCs (2% v/v).
[c] ND, not determined.

As a second approach, single amino acid deletions were applied to DFTamP1. When L6 was removed, the peptide DFT523 retained moderate activity (12.5-25 µM) against *S. aureus* and *E. coli*. Further removal of one more leucines from the sequence led to inactive peptides (DFT524-DFT526, Table 3). Third, interesting peptides emerged when the sequence of DFTamP1 was shuffled, i.e. altering amino acid order without a change of peptide composition. To avoid a loss of antimicrobial activity from random shuffling, a local sequence shuffling was conducted to generate sequences unexplored in previous peptide designs. For instance, a less common LLL motif was introduced into the peptide DFT503 (LL was identified in 704 AMPs in the APD whereas LLL was found only in 21 AMPs). Remarkably, DFT503 became much less hemolytic than DFTamP1 (Table 4). Meanwhile, all the peptides in this category retained the same activity spectrum as DFTamP1, which is primarily active against *S. aureus* (MIC 0.78-6.25 µM), but not *P. aeruginosa*, *E. coli*, and *K. pneumoniae*. Of note, DFT504 (MIC 6.2 µM) was four times less active than the DFTamP1 (Table 4).

TABLE 3

Minimal inhibitory concentrations of amino acid deleted peptides of DFTamP1. Peptides were quantified by UV.

| | MIC (µM) | | | | |
|---|---|---|---|---|---|
| Peptide | S. aureus USA300 | P. aeruginosa PAO1 | E. coli ATCC 25922 | K. pneumonia ATCC 13883 | HL$_{50}$[b] |
| DFTamP1 | 0.78 | >25 | >25 | >25 | <3.1 |
| DFT523 | 12.5 | >25 | 25 | ND [c] | >50 |
| DFT524 | >25 | >25 | >25 | >25 | >300 |
| DF1525 | >25 | >25 | >25 | >25 | >300 |
| DFT526 | >25 | >25 | >25 | >25 | >300 |

[b] HL$_{50}$ is the peptide concentration required to lyse 50% of human red blood cells (hRBCs; 2%, v/v).
[c] ND; not determined.

TABLE 4

Sequence shuffled and charge-increased peptides (MIC, µM). Peptides in this table were quantitated based on weight.

| Peptide | Sequence | SA[2] | PA | EC | KP | HL$_{50}$ | CSI | t$^{RP}$ | HMo | K# |
|---|---|---|---|---|---|---|---|---|---|---|
| Local sequence-shuffled peptides based on DFTamP1 | | | | | | | | | | |
| DFTamP1 | GLLSLLSLLGKLL (SEQ ID NO: 1) | 3.1 | >25 | >25 | >25 | 10 | | 3.2 | 16.58 | 0.58 | 1 |
| DFT502 | GLSLLLSLLGKLL (SEQ ID NO: 22) | 1.6 | >25 | >25 | >25 | 3.1 | | 2.0 | 15.49 | 0.56 | 1 |
| DFT503 | GLSLLLSLGLKLL (SEQ ID NO: 23) | 1.6 | >25 | >25 | >25 | >300 | >192 | | 14.45 | 0.39 | 1 |
| DFT503d | GLSLLLSLGLKLL (SEQ ID NO: 23) | 1.6 | >25 | >25 | >25 | >300 | >192 | | 14.45 | | 1 |
| DFT504 | GLSLLLSLLLGKL (SEQ ID NO: 24) | 6.2 | >25 | >25 | >25 | 8 | | 1.3 | 14.12 | 0.37 | 1 |
| DFT505 | GLLSSLLLLGKLL (SEQ ID NO: 25) | 3.1 | >25 | >25 | >25 | 20 | | 6.5 | 14.87 | 0.39 | 1 |
| DFT527 | GKLLSLLSLLGLL (SEQ ID NO: 26) | 3.1 | >25 | >25 | >25 | 20 | | 6.5 | 14.56 | 0.27 | 1 |
| DFT531 | GLLSLLSLGLKLL (SEQ ID NO: 27) | 0.8 | >25 | >25 | >25 | 7 | | 9.0 | 15.85 | 0.46 | 1 |
| DFT532 | LLGSLLSLGLKLL (SEQ ID NO: 28) | 1.6 | >25 | >25 | >25 | 13 | | 8.3 | 14.22 | 0.51 | 1 |

TABLE 4-continued

Sequence shuffled and charge-increased peptides (MIC, μM).
Peptides in this table were quantitated based on weight.

| Peptide | Sequence | SA[2] | PA | EC | KP | HL$_{50}$ | CSI | t$^{RP}$ | HMo | K# |
|---|---|---|---|---|---|---|---|---|---|---|
| Charged-increased peptides based on DFT503 | | | | | | | | | | |
| DFT503 | GLSLLLSLGLKLL (SEQ ID NO: 23) | 1.6 | >25 | >25 | >25 | >300 | >192 | 14.46 | 0.39 | 1 |
| DFT560 | KLSLLLSLGLKLL (SEQ ID NO: 29) | 1.6 | >25 | >25 | >25 | 25 | 16 | 13.21 | 0.38 | 2 |
| DFT561 | GLKLLLSLGLKLL (SEQ ID NO: 30) | 1.6 | >25 | >25 | >25 | >300 | >192 | 13.56 | 0.43 | 2 |
| DFT561d | GLKLLLSLGLKLL (SEQ ID NO: 30) | 1.6-3.1 | >25 | >25 | >25 | >300 | >192 | | | 2 |
| DFT562 | GLSLLKLGLKLL (SEQ ID NO: 31) | 0.8-1.6 | >25 | >25 | >25 | <25 | <16 | 13.62 | 0.46 | 2 |
| DFT563 | GLSLLLSLKLKLL (SEQ ID NO: 32) | 6.2 | >25 | >25 | >25 | >300 | >48 | 11.94 | 0.31 | 2 |
| DFT564 | GLKLLLKLGLKLL (SEQ ID NO: 33) | 0.8-1.6 | >25 | >25 | >25 | <25 | <16 | 12.89 | 0.50 | 3 |
| DFT565 | KLKLLLKLGLKLL (SEQ ID NO: 34) | 0.8 | >25 | >25 | >25 | 50 | 64 | 11.75 | 0.48 | 4 |

SA, *S. aureus* USA300;
PA, *P. aeruginosa* PAO1;
EC; *E. coli* ATCC 25922;
KP, *K. pneumonia* ATCC13883;
HL$_{50}$, the peptide concentration for 50% hemolysis;
CSI, cell selectivity index;
t$^{RP}$, retention time on a reverse-phase HPLC;
HMo, hydrophobic moment calculated based on the web tool heliquest.ipmc.cnrs.fr;
K#, the number of lysines in the sequence.

Figure 2:
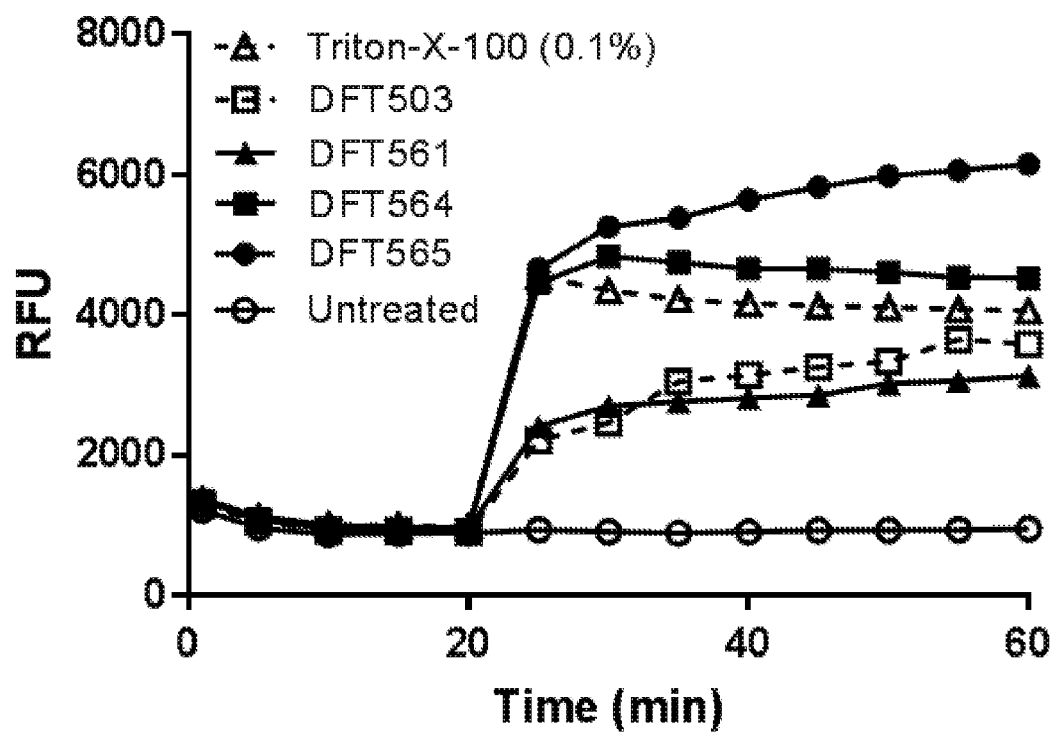

In addition, there are other factors (pH, salts, and serum) that compromise peptide activity (de Breij, et al. (2018) Sci. Transl. Med., 10 (423): eaan4044; Ge, et al. (1999) Antimicrob. Agents Chemother., 43:782-788; Hancock, et al. (2006) Nat. Biotechnol., 24:1551-1557). The activity of defensins is usually salt-sensitive (Abou, et al. (2014) Proc. Natl. Acad. Sci., 111:18703-18708), while human cathelicidin LL-37 becomes less active at pH 6.8 or after binding to human serum (Abou, et al. (2014) Proc. Natl. Acad. Sci., 111:18703-18708; Wang, et al. (1998) J. Biol. Chem., 273: 33115-33118). Encouragingly, antibacterial activity of DFT503 and its D-form (DFT503d) was not significantly affected by salts (1-2 mM Ca$^{2+}$ or 50-200 mM NaCl) (Tables 5 and 6). However, their MIC values increased over eight fold in a medium containing a physiological amount (5%) of human serum or 5% mouse plasma (Table 5). To search for peptides that can tolerate serum/plasma, a single serine or glycine was substituted in DFT503 with lysine (Table 4). The substitution of S3 of DFT503 by K3 increased peptide solubility. Antimicrobial assays revealed that DFT561 maintained the same activity spectrum as DFTamP1. Importantly, the peptide did not become more hemolytic. The positional effect of one additional lysine on peptide properties was also studied. While DFT560, DFT562, and DFT563 all showed high antimicrobial potency, they were more hemolytic as well. When additional basic amino acids were incorporated, peptides DFT564 and DFT565 (with three and four lysines) became even more hemolytic than DFT503. Thus, additional positively charged lysines did not offer an advantage to the peptide in terms of cytotoxicity, despite increased membrane depolarization of *S. aureus* (FIG. 2)

TABLE 5

Effects of pH, salt and serum/plasma on peptide activity against *S. aureus* USA300. Peptides in this table were quantitated based on weight.

| | MIC (μM) | | | | | |
|---|---|---|---|---|---|---|
| Peptide | pH 6.8 | pH 7.4 | pH 8.0 | NaCl (150 mM) | Human serum (5%) | Murine plasma (5%) |
| DFTamP1 | 6.2 | 3.1 | 3.1 | 3.1-6.2 | 12.5 | 6.2 [2] |
| DFT503 | 3.1 | 3.1-6.2 | 3.1 | 3.1 | >25 | >25 |
| DFT503d | 3.1 | 3.1 | 1.6 | 3.1 | >25 | >25 |
| DFT561 | 3.1 | 1.6 | 1.6 | 1.6 | 3.1 | 3.1-6.2 |
| DFT561d | 3.1 | 1.6 | 1.6 | 3.1 | >25 | 12.5 |
| DFT564 | 1.6 | 3.1 | 1.6 | 3.1 | 3.1 | 12.5 |
| DFT565 | 3.1-6.2 | 3.1 | 3.1 | 3.1 | 6.2 | >25 |

[2] Two-fold MIC change with and without murine plasma.

TABLE 6

Effects of physiologically relevant salts $Ca^{2+}$ and NaCl on antimicrobial activity of DFTamP1 and analogs against S. aureus USA300. Peptides were quantified by UV.

| | MIC (µM) | | | | | |
|---|---|---|---|---|---|---|
| Peptide | No salts added | 1 mM $Ca^{2+}$ | 2 mM $Ca^{2+}$ | 50 mM NaCl | 100 mM NaCl | 200 mM NaCl |
| DFTamP1 | 0.78 | 0.78 | 0.78-1.56 | 0.78 | 0.78 | 0.78 |
| DFT503 | 1.56 | 1.56 | 1.56 | 1.56-3.1 | 1.56-3.1 | 3.1 |
| DFT503d | 1.56 | 1.56 | 1.56 | 1.56 | 1.56 | 1.56 |

The antimicrobial activity of these peptides was then compared in the presence of serum. Remarkably, DFT561 inhibited S. aureus USA300 in the presence of 5% human serum or mouse plasma (Table 5). Thus, DFT561 emerged as a more robust antimicrobial candidate with an excellent therapeutic potential (high potency, low hemolysis, and robust activity). Next, peptide stability against proteases was tested. Since a peptide made of D-amino acid is usually more stable (Wade, et al. (1990) Proc. Natl. Acad. Sci., 87:4761-4765; Mishra, et al. (2012) J. Am. Chem. Soc., 134:12426-12429; Ge, et al. (1999) Antimicrob. Agents Chemother., 43:782-788; Cirioni, et al. (2008) Crit. Care Med., 36:2629-2633), the D-form of DFT561 (DFT561d) was made. Interestingly, both forms of the DFT561 peptides retained bacterial killing in the presence of mouse peritoneal cavity fluid or homogenized tissue supernatants from uninfected mice (FIG. 3A).

To further evaluate peptide potency, resistant bacterial strains, biofilms, and persisters were tested. DFT503, DFT561, and their D-forms showed potent activity against gram-positive MRSA and vancomycin-resistant enterococci (VRE) strains, but not multi-resistant gram-negative E. coli, P. aeruginosa and K. pneumoniae (Table 7). DFT561d appeared more potent than DFT561 in disrupting a 24 hour formed static biofilms of S. aureus USA300. At 25 µM, DFT561d essentially eliminated bacterial burden in the biofilms, while DFT561 killed 60% S. aureus (FIG. 3B). Because of the anti-biofilm potency of DFT561d, its effects on other forms of S. aureus were tested. It was able to rapidly kill S. aureus in exponential (FIG. 4) and stationary phases (FIG. 3C), as well as persisters that were not killed by traditional antibiotics (FIG. 3D). These results further validated the potency of DFT561d.

In Vivo Toxicity and Efficacy of Cationic Peptides in a Neutropenic Mouse Model

Figure 5:
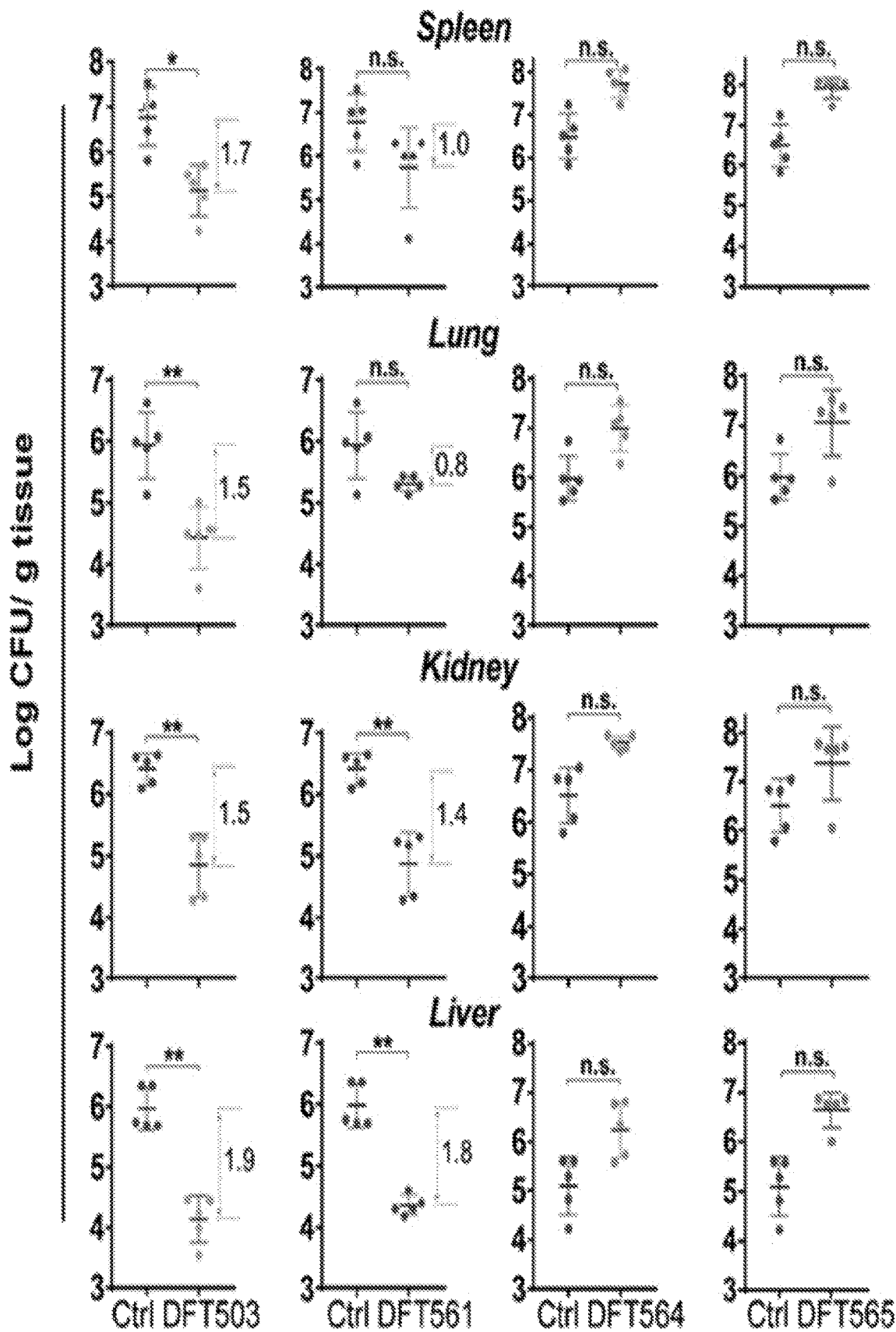

Because DFT561 had crossed multiple in vitro barriers (Table 5), its in vivo toxicity and efficacy was tested. A well-established neutropenic mouse model was used, which is often utilized to evaluate the efficacy of antibiotics and peptide mimics (Ambrose, et al. (2012) Clin. Infect. Dis., 54(3):S220-8; Radzishevsky, et al. (2007) Nat. Biotechnol., 25:657-659). In this model, the effect of immune cells on bacterial killing is minimized via two injections of cyclophosphamide before infection (FIG. 5). To evaluate the safety of the peptide in vivo, the toxicity of DFT561 injected intraperitoneally (i.p.) was compared at 10, 20, and 40 mg/kg per mouse. Mice injected at 10 mg/kg behaved normal, but those treated at 20 or 40 mg/kg showed reduced activity for 30 minutes. Small weight losses for all the treatment groups was observed, but the changes were statistically insignificant. In addition, alanine transaminase normally resides in serum and tissues but can be released after liver injury. Differences in a quantitative alanine transaminase assay of liver homogenates from mice treated at 0, 10, and 20 mg/kg was not observed. All these results indicate that DFT561 is not toxic when treated at 5 mg/kg.

Figure 6:
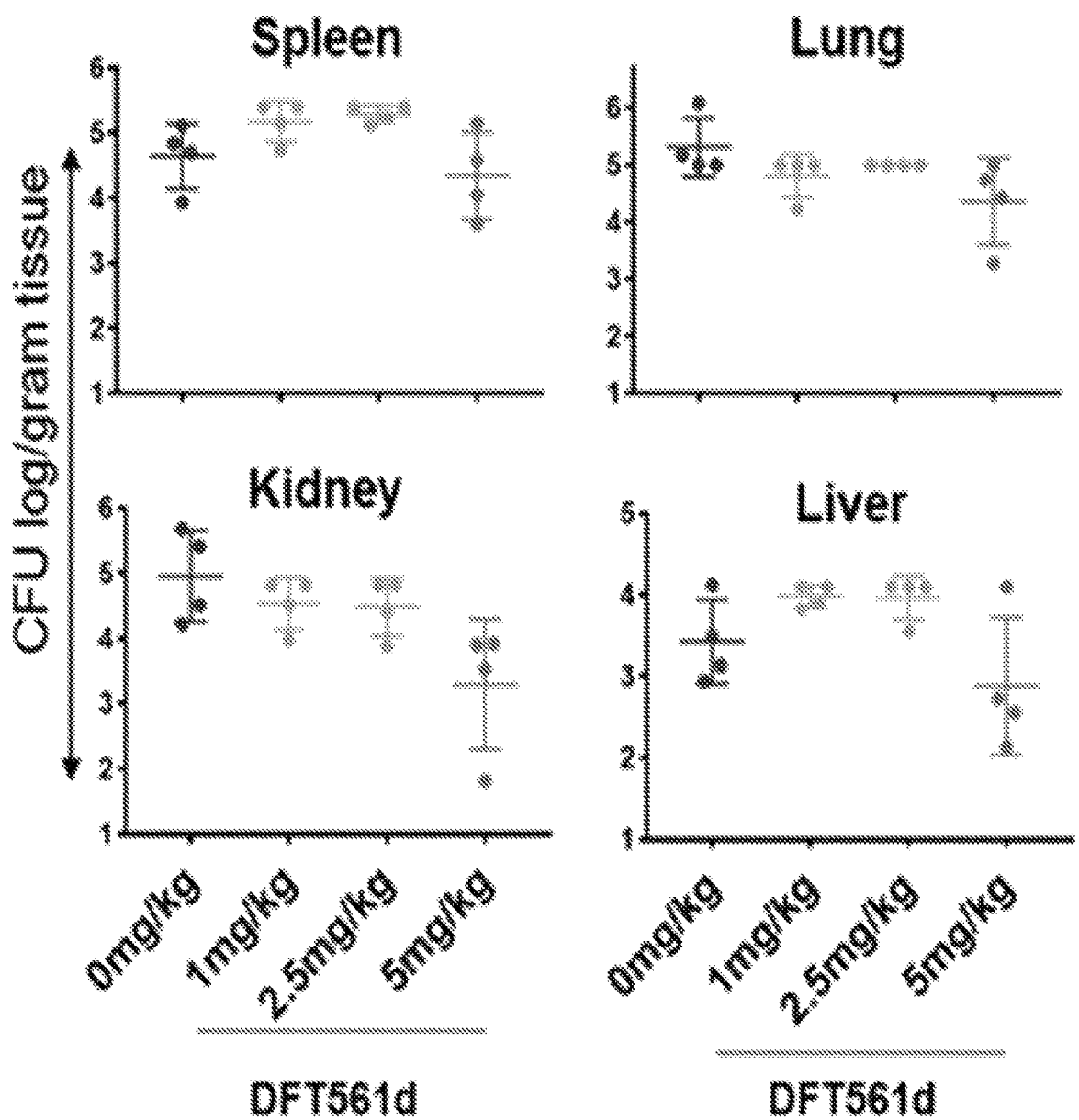

In the in vivo efficacy study, each mouse was i.p. infected with $2 \times 10^6$ colony forming units (CFU) of S. aureus USA300 LAC (FIG. 5). As a positive control, 1-4 logs decrease in bacterial burden was observed in different tissues after daptomycin treatment via a single i.p. injection. In contrast, a decrease in bacterial burden in tissues was not observed when the infected mice were treated with an LL-37 derived analog. The infected mice were then treated with DFT561 at a single dose of 5 mg/kg since it is less affected by serum/plasma binding (Table 5). The 5 mg/kg dose was chosen based on a dose-dependent study (FIG. 6). The peptide treatment was initiated at 2 hours post infection when bacteria had spread to various tissues, indicating a systemic infection. At 24 hours after treatment, bacterial burdens in spleen, lung, liver, and kidney with and without peptide treatment were enumerated. On average, a bacterial load decrease by 1.8 logs was observed in liver and 1.4 logs in kidney (up to 90% killing). There were also decreased bacterial loads in spleen and lung, but the differences were statistically insignificant compared to the untreated controls (FIG. 5).

DFT561d was also evaluated since it is resistant to proteases. Interestingly, DFT561 and DFT561d displayed a similar in vivo effect (FIG. 7), although DFT561d showed a

TABLE 7

In vitro activity of database designed peptides against resistant pathogens. Peptides were quantitated based on weight.

| | MIC (µM) | | | | | |
|---|---|---|---|---|---|---|
| Peptide/ antibiotic | S. aureus M838-17 (MRSA) | E. faecium V286-17 (VRE) | P. aeruginosa E411-17 | K. pneumoniae E406-17 | E. coli ampC E416-7 | E. coli E423-17 |
| DFT503 | 3.1 | 3.1-6.25 | >50 | >50 | >50 | >50 |
| DFT503d | 3.1 | 3.1-6.25 | >50 | >50 | >50 | >50 |
| DFT561 | 3.1 | 3.1-6.25 | >50 | >50 | >50 | >50 |
| DFT561d | 3.1 | 3.1-6.25 | >50 | >50 | >50 | >50 |
| Daptomycin | 0.78 | 3.1 | ND [b] | ND | ND | ND |
| Vancomycin | 0.78 | ≥12.5 | ND | ND | ND | ND |
| Rifamycin | 1.56 | 12.5 | ND | ND | ND | ND |
| Nafcillin | 0.78-1.56 | >12.5 | ND | ND | ND | ND |

Figure 7:
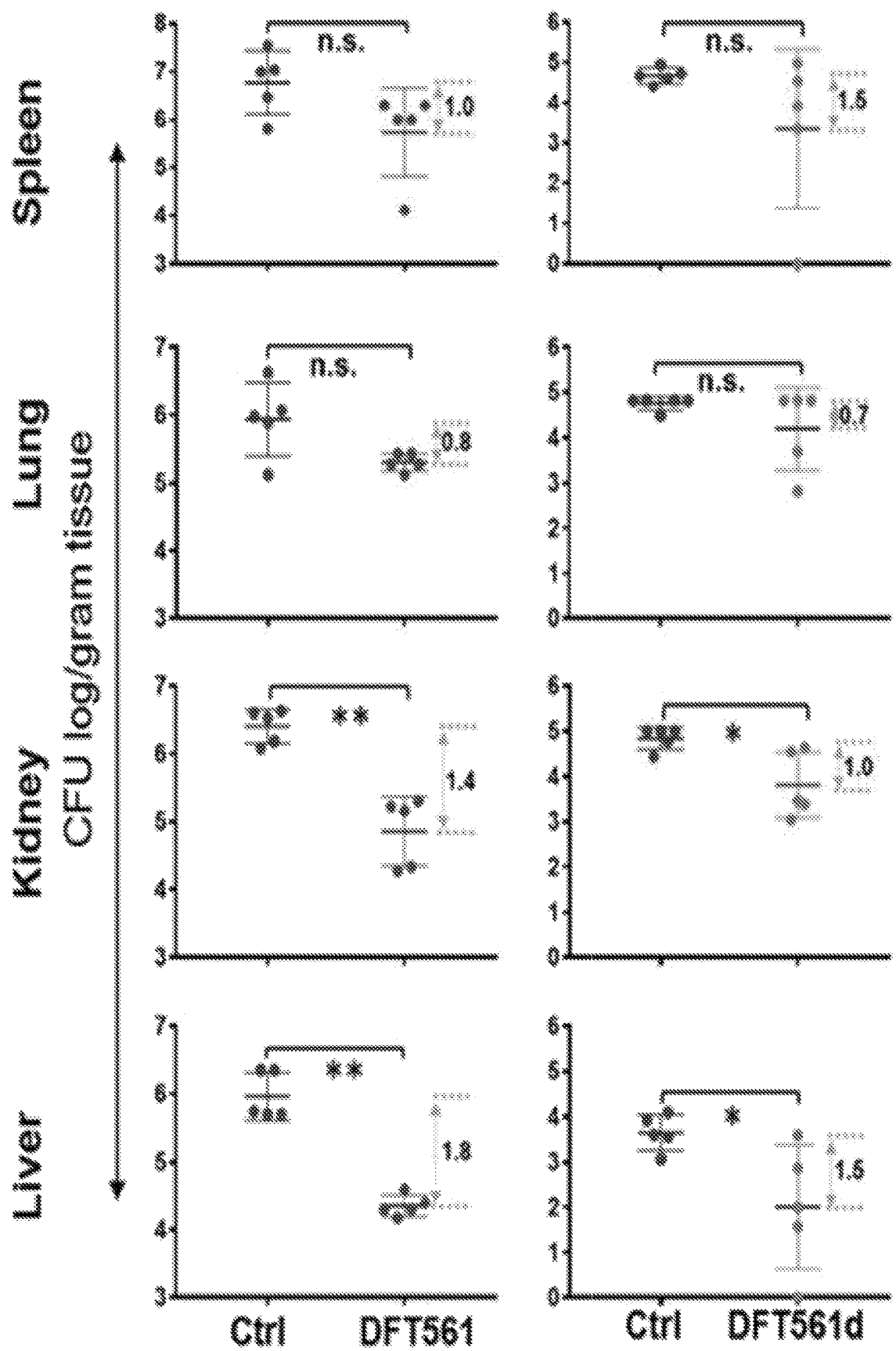

[b] ND = not determined.

much reduced antibacterial activity in vitro in the presence of human serum or murine plasma (Table 5). Serum/plasma binding may not be a limiting factor for in vivo efficacy of these peptides in this mouse model when intraperitoneally administered. To test this possibility, the in vivo study was expanded to DFT503, which is inactive in the presence of serum/plasma (Table 5). Compared to DFT561, a similar in vivo efficacy for DFT503 was observed in kidney and liver, but a slightly better efficacy in spleen and lung (FIG. 5). Thus, the data indicates that serum binding plays a less important role for in vivo efficacy of these peptides. Likewise, peptide stability may not be critical here based on the similar in vivo effects of the L- and D-forms of D561 when injected intraperitoneally (FIG. 7).

It was then determined whether a further increase in basic lysine could influence peptide in vivo efficacy. For this purpose, DFT564 and DFT565 (FIG. 1B) were evaluated. Surprisingly, while a DFT503 analog with one lysine worked, DFT564 and DFT565 with three to four lysines were entirely inactive (FIG. 5), underscoring a high number of positively charged lysines is not favorable for in vivo efficacy.

Figure 8:
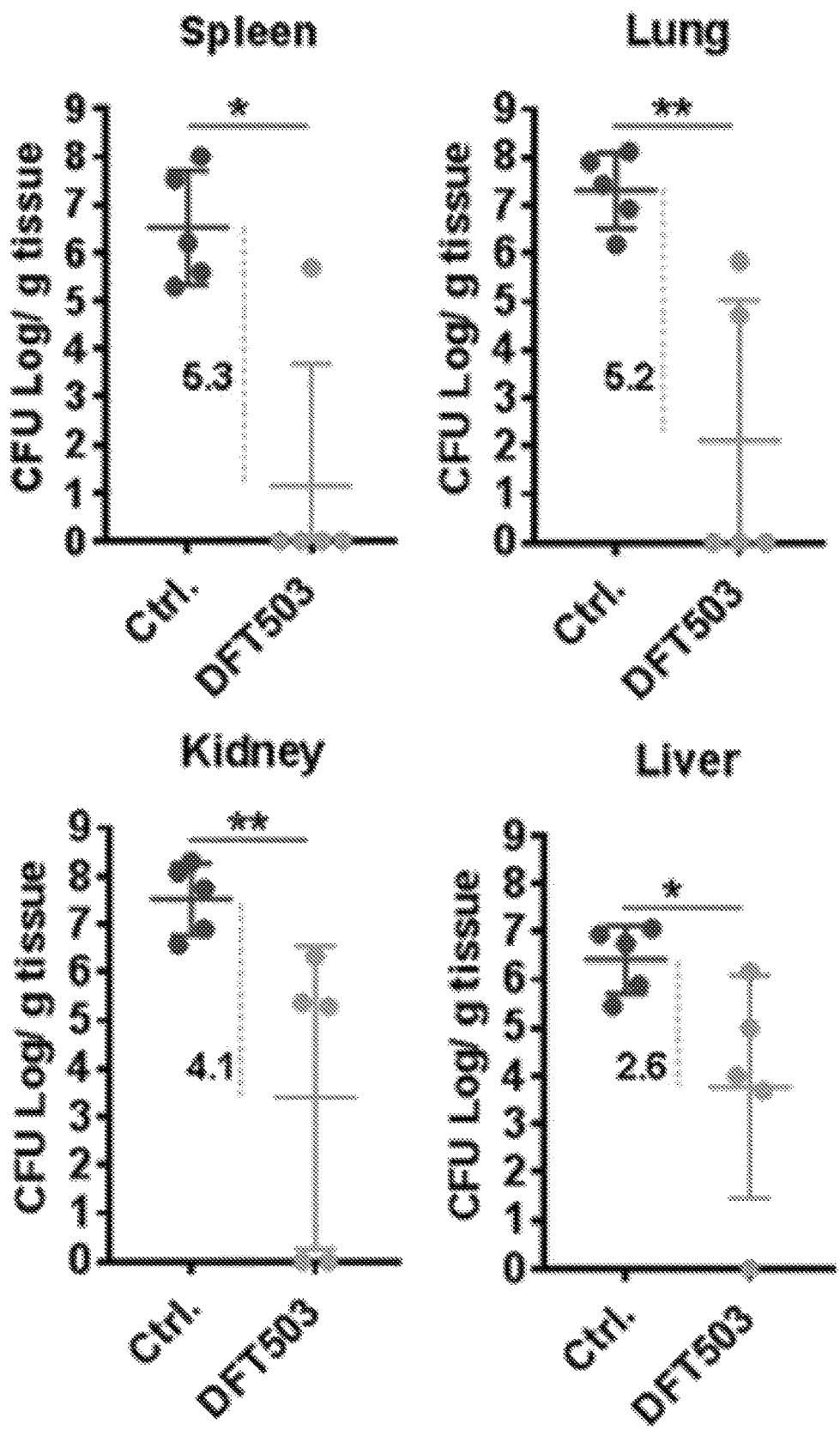

While a single dose injection facilitated the comparison of different peptides, the effect of multiple peptide doses was investigated. Remarkably, the bacterial burdens were decreased by 4-5.3 logs in spleen, lung, and kidney after two injections of DFT503 at 5 mg/kg per mouse 2 and 24 hours post-infection (FIG. 8). These results emphasize the advantage of multiple dose treatment with DFT503.

Figure 10:
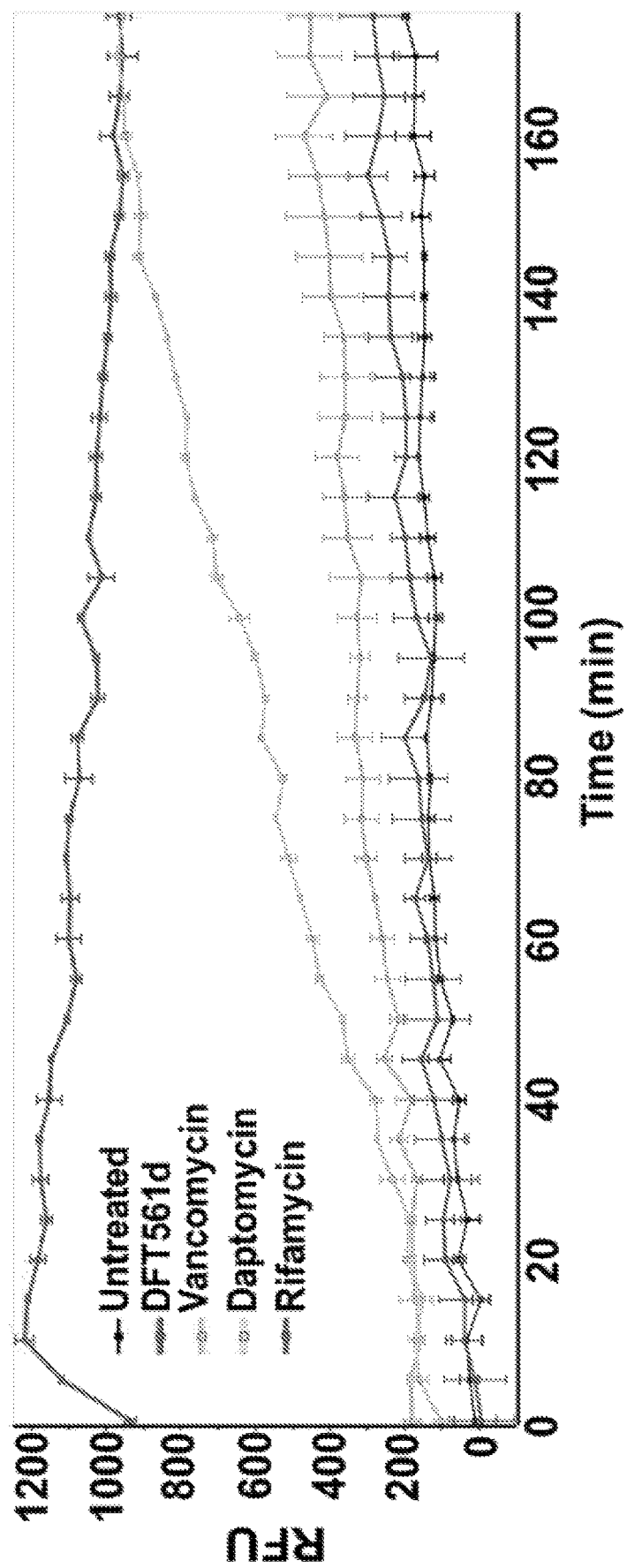
Figure 11A:
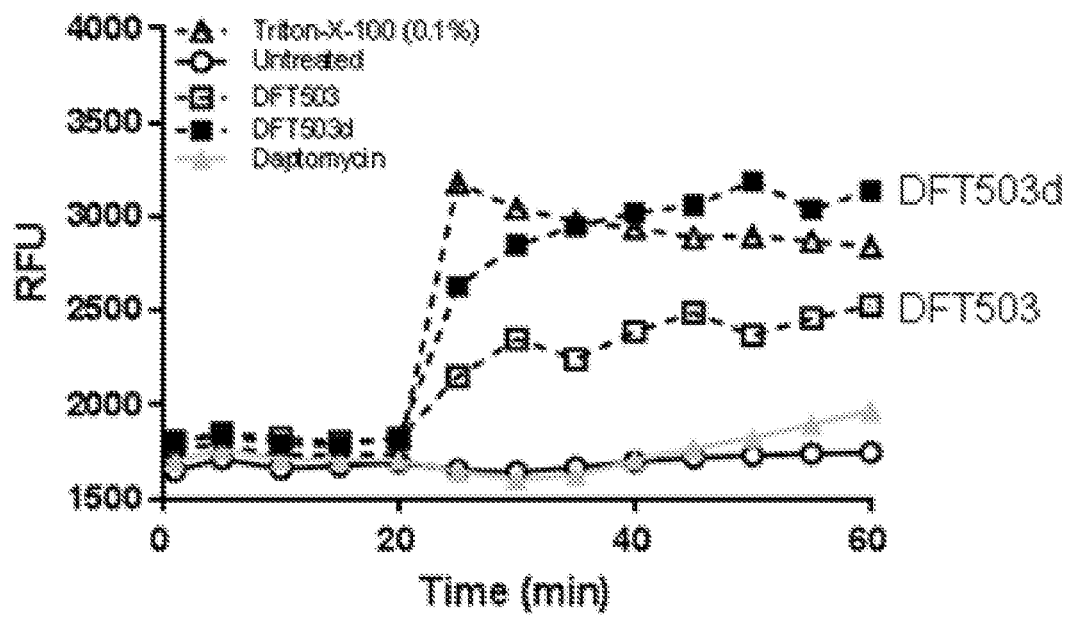
Figure 11B:
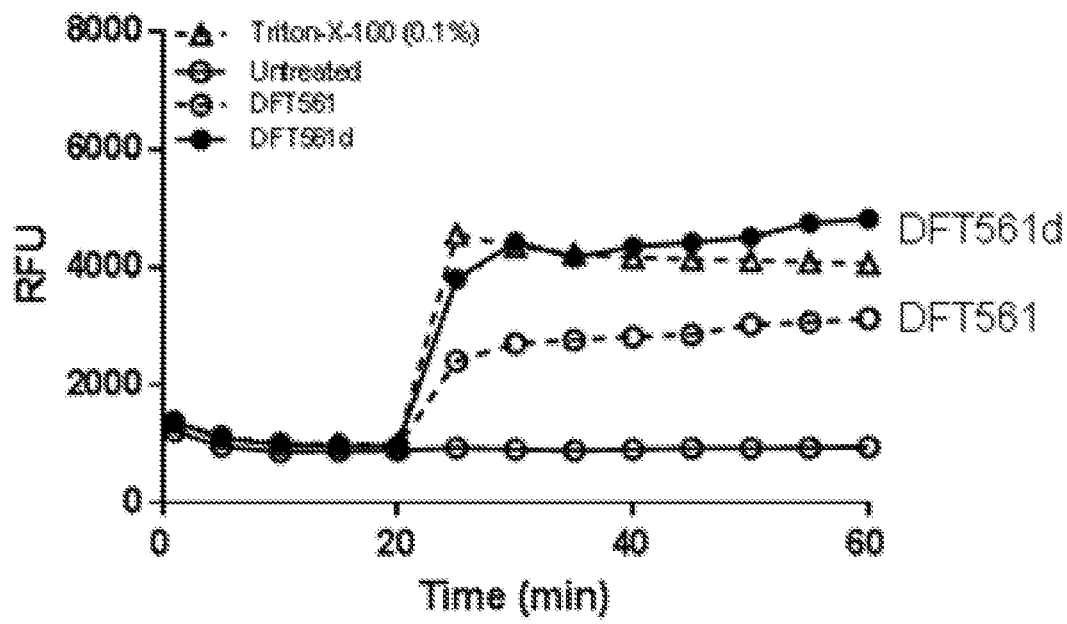

Mechanism of Action and Structural Basis of Cell Selectivity of the DFT Peptides To determine whether the peptides target membranes, a non-membrane permeable probe propidium iodide was used. A fluorescence increase was observed in the presence of DFT503, DFT503d, DFT561, DFT561d (FIG. 9A), or membrane-active daptomycin, but not membrane-inactive vancomycin and rifamycin (FIG. 10). Thus, peptide-mediated membrane permeation may have caused the loss of viability of S. aureus USA300 since no bacteria could grow (FIG. 9B). Because even better in vivo effects for DFT peptides with reduced positive charge was obtained, additional experiments using DFT503 were conducted. First, the L and D-forms of DFT503 showed essentially the same MIC (Table 5). Second, DFT503 and DFT503d at the MIC showed similar rapid killing kinetics and were able to eliminate S. aureus USA300 at 120 minutes (FIG. 9C). Third, fluorescein isothiocyanate (FITC) entry into S. aureus cells (green cells) was observed by confocal microscopy after treatment with either DFT503 or DFT503d (FIG. 9D). These experiments further support the membrane targeting nature of DFT503. However, DFT503d appeared to be more effective in depolarizing bacterial membranes than DFT503. A similar difference existed between DFT561 and DFT561d (FIG. 11). DFT503d was more potent than DFT503 in killing S. aureus USA300 in established biofilms (FIG. 12).

The 3D structure of DFT503 was determined in a membrane-mimetic micelle. For a higher quality structure, an improved 2D NMR method was used (Wang, et al. (2005) J. Biol. Chem., 280:5803-5811), which is essential for structural determination of peptides rich in certain amino acids (Wang, G. (2013) Pharmaceuticals 6:728-758; Conibear, et al. (2012) Biochemistry 51:9718-9726). Compared to the classic homonuclear 2D $^1$H NMR method (Wuthrich, K. (1986) NMR of Proteins and Nucleic Acids, John Wiley & Sons, New York), the improved method includes additional heteronuclear correlated 2D NMR spectra to validate $^1$H assignments and refine structure. DFT503, a leucine-rich peptide, adopted a helical structure based on the chemical shift analysis. The NMR analysis revealed identical secondary shift plots for both peptides DFT561 and DFT564, indicating no structural change under similar sample conditions. The 3D structure of DFT503 was determined based on 87 distance and 22 angle restraints (FIG. 1). All the backbone dihedral angles are located in the allowed region of the Ramachandran plot. Similar to DFTamP1 (FIG. 1C, 1D), DFT503 also adopted a helical structure (FIG. 1E, 1F), indicating that the local sequence shuffling is structurally tolerated. However, leucine side chains position differently. While DFTamP1 has a regular amphipathic helix with nearly all the leucines located on the hydrophobic surface (FIG. 1C), some leucines deviated from the hydrophobic surface of DFT503 (FIG. 1E). In particular, a glycine (G9) is located on the hydrophobic surface. Because G9 does not have a side chain, it generates a structural defect locally (FIG. 1E). This structural defect (FIG. 1F) is responsible for reduced hemolysis of DFT503 compared to DFTamP1 (FIG. 1D). Thus, local sequence shuffling provides an alternative approach to generating hydrophobic defects, different from the case of D-amino acid incorporation (Li, et al. (2006) J. Am. Chem. Soc., 128:5776-5785).

The membrane targeting of DFT peptides offers an advantage. No spontaneous resistance development for DFT561d was observed in a multiple passage experiment (FIG. 3E) (Ge, et al. (1999) Antimicrob. Agents Chemother., 43:782-788; Ling, et al. (2015) Nature 520:388). Nevertheless, S. aureus is known to respond to the action of cationic peptides via the major two-component system GraRS that regulates the modification of bacterial phosphatidylglycerols with lysine by MprF (Peschel, et al. (2001) J. Exp. Med., 193: 1067-1076; Yang, et al. (2012) Infect. Immun., 80:74-81). To view the extent of resistance, the MIC values of these DFT peptides was compared using the S. aureus JE2 (wild type) and AmprF mutant strains (Fey, et al. (2013) MBio 4:e00537-12). Indeed, only a two-fold MIC increase was observed for DFT561, DFT564, and DFT565 in 50% TSB (Table 8). Remarkably, DFT503 did not show any change in MIC against these two strains at different concentrations of TSB (25%, 50% and 100%), revealing another important merit of DFT503 as a potent peptide against MRSA.

TABLE 8

Peptide activity against the wild type S. aureus JE2 and its ΔmprF knocked out strains in various tryptic soy media (TSB). Peptides were quantitated by UV.

| | 25% TSB | | 50% TSB | | 100% TSB | |
|---|---|---|---|---|---|---|
| Peptide [a] | JE2 | ΔmprF | JE2 | ΔmprF | JE2 | ΔmprF |
| DFT503 | 1.56 | 1.56 | 1.56 | 1.56 | 1.56 | 1.56 |
| DFT561 | 1.56 | 0.78 | 1.56 | 0.78 | 1.56 | 1.56 |
| DFT564 | 0.78 | 0.78 | 1.56 | 0.78 | 1.56 | 1.56 |
| DFT565 | 1.56 | 1.56 | 3.1 | 1.56 | 1.56 | 1.56 |

Figure 3I:
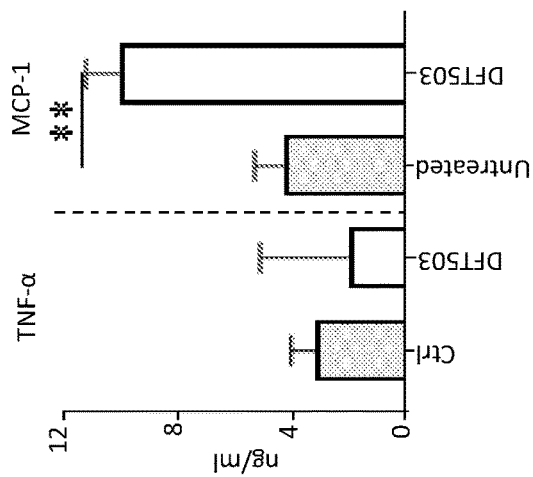
Figure 3H:
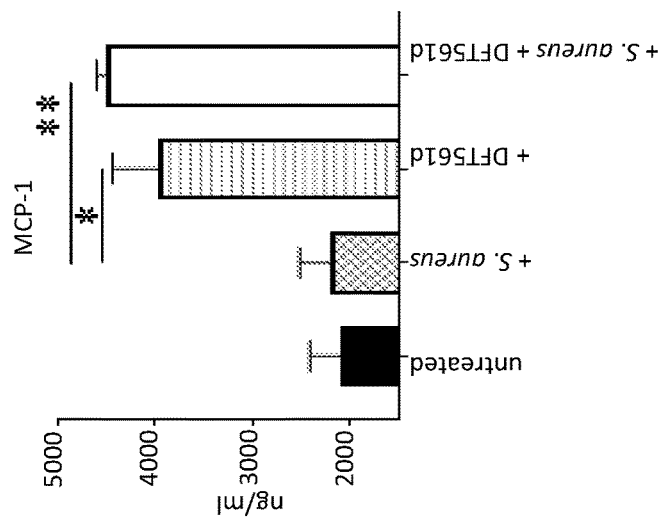
Figure 3G:
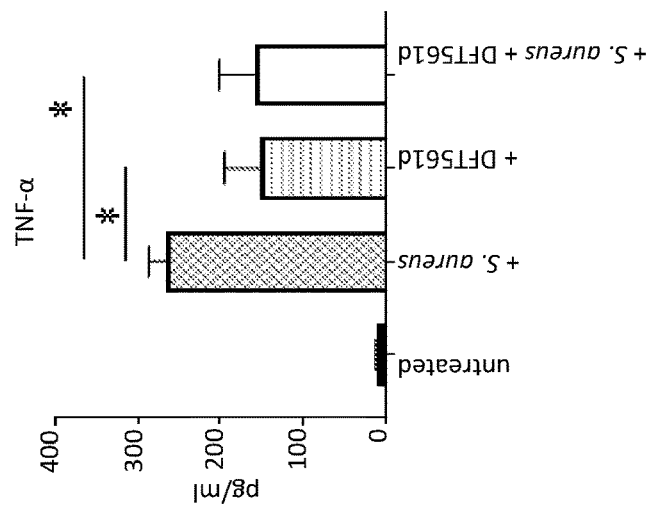
Figure 4:
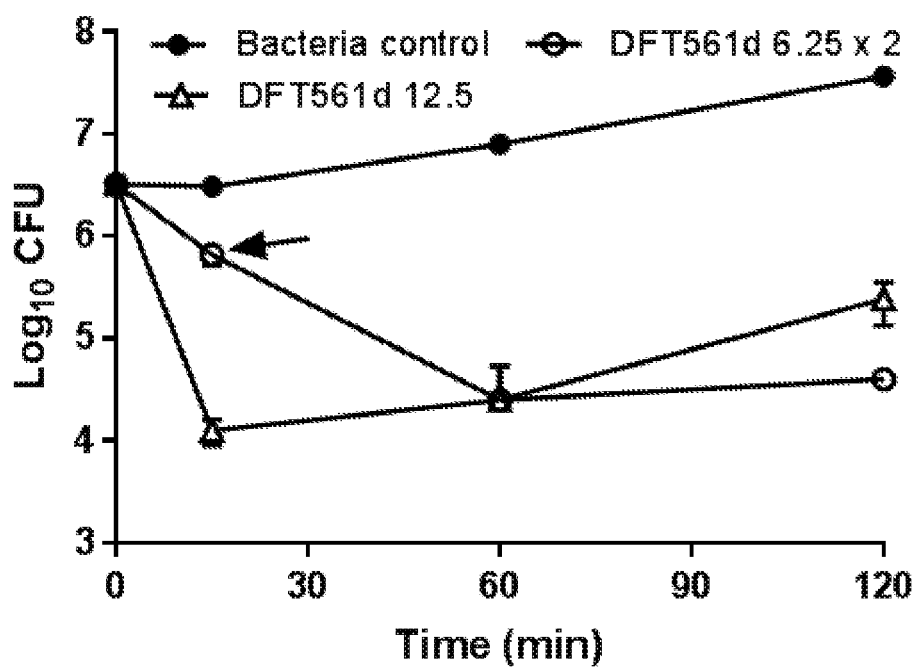
Figure 13A:
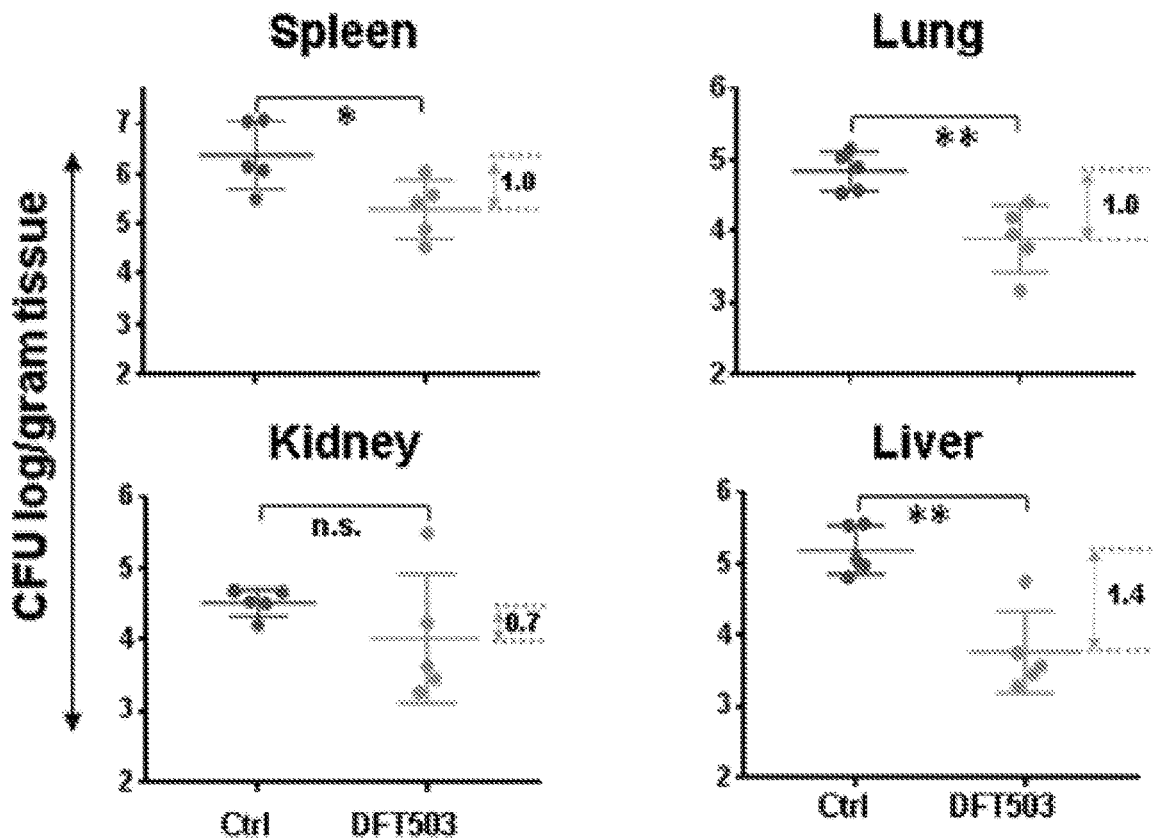
Figure 13B:
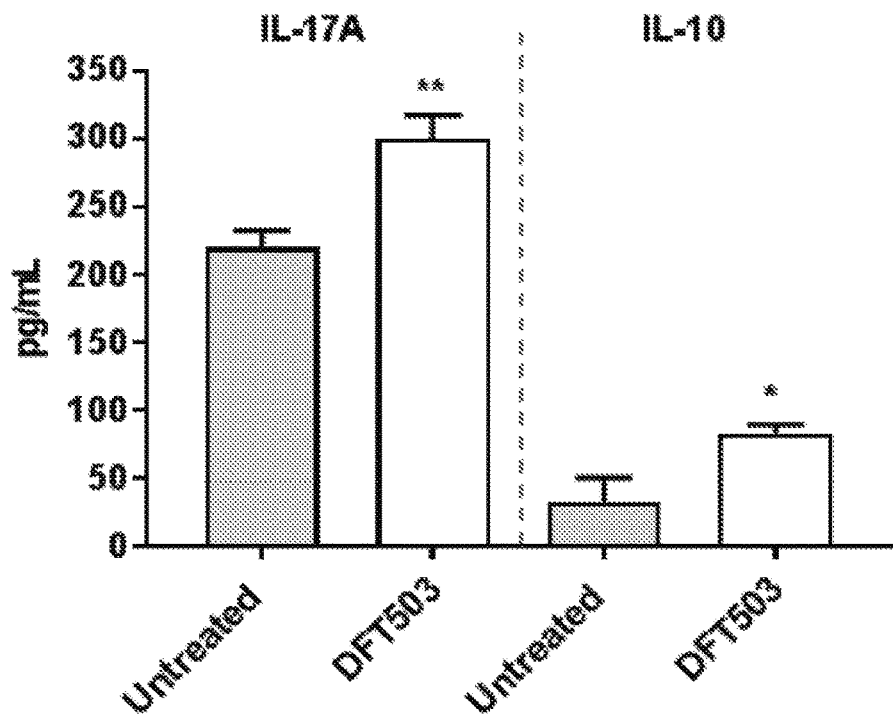

Beyond direct antimicrobial killing, cationic AMPs also regulate immune response of host cells (Hancock, et al. (2006) Nat. Biotechnol., 24:1551-1557; Lai, et al. (2009) Trends Immunol., 30:131-141). At a bactericidal concentration (1.6-3.1 μM) of DFT561d, there was essentially no change in viable THP-1 macrophages (FIG. 3F). Upon S. aureus infection, there was an increased release of chemokine TNF-α from THP-1 cells. Notably, DFT561d could suppress this bacteria-induced TNF-α (FIG. 3G). In contrast, the level of MCP-1 was upregulated due to the effect of DFT561d (FIG. 3H). Hence, the designed peptide regulated the chemokine levels of THP-1 cells in vitro. To further verify this observation, these chemokine changes were evaluated in vivo. This requires efficacy testing of the peptide in nonneutropenic mice. A similar in vivo efficacy was observed when treated at a single dose of 10 mg/kg DFT503 due to a 100-fold higher inoculum of $2.0 \times 10^8$ CFU S. aureus USA300 per mouse (FIG. 13A). The TNF-α and MCP-1 levels were then measured in mouse plasma. Interestingly, suppression of TNF-α and induction of the level of MCP-1 was also observed (FIG. 3I), consistent with the observation in vitro (FIG. 3G, 3H). In addition, the levels of IL-17A and IL-10 were also increased at 24 hours (FIG. 13B). While IL-17 can recruit neutrophils, IL-10 may neutralize TNF-α, attenuate tissue pathology and reduce mortality (Narita, et al. (2010) Infect. Immun., 78:4234-4242). In addition, the balance between the IL-10 and IL-17 cytokines is also crucial for bacterial elimination and protecting the host from pathological condition at the site of infection (Leech, et al. (2017) J. Immunol., 198:2352-2365; Sewnath, et al. (2001) J. Immunol., 166:6323-6331). These results depict a picture that DFT peptides play a critical role in eliminating S. aureus USA300 via direct killing as well as immune regulation both in vitro and in vivo.

Antimicrobial peptides are widely recognized candidates for developing novel antibiotics. However, it remains challenging to design peptides with systemic in vivo efficacy. Indeed, no AMPs designed from vertebrate hosts have been approved by the FDA for use in humans as new antibiotics. The results presented here indicate that peptide amino acid composition plays a major role in determining its activity against bacteria. Some variation in amino acid sequence is allowed since numerous peptides remained active against MRSA after an alanine scan or local sequence shuffling (Tables 2 & 4). However, amino acid sequences are also important for peptide activity and toxicity, and could become critical for non-membrane targeting AMPs. Of note, the DFT peptides displayed systemic in vivo efficacy at 5 mg/kg. Although they are not as potent as daptomycin (10 mg/kg) after single-dose treatment, an improved outcome was obtained via two doses treatment, revealing the therapeutic potential of the peptide (FIG. 8). The results also indicate the requirement of new ideas and concepts for developing cationic AMPs into novel antibiotics. First, in contrast to the common perception that serum/plasma binding is responsible for activity loss of cationic AMPs in vivo, the fact that in vivo efficacy was observed for serum-binding DFT503 indicates this requirement is not general. Second, despite higher stability to proteases of the D-form than the L-form of DFT561, similar in vivo efficacy was found in mice when the peptides were i.p. administered. This may result from fast bacterial killing of the membrane-targeting peptide. Thus, increased peptide stability may not be generally required for in vivo efficacy. From a different point of view, peptide degradation after bacterial killing can avoid unwanted effects due to compound accumulation. In addition, peptide degradation removes selection pressure, minimizing the likelihood of bacterial resistance development. Third, it appears that high hydrophobicity and low cationicity provides one useful avenue to the design of peptides with systemic in vivo efficacy against gram-positive MRSA and VRE. This is an important observation because a further increase in positively charged lysine demonstrated unwanted outcomes both in vitro and in vivo. It is likely that high cationicity is also responsible, at least partially, for the failure of some typical AMPs (4-9 lysines/arginines) in vivo. These include human cathelicidin LL-37 derived HC10 and amphibian derived peptides MSI-78 and DS4(1-16) (Table 9) that were assessed in the same murine model (Radzishevsky, et al. (2007) Nat. Biotechnol., 25:657-659).

TABLE 9

Properties of antimicrobial peptides tested in systemic mouse models.

| Peptide | Amino acid sequence | Length | K | R | K + R | (K + R) % | Pho % |
|---|---|---|---|---|---|---|---|
| MSI-78 | GIGKFLKKAKKFGKAFVKILKK (SEQ ID NO: 35) | 22 | 9 | 0 | 9 | 40.9 | 45 |
| DS4(1-16) | ALWMTLLKKVLKAAAK (SEQ ID NO: 36) | 16 | 4 | 0 | 4 | 25.0 | 68 |
| Distinctin[a] | NLVSGLIEARKYLEQLHRKLKN CKV (SEQ ID NO: 37) ENREVPPGFTALIKTLRKCII (SEQ ID NO: 38) | 46 | 6 | 4 | 10 | 21.7 | 41 |
| A3-APO | RPDKPRPYLPRPRPPRPVR (SEQ ID NO: 39) | 19 | 1 | 6 | 7 | 36.8 | 10 |
| Teixobactin | FISQIISTARI (SEQ ID NO: 40) | 11 | 0 | 1 | 1 | 9.1 | 54 |
| DFT503 | GLSLLLSLGLKLL (SEQ ID NO: 23) | 13 | 1 | 0 | 1 | 7.7 | 61 |
| DFT561 | GLKLLLSLGLKLL (SEQ ID NO: 30) | 13 | 2 | 0 | 2 | 15.4 | 61 |
| DFT564 | GLKLLLKLGLKLL (SEQ ID NO: 33) | 13 | 3 | 0 | 3 | 23.1 | 61 |
| DFT565 | KLKLLLKLGLKLL (SEQ ID NO: 34) | 13 | 4 | 0 | 4 | 30.8 | 61 |

[a]SEQ ID NO: 37 and SEQ ID NO: 38 of distinctin are connected via an intermolecular disulfide bond.

Figure 14:
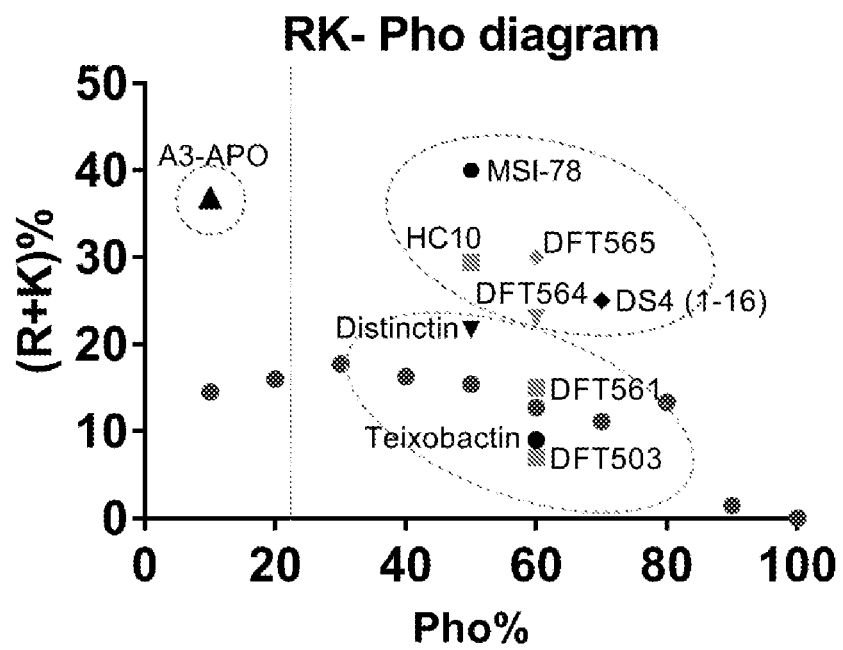

A RK-Pho diagram based on the 3014 AMPs currently registered in the APD was generated (FIG. 14). The RK-Pho diagram depicts a correlation between peptide hydrophobic contents (Pho) and percent of basic amino acids (arginines+lysines). When the RK and Pho for peptides that had been tested in vivo for systemic efficacy were mapped, it was found that those peptides worked in vivo are closer to the RK-Pho dots from the database, whereas those failed in vivo are more deviated. However, an outlier A3-APO, a proline-rich peptide also rich in basic charges, was also found. Although the parameters of this peptide were deviated from the RK-Pho plot, it showed in vivo efficacy (Szabo, et al. (2010) Int. J. Antimicrob. Agents 35:357-361). In contrast to the membrane-active peptides studied here, this outlier only kills gram-negative pathogens by targeting intracellular molecules such as heat shock proteins (Szabo, et al. (2010) Int. J. Antimicrob. Agents 35:357-361). In addition, proline-rich peptides have a low hydrophobic content (on average 25.4% for the 67 such peptides in the APD) (Wang, et al. (2016) Nucleic Acids Res., 44:D1087-93), while the peptides studied here have a high hydrophobic content (61.5%).

On average, AMPs have +3.3 positively charged amino acids with 41.5% hydrophobic amino acids (Wang, et al. (2016) Nucleic Acids Res., 44:D1087-93). It is shown here that the requirement for decreased binding to plasma and increased peptide stability may not be general characteristics of cationic AMPs with in vivo efficacy. However, this study reveals the importance of low cationicity and high hydrophobicity for systemic in vivo efficacy of membrane-active peptides against gram-positive pathogens because an increase in lysine led to loss of efficacy in murine models. Additional positive charges might have facilitated peptide binding to host factors in vivo, rendering them unavailable for bacterial killing. In contrast, proline-rich peptides with high positive charges but low hydrophobic amino acids may also be less favorable to bind to multiple host factors, yielding an alternative design for in vivo efficacy against gram-negative pathogens (Ostorhazi, et al. (2018) Front. Chem. 6:359; Holfeld, et al. (2018) J. Antimicrob. Chemother., 73:933-941; Ostorhazi, et al. (2011) Int. J. Antimicrob. Agents, 37:480-484). Collectively, these results define two biased amino acid compositions for designing narrow-spectrum peptides with systemic in vivo efficacy: low cationic database designed peptides against gram-positive pathogens and low hydrophobic proline-rich peptides against gram-negative pathogens.

Example 2

The misuse and overuse of conventional antibiotics has led to a health crisis where no effective antibiotics are available to treat the infections from the nightmare pathogen *Klebsiella pneumoniae*. *Klebsiella* is a great concern as it represents one of the ESKAPE pathogens that evade the attack of conventional antibiotics. These ESKAPE pathogens, including Gram-positive *Enterococcus faecium*, *Staphylococcus aureus*, Gram-negative *Klebsiella pneumoniae*, *Acinetobacter baumannii*, *Pseudomonas aeruginosa*, and *Enterobacter* species, are responsible for 90% of hospital-associated infections (Azzopardi, et al. (2011) J. Burn Care Res., 32:570-576). To meet this challenge, it is critical to discover a new generation of potent antibiotics. Since most of the current drugs are derived from natural products, naturally occurring antimicrobial peptides (AMPs) are worthwhile to consider (Zasloff, M. (2002) Nature 415:389-395; Marr, et al. (2006) Curr. Opin. Pharm., 6:468-472; Yeaman, et al. (2003) Pharmacol. Rev., 55:27-55; Lai, et al. (2009) Trends Immunol., 30:131-141; Mishra, et al. (2017) Curr. Opin. Chem. Biol., 38:87-96). These peptides are key components of the host innate immune system and play a critical role in protecting the host from pathogenic infection. According to the antimicrobial peptide database (APD) (Wang, et al. (2016) Nucleic Acids Res., 44:D1087-D1093), AMPs have been identified in six life kingdoms, ranging from bacteria to animals. Recently, the search has been extended to uncultivable soil bacteria and led to the identification of teixobactin by utilizing the i-chip technology (Ling, et al. (2015) Nature 517:455-459). New peptides can also be identified in silico based on QSAR (Hilpert, et al. (2005) Nat. Biotechnol., 23:1008-1012). The APD database enabled the development of the grammar approach to generate new peptide hybrids (Loose, et al. (2006) Nature 443:867-9). Also, this set of peptides enabled a database screening (Wang, et al. (2010) Antimicrob. Agents Chemother., 54:1343-1346). In addition, a database filtering technology was developed for designing potent peptides against methicillin-resistant *Staphylococcus aureus* (MRSA) (Mishra, et al. (2012) J. Am. Chem. Soc., 134: 12426-12429). While in vitro filtering enabled the identification of a robust peptide with antimicrobial potency under different physiological conditions, in vivo filtering uncovered the importance of low cationicity for systemic efficacy (see Example 1). Herein, two ultrashort peptides with outstanding efficacy in different mouse models are provided. While horine shows systemic in vivo efficacy against Gram-positive MRSA, verine is potent against both MRSA and the nightmare pathogen in mice.

Materials and Methods

Peptide and Chemicals

All peptides were chemically synthesized and purified to >95% (Genemed Synthesis). The quality of each peptide was determined based on Mass Spectrometry and HPLC. Peptides stock solutions were made by solubilizing in autoclaved distilled water and their concentrations were quantitated using UV spectroscopy based on the tryptophans at 280 nm. Other chemicals were purchased from Sigma unless specified.

Bacterial Strains and Growth Media

The bacterial strains used include the Gram-positive bacteria methicillin-resistant *Staphylococcus aureus* USA300, *Enterococcus faecium* V286-17 (VRE), *S. aureus* M838-17 (MRSA) and Gram-negative bacteria *E. coli* E423-17, E416-7 (ampC), *P. aeruginosa* E411-17, PA01, *K. pneumoniae* E406-17, ATCC13883, and *A. baumannii* B26-16. Bacteria were cultivated in tryptic soy broth (TSB) from BD Bioscience.

Peptide Stability in the Presence of Biological Fluids

Stability of horine and verine was evaluated in the presence of mouse plasma and peritoneal fluid using SDS-PAGE electrophoresis. Briefly, a peptide with 5% mouse plasma and 50% peritoneal fluid in 10 mM PBS buffer (pH 7.4) was incubated at 37° C. for 24 hours. Aliquots (10 µL) of the reaction solutions were taken and mixed with 20 µL of 2×SDS loading buffer and boiled in a water bath to stop the reaction. For the SDS gel analysis, 10 µL of each sample was loaded to the well of a 5% stacking/18% resolving tricine gel and run at a constant current of 35 mA. The gels were stained using the Coomassie Brilliant Blue G-250 dye.

Antimicrobial Assays

The antibacterial activity of peptides was evaluated using a standard broth microdilution protocol with minor modifications (Mishra, et al. (2017) Acta Biomater., 49:316-328). In brief, logarithmic phase bacterial cultures (i.e., optical density at 600 nm≈0.5) were diluted to 0.001 OD and aliquoted 90 μL per well into a 96-well polystyrene microplate. Added 10 μL peptides per well with various concentrations, plates were incubated at 37° C., overnight. Post incubation the plates are read at 630 nm using a ChroMate® Microplate Reader (GMI). The minimal inhibitory concentration (MIC) is the lowest peptide concentration that fully inhibited bacterial growth. To study the influence of medium conditions on the antimicrobial activity of peptides against S. aureus USA300 at different pHs (6.8, 7.2, and 8.0), 150 mM sodium chloride (NaCl), 5-10% of human serum, mouse plasma, and peritoneal fluid were included into the assays.

Hemolytic Assay

Hemolytic assays of peptides were performed as described (Mishra, et al. (2017) Acta Biomater., 49:316-328). Briefly, human red blood cells (hRBCs) obtained from UNMC Blood Bank. The blood washed 3× with isotonic saline (0.9% NaCl) and diluted to 2% blood cells (v/v). Peptide horine and verine at various concentrations were added into the 2% blood cells and incubated at 37° C. for 1 hour. Post incubation the plates were spun at 2000 rpm for 10 minutes, aliquots of the supernatant were carefully transferred to a fresh 96-well microplate. The amount of cells lysed is proportional to the hemoglobin released and measured at 545 nm using a ChroMate® microplate reader. The percent lysis was calculated by assuming 100% release when human blood cells were treated with 1% Triton™ X-100, and 0% release when incubated with PBS. The peptide concentration that caused 50% lysis of hRBCs is defined as $HL_{50}$.

Cell Viability Assay

Peptides assessed for potential cytotoxicity using HepaRG (human hepatic progenitor cell line) and HEK-293 (human embryonic kidney) cells. Briefly, cells were seeded at a density of $1 \times 10^4$ per well in a tissue culture 96-well plate. For HepaRG cells, the working medium is prepared by adding the HepaRG Supplement to 100 ml/500 ml of Williams' Medium E and 1 ml/5 ml of GlutaMAX-1. For HEK-293 cells, DMEM supplemented with 10% fetal bovine serum (FBS) for both cell lines, and incubated at 37° C. in a 5% $CO_2$ atmosphere for 24 hours. Culture medium was aspirated and replaced with fresh serum free media. Cells were exposed to different concentration of horine and verine for 1 hour at 37° C. in a 5% $CO_2$ atmosphere. Post-incubation, the cells were washed and incubated with 100 μL of HepaRG specific/DMEM media containing 20 μL of MTS reagent for 2 hours at 37° C. Absorbance was read at 492 nm using a ChroMate® microplate reader (GMI).

Killing Kinetics of Exponential Bacteria and Persisters

Killing kinetics experiments were conducted similar to antibacterial assays described above with the following modifications. The bacterial cells were induced into presisters in the presence of nafcillin. Aliquots of cultures (~$10^5$ CFU) treated with different peptides were taken at 15, 30, 60, 90, and 120 minutes, diluted 100-fold, and plated on Luria-Bertani agar plates and incubated at 37° C. overnight. The bacterial CFU was enumerated.

Real Time-Fluorescence Based Membrane Integrity

The experiment was performed as described previously with minor modifications (Mishra, et al. (2017) Acta Biomater., 49:316-328). Serially diluted 10× peptides (10 μL each well) were created in 96-well microtiter plates. Propidium iodide (2 μL) at a fixed concentration of 20 μM were added to each well followed by 88 μL of the S. aureus USA300 culture (a final $OD_{600}$~0.1 in TSB media or PBS). The plate was incubated at 37° C. with continuous shaking at 100 rpm in a FLUOstar® Omega (BMG LABTECH) microplate reader. The samples fluorescence was read at every 5 minutes for 24 cycles with an excitation and emission wavelengths of 584 nm and 620 nm, respectively. Plots generated using average values from the experiments using GraphPad Prism.

Membrane Depolarization of Bacteria

Using overnight culture of S. aureus USA300 was grown in TSB media to the exponential phase. Cells spun using centrifugation and washed 2× with PBS, and re-suspended in twice the volume of PBS containing 25 mM glucose and incubated at 37° C. for 15 minutes. For membrane depolarization measurements, 500 nM (final concentration) of the dye DiBAC4 (3) bis-(1, 3-dibutylbarbituric acid) trimethine oxonol (Anaspec, Fremont, CA) was added, and vortex gently. Aliquots of 90 μL of the energized bacteria solution were loaded to the wells and the plate (Corning Costar®) was fed into a FLUOstar® Omega (BMG LABTECH) microplate reader. Fluorescence was read for 20 minutes at excitation and emission wavelengths of 485 nm and 520 nm, respectively, to get dye normalization. Then 10 μL of peptide solutions was added, gently mixed. fluorescence reads were recoded for 40 minutes, where Triton™ X-100 (0.1%) was used as a positive control.

Lipopolysaccharide (LPS) Binding Assays

The LPS (endotoxin) binding assay was carried out by utilizing the Pierce™ LAL Chromogenic Endotoxin Quantitation Kit (Thermo Scientific Cat No. 88282) (Turner, et al. (1998) Antimicrob. Agents Chemother. 42:2206-2214). Twenty-five microliter of serially diluted peptide solution and 25 μL of 4 U/mL of LPS were mixed in each well, and plates were incubated for 5 minutes at 37° C. to allow the peptide to bind LPS. The mixture was then incubated for 10 minutes in the presence of 50 μL of amebocyte lysate reagent. Subsequently, 100 μL of the chromogenic substrate was added. Incubation was continued at 37° C. for another 6 minutes and stopped with 50 μL of 25% acetic acid. The release of the product was monitored at 405 nm using a ChroMate® Microplate Reader (GMI). The percentage of LPS binding to the peptide at different concentrations was calculated from the control well without peptide.

Effects of Horine and Verine on 48 Hour Established Biofilms

The antibiofilm potency of horine and verine against 48 hours established biofilms was evaluated against MDR. Briefly, S. aureus USA300 and K. pneumoniae E406-17 ($10^5$ CFU/mL) were prepared from exponentially phase. Each well of the microtiter plate (Corning Costar® Cat No. 3595) was aliquoted with 180 μL of inoculum and the plates were incubated at 37° C. for 48 hours to form biofilm. Culture treated with water served as a positive control while media without bacterial inoculation served as the negative control. Media was aspirated post incubation and the attached biofilms were washed with 1×PBS to remove the planktonic bacteria. Each well was aliquoted with 20 μL of 10× peptide solution and 180 μL of fresh TSB media, plates were further incubated at 37° C. for 24 hours. Media aspirated from the wells and washed with 1×PBS to remove planktonic cells. Live cells in the biofilms were quantitated using XTT [2,3-bis(2-methyloxy-4-nitro-5-sulfophenyl)-2H-tertazolium-5-carboxanilide] assay by following the manufacturer's instructions with modifications. 180 μL of fresh TSB and 20 μL of XTT solution was added to each well and the plates further incubated at 37° C. for 2 hours. Absorbance was read at 450 nm (only media with XTT containing wells served as the blank) using a Chromate® microtiter plate reader. Percentage biofilm growth for the peptide was plotted by assuming 100% biofilm growth in bacterial control alone. The data is mean±SD, the significance at p<0.5. Plots were generated using GraphPad prism.

Live and Dead Bacteria in 48 hr Biofilms Using Confocal Microscopy

S. aureus USA300 and K. pneumoniae E406-17 ($10^5$ CFU/mL) were prepared from exponentially phase. Two mL of bacterial inoculum was aliquoted into the chambers of cuvette (Borosilicate cover glass systems, Nunc Cat. No: 155380) and was incubated for 37° C., 48 hours for biofilm formation. Later, media was aspirated and chambers were washed with 1×PBS to remove non-adhered cells. To test the peptide effect on the preformed biofilms, 200 µL of 10× stocks of the peptide was added followed by 1800 µL of TSB. Control cuvettes contained water instead of peptide. The cuvettes further incubated at 37° C. for 24 hours. Post incubation, the media was aspirated and chambers were washed with 1×PBS. The biofilms were stained with 10 µL of the LIVE/DEAD kit (Invitrogen Molecular Probes) according to the manufacturer's instructions. The samples were examined with a confocal laser-scanning microscope (Zeiss 710) and the data were processed using Zen 2010 software.

Scanning Electron Microscopy (SEM)

For scanning EM, S. aureus USA300 was treated with 2×MIC peptide and fixed with 2% paraformaldehyde and 2% glutaraldehyde in 0.1 M PBS. Further, the samples were washed with Sorensen's Buffer 3 changes, 5 minutes each change. Samples were post-fixed in 1% osmium tetroxide in water for 30 minutes. After post-fixation, all samples were washed in Sorensen's buffer 3 changes at 5 minutes each change. All samples were dehydrated through a graded ethanol series (50%, 70%, 90%, 95%, 100%×3 changes) for 10 minutes each dehydration step. Subsequently, samples were placed in HMDS 100% for 10 minutes for 3 changes and left in HMDS in open dishes in the fume hood overnight to allow the HMDS to evaporate. The following day the samples were mounted on 25 mm aluminum SEM stubs with carbon adhesive tabs. Silver paste was placed around the edges of the samples. Samples were sputter coated with 50 nm of gold/palladium in a Hummer™ VI Sputter Coater (Anatech Ltd.) and examined in a FEI Quanta 200 SEM operated at 25 Kv using the EM Core Facility on campus.

In Vitro Multiple Passages to Observe Bacterial Resistance Development to the Compound This experiment was performed similar to the MIC determination with a few modifications. In short, an exponential phase S. aureus USA300 culture (i.e., optical density at 600 nm≈0.5) was diluted and partitioned into a 96-well polystyrene microplate with ~$10^5$ colony forming units (CFU) per well (90 µL aliquots). After treatment with 10 µL of peptide or antibiotics solutions at various concentrations, microplates were incubated at 37° C. overnight and read on a ChroMate® Microplate Reader at 630 nm (GMI). The minimal inhibitory concentration (MIC) was defined as the lowest peptide concentration that fully inhibited bacterial growth. The wells with sub-MIC levels of the peptides that retained growth approximately half the growth of the control wells were again re-inoculated in fresh TSB with sub-MIC concertation of peptides or antibiotics to attain exponential phase for MIC determination. Up to 16 serial passages of the bacteria cultures were conducted. The increase in the fold change (MIC on given passage/MIC recorded in first day of passage) used to determine the degree of drug resistance.

In Vivo Efficacy of Peptides

Animals caged (5 per cage) were kept in individually in ventilated cages (IVCs) at a temperature of 20 to 24° C., humidity of 50 to 60%, 60 air exchanges per hour and a 12/12-hour light/dark cycle. Mice were fed with standardized mice feed (Teklad Laboratory diet for rodents) and water (Hydropac® Alternative Watering System) from an animal's ad libitum (free feeding). All materials, including IVCs, lids, feeders, bottles, bedding, and water, were autoclaved before use. Experimental and control mice were kept in IVCs under a negative pressure and the conditions stated above. All animal manipulations were performed in a class II laminar flow biological safety cabinet.

Neutropenic Murine Infection Model

Female C57BL/6 or Balb/c mice (6 weeks old) were purchased from Charles River. The mice were induced neutropenic by administering two doses of cyclophosphamide on day 1 (150 mg/kg) and Day 4 (100 mg/kg). On day 5, mice were infected with S. aureus USA300 (~2×106 CFU per mouse) or K. pneumoniae E406-17 (~5×$10^5$ CFU per mouse) via intraperitoneal injection (i.p.). For the treatment groups, mice were i.p. or intravenous (i.v.) treated 2 hours post infection with peptides at a single dose of 5, 10, or 15 mg/kg. Both positive and negative controls are used. At the end of the experiments, all animals were sacrificed according to institutional guidelines. Organs such as spleen, liver, lung, and kidney were harvested, weighed and placed in 1 mL sterile PBS and stored on ice. Harvested organs were subsequently homogenized using a homogenizer (Omni). The homogenates, after proper dilutions, were plated onto blood agar plates and incubated at 37° C. overnight. The CFU of each mouse was plotted as an individual point and error bars represent the deviation within the experimental group. * p<0.05  p<0.01, *p<0.001 and NS represents no significance (determined by Mann-Whitney test).

Non-Neutropenic Murine Infection Model

Female C57BL/6 mice (6 weeks old) were purchased from Charles River. On the day of infection, mice were infected with S. aureus USA300 (~2×$10^8$ CFU per mouse) via intraperitoneal injection. For the treatment groups, mice were intraperitoneal i.p. or intravenous (i.v.) treated 2 hours post infection with peptides at a single dose of 5/10/15 mg/kg. Both positive and negative controls are used. At the end of the experiments, all animals were sacrificed according to institutional guidelines. Organs such as spleen, liver, lung, and kidney were harvested, weighed and placed in sterile PBS and stored on ice. Harvested organs subsequently homogenized using a homogenizer (Omni). Proper dilutions were made to get countable colonies. The homogenates plated onto blood agar plates, incubated at 37° C. for overnight. The CFU of each mouse was plotted as an individual point and error bars represent the deviation within the experimental group. * p<0.05  p<0.01, *p<0.001 and NS represents no significance (determined by Mann-Whitney test).

Catheter-Associated Biofilms Murine Model

Peptide potency was evaluated as described (Heim, et al. (2014) Methods Mol. Biol., 1106:183-191). On the day of infection, mice were anesthetized using ketamine/xylazine (100/10 mg/kg). A small incision was made on the left flank region of the mouse and using small blunt spatula and a pouch was made for catheter insertion. Sterile catheter with a length of 1 cm was inserted into the pouch aseptically. The wound was sealed using wound closure VetBond™ glue. Bacterial inoculum (20 µL with 103 CFU dose) injected into the lumen of the catheter. Treatment with peptide was injected at 2, 24, and 48 hours post infection (250 µL/mouse in and around the catheter). Mice allowed for full recovery from anesthesia in an oxygen-enriched chamber. Three days after infection, untreated and treated animal groups were $CO_2$ euthanized and the tissue around the catheter was harvested along with catheter. The catheter was sonicated (15 minutes, 37 kHz) to release the bacteria in biofilms and the tissue was homogenized. Appropriate dilutions of tissue homogenates were plated onto the blood agar, incubated overnight at 37° C. The CFU of each mouse plotted as an individual point and error bars represent the deviation within the experimental group. Degree of significance was represented as * p<0.05  p<0.01, *p<0.001 (t-test; Non-parametric, unpaired, Mann-Whitney test).

Quantification of Cytokines Using Flow Cytometry

The catheter associated tissue homogenate/plasma sample were thawed to room temperature prior to the cytokines quantification using LEGENDplex™ Mouse Inflammation Panel (13-plex) with Filter Plate kit by flow cytometry analysis (NovoCyte™, ACEA Biosciences). The protocol for the samples preparation and bead labelling is as per the manufacturer's manual. The samples were run in duplicates with appropriate standards. The data were represented as mean±SD. Plots were generated using GraphPad prism, where * p<0.05  p<0.01, *p<0.001 and NS represents no significance (determined by t-test, non-parametric, unpaired, Mann-Whitney test).

Nuclear Magnetic Resonance Structural Studies

For NMR measurements, the peptide was solubilized in 0.3 ml of aqueous solution of 90% $H_2O$ and 10% $D_2O$ containing deuterated dodecylphosphocholine (DPC) at 25° C. The peptide/DPC molar ratio was ~1:60. The pH of each sample was adjusted and measured directly in the 5-mm NMR tube with a micro-pH electrode (Wilmad-Labglass). All proton NMR data (NOESY, TOCSY and DQF-COSY) were collected using a spectral width of 8,000 Hz in both dimensions at 25° C. on a Bruker 600 MHz NMR spectrometer equipped with a triple-resonance cryoprobe. The water signal was suppressed by low power presaturation during the relaxation delay in NOESY, TOCSY and DQF-COSY experiments. To obtain backbone $^{15}N$, $^{13}C\alpha$, and $^{13}C\beta$ chemical shifts, natural abundance HSQC spectra were collected. All NMR data were processed on an Octane workstation using the NMR Pipe software (Delaglio, et al. (1995) J. Biomol. NMR 6:277-293). NMR data were apodized by a 630 shifted squared sine-bell window function in both dimensions, zero-filled prior to Fourier transformation to yield a data matrix of 2,048×1,024. NMR data were analyzed with PIPP (Garrett, et al. (1991) J. Magn. Reson., 95:214-220). The peptide proton signals were assigned using the standard procedure and validated using $^{15}N$ and $^{13}C$ chemical shifts of the peptides.

Three-Dimensional Structure of the Peptide

The 3D structure of the peptide was determined based on both distance and angle restraints by using the NIH-Xplor program (Schwieter, et al. (2003) J. Magn. Reson., 160:65-73). The distance restraints were obtained by classifying the NOE cross peak volumes into strong (1.8-2.8 Å), medium (1.8-3.8 Å), weak (1.8-5.0 Å), and very weak (1.8-6.0 Å) ranges. Peptide backbone restraints were predicted based on backbone $^{1}H\alpha$, $^{13}C\alpha$, $^{13}C\beta$, and $^{15}N$ chemical shifts (Cornilescu, et al. (1999) J. Biomol. NMR, 13:289-302). In total, 100 structures were calculated. An ensemble of structures with the lowest total energy was chosen. This final ensemble of the accepted structures satisfies the following criteria: no distance violations greater than 0.30 Å, rmsd for bond deviations from the ideal less than 0.01 Å, and rmsd for angle deviations from the ideal less than 5°.

Results

Peptide Design, 3D Structure and Improvement

Database analysis of over 3000 AMPs revealed a linear relationship between hydrophobic and arginine contents by classifying the peptides into different bins. Due to the importance of low cationicity, the APD was searched for peptides with low arginine. To reduce the cost for peptide production, a short peptide, temporin-SHf, was selected as a starting template (Abbassi, et al. (2010) J. Biol. Chem., 285:16880-92). It showed moderate activity against MRSA with a minimal inhibitory concentration (MIC) at 25 µM. Peptide potency was enhanced by deploying four tryptophan (Trp) residues. The choice of the four Trps was inspired by the sequence of gramicidin A, a bacterial peptide antibiotic used topically (Dubos, et al. (1941) J. Exp. Med., 73:629-640). Combined, a novel Trp-rich peptide WW291 (FIG. 15) was developed with anti-MRSA activity increased eight-fold (Mishra, et al. (2017) Acta Biomater., 49:316-328).

To identify peptides against Gram-negative pathogens, a clockwise sequence permutation of WW291 was conducted (FIG. 15A) and seven additional new peptides (WW292-298) were generated. These peptides share the same amino acid composition but differ in sequence (FIG. 15B). While these sequence-permutated peptides inhibited MRSA, WW295 gained activity against Gram-negative *Escherichia coli* and *K. pneumoniae* (Table 10). WW295 possesses a rather unique two-domain sequence with basic amino acids at the N-terminus and hydrophobic ones at the C-terminus (FIG. 15B).

TABLE 10

Antibacterial activity of the sequence permutated peptides of WW291.

| Peptide | Amino acid Sequence (SEQ ID NO) | Minimal inhibitory concentration (MIC, µM) | | |
|---|---|---|---|---|
| | | S. aureus USA300 | E. coli ATCC 25922 | K. pneumoniae ATCC 13883 |
| WW291 | WWWLRKIW (SEQ ID NO: 41) | 3.1 | 6.2-12.5 | 12.5 |
| WW292 | WWLRKIWW (SEQ ID NO: 42) | 6.2 | 25 | >50 |
| WW293 | WLRKIWWW (SEQ ID NO: 43) | 3.1-6.2 | 12.5-25 | 25 |
| WW294 | LRKIWWWW (SEQ ID NO: 44) | 3.1-6.2 | 12.5 | 6.2-12.5 |
| WW295 | RKIWWWWL (SEQ ID NO: 45) | 3.1-6.2 | 6.2 | 3.1-6.2 |

TABLE 10-continued

Antibacterial activity of the sequence permutated peptides of WW291.

| Peptide | Amino acid Sequence (SEQ ID NO) | Minimal inhibitory concentration (MIC, µM) | | |
|---|---|---|---|---|
| | | S. aureus USA300 | E. coli ATCC 25922 | K. pneumoniae ATCC 13883 |
| WW296 | KIWWWWLR (SEQ ID NO: 46) | 3.1 | 6.2-12.5 | 12.5 |
| WW297 | IWWWWLRK (SEQ ID NO: 47) | 3.1 | 12.5 | 12.5-25 |
| WW298 | WWWWLRKI (SEQ ID NO: 48) | 1.5-3.1 | 12.5 | 6.2-12.5 |

Figure 16A:
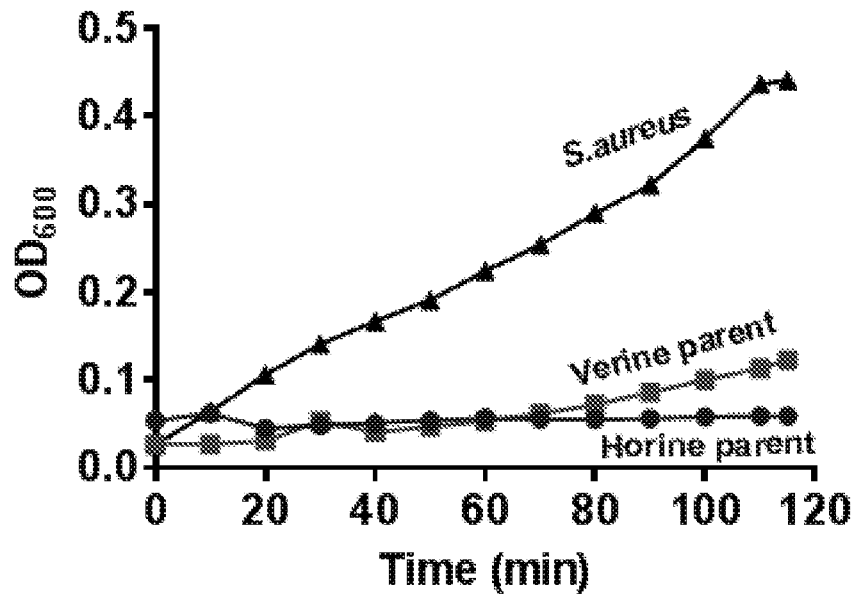
Figure 16B:
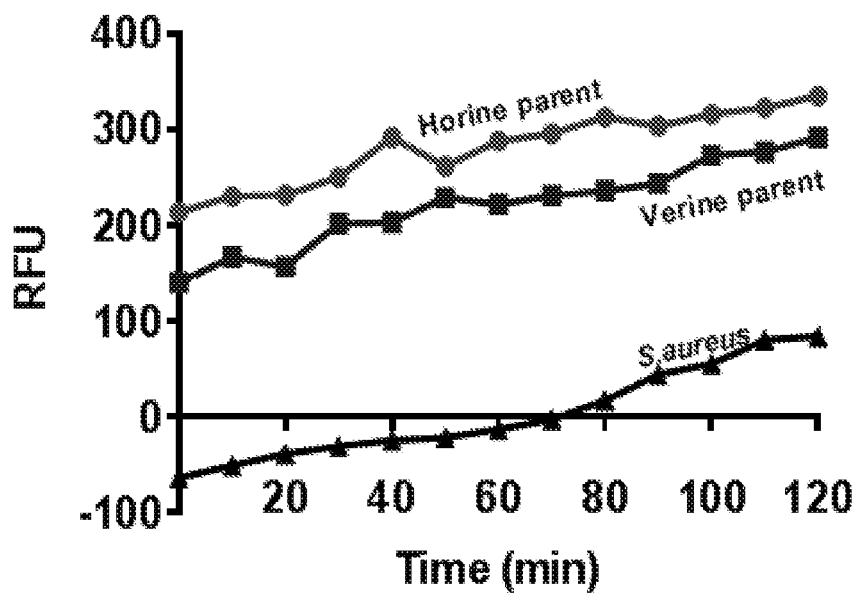

To provide insight into peptide activity, the three-dimensional structures of WW291 and WW295 were determined. Since these two peptides were found to permeate bacterial membranes (FIG. 16), their structure was determined bound to membrane-mimetic micelles. For high-quality structure, the improved 2D NMR method was used (Wang, et al. (2005) J. Biol. Chem., 280:5803-5811), which also records heteronuclear $^{15}$N and $^{13}$C-involved correlated spectra at natural abundance. The $^{13}$C chemical shifts are important here to distinguish the multiple aromatic protons from the four Trp residues (50%) of this short peptide assigned based on the standard 2D $^1$H-correlated NMR method. A combined use of distance and angle restraints generated well-defined structures (Cornilescu, et al. (1999) J. Biomol. NMR, 13:289-302). On the hydrophobic surfaces, the aromatic rings of both peptides superimposed well. In the structure of WW291, a short C-terminal helical turn is stabilized by the WWW motif (Zarena, et al. (2017) Biochemistry 56:4039-4043), whereas WW295 has a spiral structure with hydrophilic amino acids R1 and K2 at the top and hydrophobic residues clustered at the bottom (FIG. 15E). Hence, the structure of WW295 constitutes a new amphipathic model where the peptide chain folds along a vertical axis (FIG. 15F). Such an amphipathic structure differs drastically from the classic amphipathic helix of WW291 with the peptide chain folded horizontally (FIG. 15D). The amphipathic nature of these structures is also evident in the potential surfaces (FIG. 15G, 15I, white), which face the readers after a 900 rotation (FIG. 15H, 15J). It should be emphasized that these new Trp-rich peptides possess regular 3D structures, entirely different from the irregular and extended structures of those peptides known for over a decade (Chan, et al. (2006) Biochim. Biophys. Acta 1758:1184-202; Wang, G. (ed.) Antimicrobial Peptides: Discovery, Design and Novel Therapeutic Strategies, CABI, England (2017)).

For therapeutic use, it is imperative to minimize the potential toxicity of peptides to mammalian cells. Based on the structure of WW291 (FIG. 15C), peptide potency against MRSA was maintained and hemolysis was reduced by changing isoleucine and lysine to arginines (WW304 in Table 11) based on preferred association between tryptophan and arginine (Mishra, et al. (2017) Acta Biomater. 49: 316-328). WW295 was also improved by changing the terminal L8 to V8, which doubled the 50% hemolytic concentration (HL$_{50}$) (WW307 in Table 12). Because WW291 and WW295 have horizontal and vertical amphipathic axes, the improved versions of these two peptides was referred to as horine and verine, respectively. Peptide toxicity was then tested on other human and murine cells. Although verine was slightly more toxic to murine spleen, both peptides were not toxic to human cells (Table 13) at the concentrations required to kill bacteria (2-8 µM in Table 14).

TABLE 11

Structure-based improvement of WW299, an arginine analog of WW291.

| | | MIC (µM) | | | |
|---|---|---|---|---|---|
| Peptide | Amino acid sequence | P. aeruginosa PAO1 | K. pneumonia ATCC 13883 | S. aureus USA300 | HL$_{50}$ (µM) |
| WW299 | WWWLRRIW (SEQ ID NO: 49) | >50 | 25 | 3.1 | 35 |
| WW300 | RWWLRRIW (SEQ ID NO: 50) | 12.5 | >50 | 12.5 | >200 |
| WW301 | WRWLRRIW (SEQ ID NO: 51) | 6.2 | 25 | 6.2 | 100 |
| WW302 | WWRLRRIW (SEQ ID NO: 52) | 12.5 | >25 | 12.5 | >200 |
| WW303 | WWWRRRIW (SEQ ID NO: 53) | 25-50 | >25 | 12.5 | >200 |
| WW304 (Horine) | WWWLRRRW (SEQ ID NO: 54) | 12.5 | >25 | 3.1 | 150 |

TABLE 11-continued

Structure-based improvement of WW299, an arginine analog of WW291.

|  |  | MIC (µM) | | | |
| --- | --- | --- | --- | --- | --- |
| Peptide | Amino acid sequence | P. aeruginosa PA01 | K. pneumonia ATCC 13883 | S. aureus USA300 | HL$_{50}$ (µM) |
| WW305 | WWWLRRIR (SEQ ID NO: 55) | 12.5 | >25 | 12.5 | >200 |

MIC, Minimum inhibitory concentration;
HL$_{50}$ is the peptide concentration that causes 50% hemolysis;
MIC data for *S. aureus* were taken from Zarena, et al. (2017) Biochemistry 56:4039-4043.

TABLE 12

Structure-based improvement of WW295.

|  |  | MIC (µM) | | | | |
| --- | --- | --- | --- | --- | --- | --- |
| Peptide | Amino acid sequence | S. aureus M838-17 | P. aeruginosa 411-17 | K. pneumonia 406-17 | HL$_{50}$ (µM) | t$^{RP}$ (min) |
| WW295 | RKIWWWWL (SEQ ID NO: 45) | 6.2-12.5 | >50 | 12.5 | 57 | 12.3 |
| WW306 | RRRWWWWL (SEQ ID NO: 56) | 3.1 | 6.25 | 6.25 | 60 | 11.7 |
| WW307 (Verine) | RRRWWWWV (SEQ ID NO: 57) | 3.1 | 12.5 | 6.25 | 130$^2$ | 11.2 |
| WW308 | RRRWWWWA (SEQ ID NO: 58) | 12.5 | 25 | >50 | >200 | 11.0 |
| WW309 | RRRRWWWL (SEQ ID NO: 59) | 6.25 | 12.5 | >50 | >200 | 10.6 |

HL$_{50}$, the peptide concentration that causes 50% hemolysis;
t$^{RP}$, the retention time of the peptide on the reverse-phase HPLC column;
NA, not available.
$^2$Compared to Table 13, HL$_{50}$ varies to some extent due to the use of a different batch of blood cells.

TABLE 13

Toxicity of horine and verine to human and murine cells.

|  |  | LC$_{50}$ (µM) | |
| --- | --- | --- | --- |
|  | Tissue origin | Horine | Verine |
| 2% hRBCs | Human red blood cells | >200 | >200 |
| HepaRG | Human hepatic progenitor (liver) | >80 | >80 |
| HEK293 | Human embryonic kidney | >100 | >80 |
| MRC9 | Human lung fibroblasts | >35 | >25 |
| Spleenocytes | Mouse spleen | >50 | >12.5 |

TABLE 14

Minimal inhibitory concentrations (µM) of horine and verine.

| Compound | E. faecium V286-17 (VRE) | S. aureus USA300 (MRSA) | K. pneumoniae E406-17 | A. baumannii B26-16 | P. aeruginosa E411-17 | E. coli E423-17 |
| --- | --- | --- | --- | --- | --- | --- |
| WW291 | 4 | 4 | ≥32 | 16 | >32 | 8 |
| Horine | 2 | 4 | >32 | 32 | >32 | >32 |
| D-horine | 4 | 4 | >32 | >32 | 32 | 16 |
| WW295 | 4 | 4 | 16 | 8 | 32 | 8 |

TABLE 14-continued

Minimal inhibitory concentrations (μM) of horine and verine.

| Compound | E. faecium V286-17 (VRE) | S. aureus USA300 (MRSA) | K. pneumoniae E406-17 | A. baumannii B26-16 | P. aeruginosa E411-17 | E. coli E423-17 |
|---|---|---|---|---|---|---|
| Verine | 2 | 2-4 | 8 | 8 | 4-8 | 2 |
| Vancomycin | >8 | 1 | >8 | >8 | >8 | >8 |
| Rifamycin | >8 | 0.25 | >8 | >8 | >8 | >8 |
| Daptomycin | 4 | 4 | >8 | >8 | >8 | >8 |
| Colistin | >8 | >8 | >8 | 1 | 2 | 1 |
| Tobramycin | >8 | 4 | >8 | 4 | 2 | 8 |
| Doripenem | >8 | 0.25 | 0.5 | >8 | 2 | 1 |

In Vitro Antimicrobial Robustness

Since AMPs can lose activity under certain physiological conditions, antimicrobial robustness of horine and verine was further tested. When the pH of the media was reduced from 8.0 to 6.8 (e.g., in cystic fibrosis lungs) (Abou, et al. (2014) Proc. Natl. Acad. Sci., 111:18703-18708), there was essentially no change in the MIC of both peptides against S. aureus USA300. Inclusion of a physiological amount of NaCl (150 mM) did not reduce antibacterial activity of both peptides, either (FIG. 17A). However, there was a two-fold change in the MIC of verine in the presence of 5 or 10% serum, while the activity of horine was reduced four-eight fold. In a liver microsomal assay, horine and verine showed similar 5000 degradation in one hour (FIG. 17B). Interestingly, they were stable and active after incubation with murine peritoneal fluids or plasma for 3 hours (FIG. 17C). In conjunction, these peptides are likely to work under physiological conditions.

The activity of horine and verine was then tested using a set of clinically resistant bacteria that cover essentially all the ESKAPE pathogens (Table 14). Both peptides were active against Gram-positive pathogens such as vancomycin-resistant Enterococci (VRE) and MRSA (MIC 2-4 μM). In contrast, current antibiotics, such as vancomycin and rifamycin, could not kill VRE. An expanded test of the antibacterial activity against a panel of 31 clinical susceptible and resistant S. aureus strains revealed nafcillin did not inhibit the Mu50 and USA200 strains at 8 μM. However, both horine and verine worked (Table 15). At a two-fold MIC, they rapidly killed S. aureus USA300 (FIG. 17D). Importantly, horine and verine could also kill the persisters (Lewis, K. (2007) Nature Rev. Microbiol., 5:48-56) of S. aureus USA300 (FIG. 17E). In addition, verine was active against Gram-negative pathogens. While tobramycin at 8 μM failed to kill E. faecium and K. pneumoniae, verine killed both (Table 14). Moreover, this peptide killed E. faecium and A. baumannii, whereas doripenem (8 μM) was unable to. Table 16 shows the ability of verine to eliminate a variety of Klebsiella clinical strains, some of which already developed resistance to tobramycin. These results illustrate the potency of the two designer peptides against resistant pathogens and persisters.

TABLE 15

Comparison of antimicrobial activity of horine and verine with antibiotics against clinical strains of methicillin-resistant and susceptible S. aureus (MIC, μM).

| S. aureus Strains | Horine | Verine | Nafcillin | Vancomycin |
|---|---|---|---|---|
| mu50 | 4 | 8 | >8 | 2 |
| USA200 | 4 | 4 | >8 | 0.5 |
| USA300 | 4 | 4 | 0.5 | 0.5 |
| USA400 | 4 | 4 | 1 | 1 |
| UAMS-1 | 8 | 4 | 4 | 2 |
| Newman | 4 | 4 | 0.25 | 1 |
| B243-16 MSSA | 4 | 4 | <0.25 | 0.5 |
| B254-16 MSSA | 4 | 4 | <0.25 | 0.5 |
| B255-16 MSSA | 4 | 4 | <0.25 | 1 |
| B262-16 MSSA | 2 | 8 | 0.5 | 0.5 |
| B269-16 MSSA | 4 | 4 | 0.5 | 1 |
| M106-16 | 4 | 4 | 2 | 1 |
| M108-16 | 4 | 4 | 1 | 1 |
| M109-16 | 4 | 4 | 1 | 0.5 |
| M111-16 | 4 | 4 | 8 | 0.5 |
| M112-16 | 4 | 8 | 0.5 | 0.5 |
| M113-16 | 4 | 4 | 0.5 | 1 |
| M114-16 | 4 | 4 | 0.5 | 1 |
| M116-16 | 2 | 2 | <0.25 | 0.5 |
| M117-16 | 4 | 4 | 0.5 | 0.5 |
| M118-16 | 4 | 4 | 0.5 | 1 |
| M119-16 | 4 | 4 | 1 | 0.5 |
| M120-16 | 4 | 4 | 2 | 0.5 |
| M121-16 | 4 | 4 | 1 | 1 |
| M122-16 | 4 | 4 | 1 | 1 |
| M123-16 | 4 | 4 | 4 | 0.5 |
| M126-16 | 4 | 4 | 1 | 0.5 |
| M127-16 | 4 | 4 | 2 | 0.5 |
| M128-16 | 4 | 4 | 8 | 1 |
| M129-16 | 4 | 4 | 1 | 0.5 |
| M130-16 | 4 | 4 | 1 | 0.5 |

TABLE 16

Comparison of antimicrobial activity (MIC, μM) of horine and verine with antibiotics against Klebsiella pneumoniae clinical strains.

| Strains | Horine | Verine | Tigecycline | Tobramycin |
|---|---|---|---|---|
| KP-B42-15 | >64 | 8 | <2 | 8 |
| KP-B53-15 | >64 | 16 | 2 | 4 |
| KP-B73-15 | >64 | 8 | 2 | 4 |
| KP-B77-15 | >64 | 8 | <2 | 4 |
| KP-231-18 | >64 | 16 | 4 | 64 |
| KP-232-18 | >64 | 16 | 8 | >64 |
| KP-245-18 | >64 | 32 | 4 | ~4-8 |
| KP-249-18 | >64 | 16 | 2 | 8 |
| KP-253-18 | >64 | 8 | 2 | 8 |

TABLE 16-continued

Comparison of antimicrobial activity (MIC, μM) of horine and verine with antibiotics against *Klebsiella pneumoniae* clinical strains.

| Strains | Horine | Verine | Tigecycline | Tobramycin |
|---|---|---|---|---|
| KP-256-18 | >64 | 8 | 4 | >64 |
| KP-257-18 | >64 | 8 | 8 | >64 |
| KP-262-18 | >64 | 16 | 4 | 4 |
| KP-270-18 | >64 | 16 | 4 | 16 |
| KP-B1725-18 | >64 | 4 | 2 | 8 |

Figure 17G:
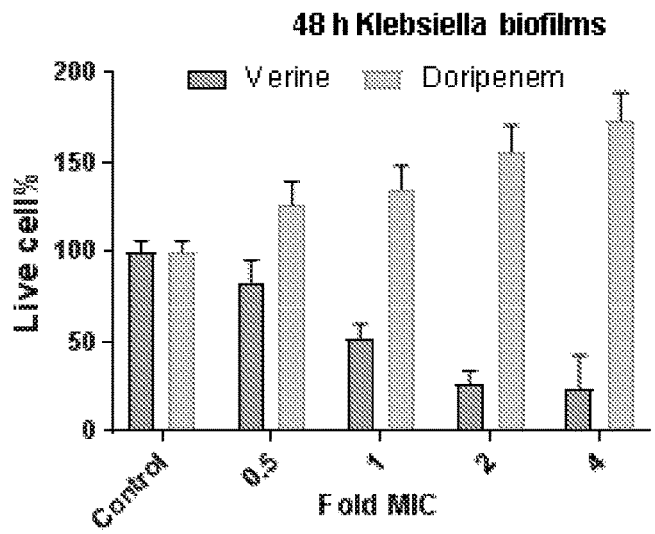
FIG. 17H shows that both peptides can effectively permeate membranes of S. aureus USA300.
FIG. 17I provides scanning electron microscopy images of membrane-damaging effects of the peptides: S. aureus (SA, left) and K. pneumoniae (KP, right).
Figure 18A:
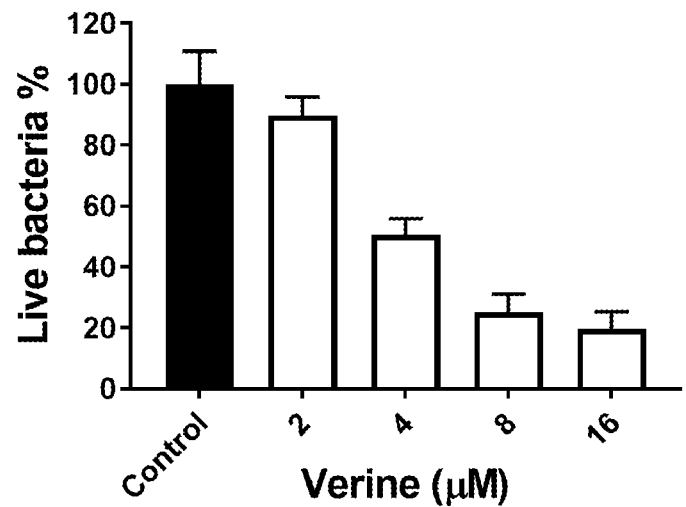
FIGS. 18A-18B show that verine (FIG. 18A), but not doripenem (FIG. 18B), inhibited the attachment of K. pneumoniae E406-17 in a dose-dependent manner.
Figure 18B:
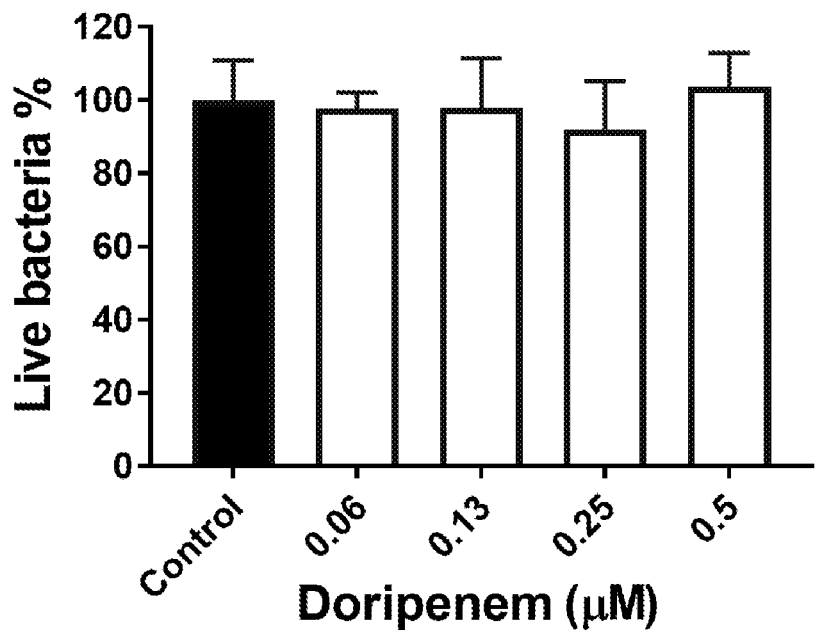

To further demonstrate the merits of the new peptides, their efficacy against biofilms was evaluated, which are notoriously difficult to treat with conventional antibiotics. While horine demonstrated dose-dependent activity against the 48-hour biofilms of *S. aureus* USA300 (FIG. 17F), nafcillin did not. Likewise, verine was potent against bacterial biofilms. It inhibited the adhesion of *K. pneumoniae* (FIG. 18A) and disrupted the 48-hour preformed biofilms (FIG. 17G). In contrast, doripenem showed no effect (FIG. 17G, 18B). Both peptides were able to kill the pathogens in biofilms as observed by confocal microscopy (FIG. 17F, 17G).

Mechanism of Action of Horine and Verine

Figure 17H:
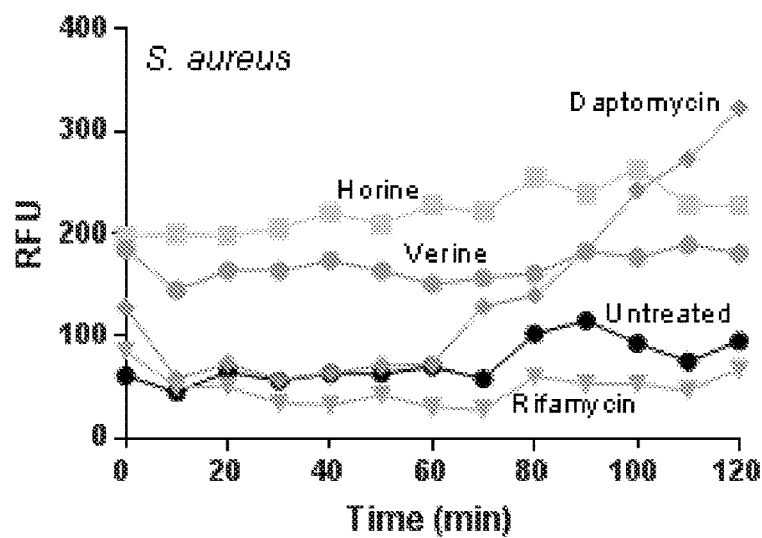
Figure 17I:
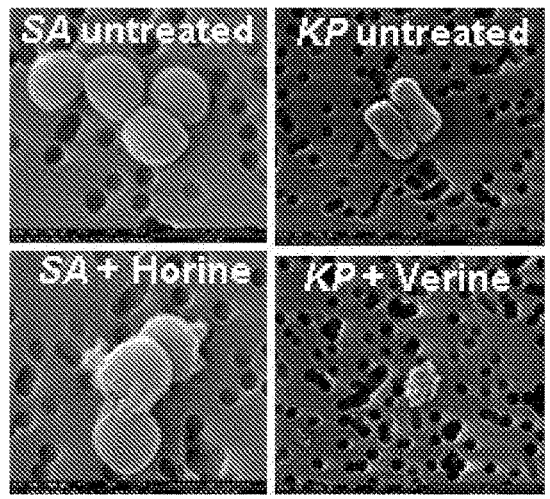
Figure 19:
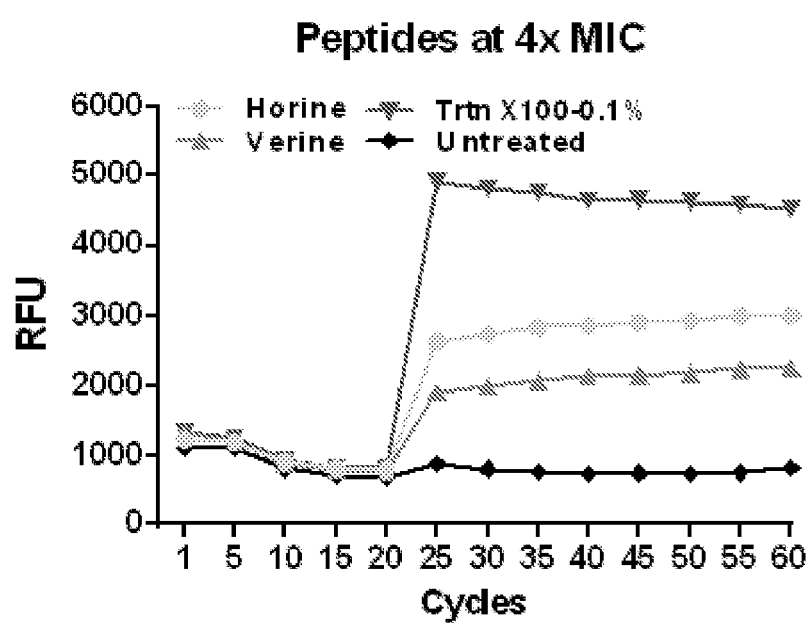
FIG. 19 shows the membrane depolarization of S. aureus USA300 by horine and verine treated at 16 µM. Triton™ X-100 (0.1%) was used as positive control for depolarization.

To provide insight into the mechanism of action, the direct interaction of the peptides with bacteria was investigated. Both peptides permeated the membranes of *S. aureus* USA300 in a propidium iodide-based fluorescent experiment, indicating membrane targeting (FIG. 17H). As a positive control, daptomycin also permeated bacterial membranes. In contrast, a non-membrane permeating antibiotic rifamycin failed to permeate the bacterial membrane, even after 2 hours. The membrane targeting of horine is also supported by the similar MIC values of the L- and D-forms of the same peptide (Table 14). Moreover, these two peptides depolarized the membranes of *S. aureus* USA300 (FIG. 19). In addition, membrane blebs were observed in the scanning electron microscopy images of *S. aureus* treated with horine (FIG. 17I). In the case of *K. pneumoniae*, verine deprived the bacteria of membranes entirely (FIG. 17I).

Lipid composition in bacterial membranes can influence peptide activity. A change of V8 in verine to A8 (WW308 in Table 12), or a change of W4 to R4 (WW309), made them inactive against *K. pneumoniae*. The hydrophobic requirement for verine to kill *K. pneumoniae* is consistent with its membrane composition rich in phosphatidylethanolamine (PE, 80%) but poor in phosphatidylglycerol (PG, 5%) (Wang, et al. (2014) Biochim. Biophys. Acta 1838:2160-2172). In contrast, the tolerance with the W4R mutation in killing *P. aeruginosa* is supported by an increased level of anionic lipids in its membranes (PG, 21% and PE, 60%) (Wang, et al. (2014) Biochim. Biophys. Acta 1838:2160-2172). To further substantiate membrane targeting, a *S. aureus* mutant from the Nebraska Transposon Mutant Library (Fey, et al. (2013) MBio. 4:e00537-12) was used. When the mprF gene was inactivated, *S. aureus* became more susceptible to cationic peptide killing since this mutant was unable to transfer a basic lysine to the head group of acidic PG (Peschel, et al. (2001) J. Exp. Med., 193:1067-1076; Yang, et al. (2012) Infect. Immun., 80:74-81). Compared to the wild type staphylococcal strains (JE2 and USA300), the MIC values of horine and verine were only reduced two-fold against the mprF disrupted mutant (Table 17). Membrane targeting of horine and verine poses difficulty to bacterial resistance development. To illustrate this, an in vitro multiple passage experiment was conducted in the presence of a sub-MIC level of peptides. While the MIC of nafcillin increased 1000 fold against *S. aureus* USA300 after 16 passages, there was no change for horine and verine. Collectively, these results support the robustness of horine and verine in eliminating drug-resistant pathogens via membrane damage, laying the foundation for efficacy tests in vivo.

TABLE 17

Minimal inhibitory concentrations (μM) of horine and verine against *Staphylococcus aureus* and its mutants.

| *S. aureus* strain | Horine | Verine |
|---|---|---|
| USA300 | 4 | 2-4 |
| JE2 | 4 | 4 |
| ΔmprF | 2 | 2 |

In Vivo Toxicity, Efficacy and Immune Regulatory Studies of Horine and Verine

Neutropenic mice are widely accepted for systemic efficacy evaluation of antibiotics (Zhao, et al. (2016) Bioorg. Med. Chem. 24:6390-6400; Craig, et al. (1991) J. Antimicrob. Chemother., 27:29-40). This model enables better evaluation of compound potency by minimizing the bacterial clearance effect of the immune system. Using this model, the efficacy of horine against *S. aureus* USA300 and verine against *K. pneumonia* E406-17 was tested. C57BL/6 mice were made neutropenic by two injections of cyclophosphamide intraperitoneally (i.p.). The acute toxicity of horine and verine was investigated by i.p. injecting them into mice at 10, 20, and 30 mg/kg body weight. At higher peptide doses, only an initial short-term reduced mobility was observed, but no animal death in the entire five-day experiment.

After confirming the safety of both peptides, their efficacy was tested in the 10-15 mg/kg range. In the survival experiment where mice were i.p. infected with $1 \times 10^7$ colony forming units (CFU), all the mice in the untreated group died within two days. However, 75% of the mice survived in the horine-treated group during the five-day observation, indicating a protective effect of horine. Likewise, 100% protection was observed for verine. To investigate bacterial loads in different tissues after infection, each mouse was infected with $2 \times 10^6$ CFU of *S. aureus* USA300. As bacteria were able to spread to various tissues 2 hours post-infection (Example 1), peptide treatment was initiated. The mice were euthanized 24 hours post peptide treatment. As a positive control, a significant CFU decrease (1-4 logs) was observed in spleen, lung, kidney, and liver when the infected mice were treated with vancomycin at 10 mg/kg per mouse. Remarkably, a similar CFU drop in these mouse tissues (2-4 logs) was observed when treated with horine intraperitoneally (FIG. 20). Moreover, intravenous injection of the same peptide into the infected BALB/c mice also showed 3-5 logs decrease in the *S. aureus* burden. These data established a systemic efficacy of horine (FIG. 20).

The in vivo efficacy of verine was also tested in a neutropenic mouse model infected with *K. pneumoniae* ($5 \times 10^5$ CFU per mouse). A dose-dependent antimicrobial effect was observed in different tissues of C57BL/6 mice following a single i.p. injection of 15 mg/kg per mouse (FIG. 21). Bacterial CFU was reduced by 2-4 logs in spleen, lung, kidney and liver (FIG. 20). In addition, verine also displayed outstanding efficacy (4-5 logs CFU drop in spleen, kidney, and liver of BALB/c mice) when administered via i.v. (FIG.

20). These results documented the systemic efficacy of verine in vivo against the nightmare pathogen.

The efficacy of the two peptides was also investigated in non-neutropenic mice against S. aureus USA300. A higher bacterial inoculum at $2\times10^8$ CFU per mouse was used. Again, CFU reduction was observed by 1-2.5 logs in spleen, lung, kidney, and liver (FIG. 22). These experiments further established the in vivo efficacy of both horine and verine. To evaluate the peptide pharmacokinetics (Chhonker, et al. (2018) Biomed. Chromatogr. e4389), the plasma clearance rate of horine after intravenous injection of 10 mg/kg into BALB/c mice was followed. Horine (266 ng/mL at 5 minutes) rapidly disappeared in mouse plasma and became undetectable within 1 hour. In contrast, horine made of D-amino acids could be detected at 192 µg/mL at 5 minutes and 0.17 µg/mL at 24 hours, supporting the observation that the D-form peptide is more stable.

Implanted medical devices can be infected with bacterial biofilms. Because such biofilms are resistant to conventional antibiotics, the last resort is to replace the implants, which add cost and cause inconvenience to patients. To address this challenging issue, the efficacy of horine and verine was also tested in a C57BL/6 mouse catheter-associated biofilm model (Thurlow, et al. (2011) J. Immunol., 186: 6585-6596; Wang, et al. (2014) ACS Chem. Biol., 9:1997-2002; Heim, et al. (2014) Methods Mol. Biol., 1106:183-191). In this model, the catheter lumen was infected with S. aureus USA300 followed by peptide treatment. At day 3 post treatment, the burdens of S. aureus USA300 in catheters and their surrounding tissues were eliminated (FIG. 23A, 23B). Therefore, these peptides can be used for topical treatment of implants to prevent biofilm formation.

The advantages of the instant peptides, however, are not limited to bacterial killing. They can also regulate the immune response against pathogens through the infiltration of major immune cells to the site of an infection via critical cytokine signaling (Marr, et al. (2006) Curr. Opin. Pharm., 6:468-472; Lai, et al. (2009) Trends Immunol., 30:131-141). The levels of cytokines in plasma of non-neutropenic mice were quantitated by ELISA kits (FIG. 24). In a non-neutropenic mouse model, TNF-α was reduced in all the cases, while MCP-1 increased. Also, IL-17A increased except for i.p. treated horine. When i.v. treated, there was a substantial increase in the level of IL-10 for both peptides. However, the IL-10 increase was significant when both peptides were i.p. treated. Thus, the peptide treatment mode showed a drastic impact on the level of IL-10, but not the levels of MCP-1 or IL-17A. When verine was i.p. treated, the higher level of IL-17A than IL-10 induced the recruitment of neutrophils to help clear the infection. This mechanism is not initiated in the case of horine when i.p. injected. For i.v. treatment, similar levels of IL-17A and IL-10 would prevent tissue damage from over inflammation (Miller, et al. (2011) Nat. Rev. Immunol., 11:505-518; Nell, et al. (2006) Peptides 27:649-660).

Immune regulation also occurs in the catheter case (FIG. 23). An increase in the level of MCP-1 (CCL2) would cause the recruitment of monocytes to infection sites (Thurlow, et al. (2011) J. Immunol., 186: 6585-6596; Wang, et al. (2014) ACS Chem. Biol., 9:1997-2002). In addition, there was an increase in the level of IL-17A, which infiltrates neutrophils to the infection sites as well (Miller, et al. (2011) Nat. Rev. Immunol., 11:505-518). For both horine and verine treated cases, the level of IL-10 was also altered to a level comparable to IL-17A (FIG. 23), avoiding tissue damage from extreme inflammation. Collectively, horine and verine killed S. aureus USA300 biofilms directly and recruited immune cells to help clear infection.

Peptide drugs attracted tremendous attention recently with five having been approved by the FDA in 2017 (Mustaimi, et al. (2018) Pharmaceuticals 11:42). The interest in antimicrobial peptides persists because of their potency in eliminating drug-resistant pathogens. Currently, the focus has been on topical treatment. This study documents two designer peptides with systemic efficacy when administered by the i.p. or i.v. route. It is remarkable that the same set of eight amino acids could be arranged into two unique sequences and amphipathic structures (FIG. 15). Although horine shares a classic amphipathic helical structure with numerous peptides in the APD database, it is among the shortest ones with merely two turns (FIG. 15C). In contrast, verine, with its hydrophilic and hydrophobic side chains segregated along the vertical axis, has a novel amphipathic structure resembling a cationic detergent. This is the first example for such a peptide with a determined 3D structure (FIG. 15E). These structures provide a molecular basis for their antimicrobial potency via membrane targeting. The two distinct structures may also explain the different activity spectra of horine and verine. Superior to conventional antibiotics, both peptides are potent in eliminating various drug-resistant pathogens, biofilms and persisters. While horine is effective against VRE and MRSA, verine kills Gram-negative pathogens, including the nightmare pathogen K. pneumoniae. Pharmacokinetic studies reveal that these peptides can be degraded in 1-2 hours, indicating the importance of rapid killing.

In addition, horine and verine are able to reshape the host immune response for pathogen clearance. In catheter-embedded mice, as well as non-neutropenic mice (i.v. treated), both peptides recruit immune cells to the infection sites. However, there is a subtle difference when the peptides are injected intraperitoneally. While horine mainly recruits monocytes, verine attracts both monocytes and neutrophils to clear MRSA infection. The basis for the anti-inflammatory effect of horine and verine may be due to contributions from several related mechanisms, including that of IL-10, which can suppress pathogen-induced TNF-α and re-establish a balance to IL-17A to protect tissues from damage (Nell, et al. (2006) Peptides 27:649-660). In the case of Gram-negative pathogens such as K. pneumoniae, the neutralization of lipopolysaccharides (LPS) by verine could also inhibit the TLR-4 mediated signaling pathway of the host.

In conclusion, horine and verine are two novel peptides with unique amino acids, distinct 3D structures and activity spectra. Theoretically, it is significant that the same eight amino acids can fold into two representative amphipathic models in complex with bacterial membranes, underscoring the fundamental role of the peptide structure in determining its biological activity. Practically, it is also significant because horine and verine are safe and demonstrated both systemic and topical efficacies in various mouse models. The anti-infective potency of these peptides can be attributed to multiple mechanisms, including direct pathogen killing and immune boosting to better fight the infection. Because these two peptides are ultra-short, they can be chemically synthesized cost effectively. Therefore, horine and verine are two new antibiotics to combat drug-resistant pathogens.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A linear peptide comprising the amino acid sequence RRRWWWWX (SEQ ID NO: 62), wherein X is leucine, valine, or alanine, and
wherein said peptide is less than 12 amino acids in length.

2. The peptide of claim 1, wherein said peptide comprises SEQ ID NO: 56.

3. The peptide of claim 1, wherein said peptide comprises at least one D-amino acid.

4. The peptide of claim 3, wherein all of the amino acids are D-amino acids.

5. The peptide of claim 1,
wherein said peptide comprises at least one modification at the C-terminus and/or N-terminus selected from the group consisting of amidation and acetylation.

6. A composition comprising the peptide of claim 1 and at least one pharmaceutically acceptable carrier.

7. The composition of claim 6, further comprising at least one antibiotic.

8. A method for inhibiting a microbial infection in a subject in need thereof, said method comprising administering to said subject the peptide of claim 1.

9. The method of claim 8, further comprising the administration of at least one additional antibiotic.

10. The method of claim 8, wherein said microbial infection is a staphylococcal infection.

11. The method of claim 8, wherein said microbial infection is a methicillin-resistant *Staphylococcus aureus* (MRSA) infection.

12. A medical device or implant comprising the peptide of claim 1 covalently attached to the surface of the medical device or implant.

13. The peptide of claim 1, wherein said peptide comprises SEQ ID NO: 57.

14. The peptide of claim 1, wherein said peptide is less than 10 amino acids in length.

15. The peptide of claim 1, wherein said peptide consists of SEQ ID NO: 57.

16. The composition of claim 6, further comprising a peptide comprising SEQ ID NO: 54.

17. The peptide of claim 1, wherein said peptide comprises SEQ ID NO: 58.

18. A peptide comprising the amino acid sequence RRRWWWWX (SEQ ID NO: 62), wherein X is leucine, valine, or alanine,
wherein said peptide is less than 12 amino acids in length, and
wherein said peptide comprises at least one modification at the C-terminus and/or N-terminus selected from the group consisting of amidation and acetylation.

19. The peptide of claim 18, wherein said peptide comprises SEQ ID NO: 56.

20. The peptide of claim 18, wherein said peptide comprises SEQ ID NO: 57.

21. The peptide of claim 18, wherein said peptide comprises SEQ ID NO: 58.

22. The peptide of claim 18, wherein said peptide consists of SEQ ID NO: 57.

23. The peptide of claim 18, wherein said peptide is less than 10 amino acids in length.

24. A composition comprising the peptide of claim 18 and at least one pharmaceutically acceptable carrier.

25. The composition of claim 24, further comprising at least one antibiotic.

26. The composition of claim 24, further comprising a peptide comprising SEQ ID NO: 54.

27. The peptide of claim 18, wherein said peptide comprises at least one D-amino acid.

28. The peptide of claim 27, wherein all of the amino acids are D-amino acids.

29. A method for inhibiting a microbial infection in a subject in need thereof, said method comprising administering to said subject the peptide of claim 18.

30. The method of claim 29, further comprising the administration of at least one additional antibiotic.

31. The method of claim 29, wherein said microbial infection is a staphylococcal infection.

32. The method of claim 29, wherein said microbial infection is a methicillin-resistant *Staphylococcus aureus* (MRSA) infection.

33. A medical device or implant comprising the peptide of claim 18 covalently attached to the surface of the medical device or implant.

* * * * *

```
                           SEQUENCE LISTING

<160> NUMBER OF SEQ ID NOS: 62

<210> SEQ ID NO 1
<211> LENGTH: 13
<212> TYPE: PRT
<213> ORGANISM: Artificial Sequence
<220> FEATURE:
<223> OTHER INFORMATION: peptide

<400> SEQUENCE: 1

Gly Leu Leu Ser Leu Leu Ser Leu Leu Gly Lys Leu Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: peptide

<400> SEQUENCE: 2

Gly Ala Leu Ser Leu Leu Ser Leu Leu Gly Lys Leu Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: peptide

<400> SEQUENCE: 3

Gly Leu Ala Ser Leu Leu Ser Leu Leu Gly Lys Leu Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: peptide

<400> SEQUENCE: 4

Gly Leu Leu Ser Ala Leu Ser Leu Leu Gly Lys Leu Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: peptide

<400> SEQUENCE: 5

Gly Leu Leu Ser Leu Ala Ser Leu Leu Gly Lys Leu Leu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: peptide
```

<400> SEQUENCE: 6

Gly Leu Leu Ser Leu Leu Ser Ala Leu Gly Lys Leu Leu
1               5                   10

<210> SEQ ID NO 7
<211> LENGTH: 13
<212> TYPE: PRT
<213> ORGANISM: Artificial Sequence
<220> FEATURE:
<223> OTHER INFORMATION: peptide

<400> SEQUENCE: 7

Gly Leu Leu Ser Leu Leu Ser Leu Ala Gly Lys Leu Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: peptide

<400> SEQUENCE: 8

Gly Leu Leu Ser Leu Leu Ser Leu Leu Gly Lys Ala Leu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: peptide

<400> SEQUENCE: 9

Gly Leu Leu Ser Leu Leu Ser Leu Leu Gly Lys Leu Ala
1               5                   10

<210> SEQ ID NO 10
<211> LENGTH: 13
<212> TYPE: PRT
<213> ORGANISM: Artificial Sequence
<220> FEATURE:
<223> OTHER INFORMATION: peptide

<400> SEQUENCE: 10

Gly Leu Leu Ser Ala Leu Lys Ala Leu Gly Lys Leu Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: 7
<223> OTHER INFORMATION: Xaa = ornithine

<400> SEQUENCE: 11

Gly Leu Leu Ser Ala Leu Xaa Ala Leu Gly Lys Leu Leu
1               5                   10

<210> SEQ ID NO 12
<211> LENGTH: 13
<212> TYPE: PRT

```
<213> ORGANISM: Artificial Sequence
<220> FEATURE:
<223> OTHER INFORMATION: peptide
<220> FEATURE:
<221> NAME/KEY: VARIANT
<222> LOCATION: 7, 11
<223> OTHER INFORMATION: Xaa = ornithine

<400> SEQUENCE: 12

Gly Leu Leu Ser Ala Leu Xaa Ala Leu Gly Xaa Leu Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: peptide

<400> SEQUENCE: 13

Gly Leu Leu Ser Ala Leu Lys Ala Ala Gly Lys Leu Leu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: peptide

<400> SEQUENCE: 14

Gly Ala Leu Ser Ala Leu Lys Ala Leu Gly Lys Leu Leu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide

<400> SEQUENCE: 15

Gly Leu Leu Ser Ala Leu Lys Ala Leu Gly Lys Ala Leu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: peptide

<400> SEQUENCE: 16

Gly Leu Leu Ser Ala Ala Lys Ala Ala Gly Lys Leu Leu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: peptide

<400> SEQUENCE: 17

Gly Ala Leu Ser Ala Leu Lys Ala Leu Gly Lys Ala Leu
1               5                   10
```

```
<210> SEQ ID NO 18
<211> LENGTH: 12
<212> TYPE: PRT
<213> ORGANISM: Artificial Sequence
<220> FEATURE:
<223> OTHER INFORMATION: peptide

<400> SEQUENCE: 18

Gly Leu Leu Ser Leu Ser Leu Leu Gly Lys Leu Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: peptide

<400> SEQUENCE: 19

Gly Leu Leu Ser Leu Ser Leu Gly Lys Leu Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: peptide

<400> SEQUENCE: 20

Gly Leu Leu Ser Ser Leu Gly Lys Leu Leu
1               5                   10

<210> SEQ ID NO 21
<211> LENGTH: 9
<212> TYPE: PRT
<213> ORGANISM: Artificial Sequence
<220> FEATURE:
<223> OTHER INFORMATION: peptide

<400> SEQUENCE: 21

Gly Leu Ser Ser Leu Gly Lys Leu Leu
1               5

<210> SEQ ID NO 22
<211> LENGTH: 13
<212> TYPE: PRT
<213> ORGANISM: Artificial Sequence
<220> FEATURE:
<223> OTHER INFORMATION: peptide

<400> SEQUENCE: 22

Gly Leu Ser Leu Leu Leu Ser Leu Leu Gly Lys Leu Leu
1               5                   10

<210> SEQ ID NO 23
<211> LENGTH: 13
<212> TYPE: PRT
<213> ORGANISM: Artificial Sequence
<220> FEATURE:
<223> OTHER INFORMATION: peptide

<400> SEQUENCE: 23

Gly Leu Ser Leu Leu Leu Ser Leu Gly Leu Lys Leu Leu
1               5                   10

<210> SEQ ID NO 24
```

```
<211> LENGTH: 13
<212> TYPE: PRT
<213> ORGANISM: Artificial Sequence
<220> FEATURE:
<223> OTHER INFORMATION: peptide

<400> SEQUENCE: 24

Gly Leu Ser Leu Leu Leu Ser Leu Leu Gly Lys Leu Leu
1               5                   10

<210> SEQ ID NO 25
<211> LENGTH: 13
<212> TYPE: PRT
<213> ORGANISM: Artificial Sequence
<220> FEATURE:
<223> OTHER INFORMATION: peptide

<400> SEQUENCE: 25

Gly Leu Leu Ser Ser Leu Leu Leu Gly Lys Leu Leu
1               5                   10

<210> SEQ ID NO 26
<211> LENGTH: 13
<212> TYPE: PRT
<213> ORGANISM: Artificial Sequence
<220> FEATURE:
<223> OTHER INFORMATION: peptide

<400> SEQUENCE: 26

Gly Lys Leu Leu Ser Leu Leu Ser Leu Gly Leu Leu
1               5                   10

<210> SEQ ID NO 27
<211> LENGTH: 13
<212> TYPE: PRT
<213> ORGANISM: Artificial Sequence
<220> FEATURE:
<223> OTHER INFORMATION: peptide

<400> SEQUENCE: 27

Gly Leu Leu Ser Leu Leu Ser Leu Gly Leu Lys Leu Leu
1               5                   10

<210> SEQ ID NO 28
<211> LENGTH: 13
<212> TYPE: PRT
<213> ORGANISM: Artificial Sequence
<220> FEATURE:
<223> OTHER INFORMATION: peptide

<400> SEQUENCE: 28

Leu Leu Gly Ser Leu Leu Ser Leu Gly Leu Lys Leu Leu
1               5                   10

<210> SEQ ID NO 29
<211> LENGTH: 13
<212> TYPE: PRT
<213> ORGANISM: Artificial Sequence
<220> FEATURE:
<223> OTHER INFORMATION: peptide

<400> SEQUENCE: 29

Lys Leu Ser Leu Leu Leu Ser Leu Gly Leu Lys Leu Leu
1               5                   10

<210> SEQ ID NO 30
<211> LENGTH: 13
```

```
<212> TYPE: PRT
<213> ORGANISM: Artificial Sequence
<220> FEATURE:
<223> OTHER INFORMATION: peptide

<400> SEQUENCE: 30

Gly Leu Lys Leu Leu Leu Ser Leu Gly Leu Lys Leu Leu
1               5                   10

<210> SEQ ID NO 31
<211> LENGTH: 13
<212> TYPE: PRT
<213> ORGANISM: Artificial Sequence
<220> FEATURE:
<223> OTHER INFORMATION: peptide

<400> SEQUENCE: 31

Gly Leu Ser Leu Leu Leu Lys Leu Gly Leu Lys Leu Leu
1               5                   10

<210> SEQ ID NO 32
<211> LENGTH: 13
<212> TYPE: PRT
<213> ORGANISM: Artificial Sequence
<220> FEATURE:
<223> OTHER INFORMATION: peptide

<400> SEQUENCE: 32

Gly Leu Ser Leu Leu Leu Ser Leu Lys Leu Lys Leu Leu
1               5                   10

<210> SEQ ID NO 33
<211> LENGTH: 13
<212> TYPE: PRT
<213> ORGANISM: Artificial Sequence
<220> FEATURE:
<223> OTHER INFORMATION: peptide

<400> SEQUENCE: 33

Gly Leu Lys Leu Leu Leu Lys Leu Gly Leu Lys Leu Leu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: peptide

<400> SEQUENCE: 34

Lys Leu Lys Leu Leu Leu Lys Leu Gly Leu Lys Leu Leu
1               5                   10

<210> SEQ ID NO 35
<211> LENGTH: 22
<212> TYPE: PRT
<213> ORGANISM: Artificial Sequence
<220> FEATURE:
<223> OTHER INFORMATION: peptide

<400> SEQUENCE: 35

Gly Ile Gly Lys Phe Leu Lys Lys Ala Lys Lys Phe Gly Lys Ala Phe
1               5                   10                  15

Val Lys Ile Leu Lys Lys
            20
```

```
<210> SEQ ID NO 36
<211> LENGTH: 16
<212> TYPE: PRT
<213> ORGANISM: Artificial Sequence
<220> FEATURE:
<223> OTHER INFORMATION: peptide

<400> SEQUENCE: 36

Ala Leu Trp Met Thr Leu Leu Lys Lys Val Leu Lys Ala Ala Ala Lys
1               5                   10                  15

<210> SEQ ID NO 37
<211> LENGTH: 25
<212> TYPE: PRT
<213> ORGANISM: Artificial Sequence
<220> FEATURE:
<223> OTHER INFORMATION: peptide

<400> SEQUENCE: 37

Asn Leu Val Ser Gly Leu Ile Glu Ala Arg Lys Tyr Leu Glu Gln Leu
1               5                   10                  15

His Arg Lys Leu Lys Asn Cys Lys Val
            20                  25

<210> SEQ ID NO 38
<211> LENGTH: 21
<212> TYPE: PRT
<213> ORGANISM: Artificial Sequence
<220> FEATURE:
<223> OTHER INFORMATION: peptide

<400> SEQUENCE: 38

Glu Asn Arg Glu Val Pro Pro Gly Phe Thr Ala Leu Ile Lys Thr Leu
1               5                   10                  15

Arg Lys Cys Ile Ile
            20

<210> SEQ ID NO 39
<211> LENGTH: 19
<212> TYPE: PRT
<213> ORGANISM: Artificial Sequence
<220> FEATURE:
<223> OTHER INFORMATION: peptide

<400> SEQUENCE: 39

Arg Pro Asp Lys Pro Arg Pro Tyr Leu Pro Arg Pro Arg Pro Pro Arg
1               5                   10                  15

Pro Val Arg

<210> SEQ ID NO 40
<211> LENGTH: 11
<212> TYPE: PRT
<213> ORGANISM: Artificial Sequence
<220> FEATURE:
<223> OTHER INFORMATION: peptide

<400> SEQUENCE: 40

Phe Ile Ser Gln Ile Ile Ser Thr Ala Arg Ile
1               5                   10

<210> SEQ ID NO 41
<211> LENGTH: 8
<212> TYPE: PRT
<213> ORGANISM: Artificial Sequence
<220> FEATURE:
<223> OTHER INFORMATION: peptide
```

```
<400> SEQUENCE: 41

Trp Trp Trp Leu Arg Lys Ile Trp
1               5

<210> SEQ ID NO 42
<211> LENGTH: 8
<212> TYPE: PRT
<213> ORGANISM: Artificial Sequence
<220> FEATURE:
<223> OTHER INFORMATION: peptide

<400> SEQUENCE: 42

Trp Trp Leu Arg Lys Ile Trp Trp
1               5

<210> SEQ ID NO 43
<211> LENGTH: 8
<212> TYPE: PRT
<213> ORGANISM: Artificial Sequence
<220> FEATURE:
<223> OTHER INFORMATION: peptide

<400> SEQUENCE: 43

Trp Leu Arg Lys Ile Trp Trp Trp
1               5

<210> SEQ ID NO 44
<211> LENGTH: 8
<212> TYPE: PRT
<213> ORGANISM: Artificial Sequence
<220> FEATURE:
<223> OTHER INFORMATION: peptide

<400> SEQUENCE: 44

Leu Arg Lys Ile Trp Trp Trp Trp
1               5

<210> SEQ ID NO 45
<211> LENGTH: 8
<212> TYPE: PRT
<213> ORGANISM: Artificial Sequence
<220> FEATURE:
<223> OTHER INFORMATION: peptide

<400> SEQUENCE: 45

Arg Lys Ile Trp Trp Trp Trp Leu
1               5

<210> SEQ ID NO 46
<211> LENGTH: 8
<212> TYPE: PRT
<213> ORGANISM: Artificial Sequence
<220> FEATURE:
<223> OTHER INFORMATION: peptide

<400> SEQUENCE: 46

Lys Ile Trp Trp Trp Trp Leu Arg
1               5

<210> SEQ ID NO 47
<211> LENGTH: 8
<212> TYPE: PRT
<213> ORGANISM: Artificial Sequence
<220> FEATURE:
<223> OTHER INFORMATION: peptide
```

```
<400> SEQUENCE: 47

Ile Trp Trp Trp Trp Leu Arg Lys
1               5

<210> SEQ ID NO 48
<211> LENGTH: 8
<212> TYPE: PRT
<213> ORGANISM: Artificial Sequence
<220> FEATURE:
<223> OTHER INFORMATION: peptide

<400> SEQUENCE: 48

Trp Trp Trp Trp Leu Arg Lys Ile
1               5

<210> SEQ ID NO 49
<211> LENGTH: 8
<212> TYPE: PRT
<213> ORGANISM: Artificial Sequence
<220> FEATURE:
<223> OTHER INFORMATION: peptide

<400> SEQUENCE: 49

Trp Trp Trp Leu Arg Arg Ile Trp
1               5

<210> SEQ ID NO 50
<211> LENGTH: 8
<212> TYPE: PRT
<213> ORGANISM: Artificial Sequence
<220> FEATURE:
<223> OTHER INFORMATION: peptide

<400> SEQUENCE: 50

Arg Trp Trp Leu Arg Arg Ile Trp
1               5

<210> SEQ ID NO 51
<211> LENGTH: 8
<212> TYPE: PRT
<213> ORGANISM: Artificial Sequence
<220> FEATURE:
<223> OTHER INFORMATION: peptide

<400> SEQUENCE: 51

Trp Arg Trp Leu Arg Arg Ile Trp
1               5

<210> SEQ ID NO 52
<211> LENGTH: 8
<212> TYPE: PRT
<213> ORGANISM: Artificial Sequence
<220> FEATURE:
<223> OTHER INFORMATION: peptide

<400> SEQUENCE: 52

Trp Trp Arg Leu Arg Arg Ile Trp
1               5

<210> SEQ ID NO 53
<211> LENGTH: 8
<212> TYPE: PRT
<213> ORGANISM: Artificial Sequence
<220> FEATURE:
<223> OTHER INFORMATION: peptide

<400> SEQUENCE: 53
```

Trp Trp Trp Arg Arg Ile Trp
1               5

<210> SEQ ID NO 54
<211> LENGTH: 8
<212> TYPE: PRT
<213> ORGANISM: Artificial Sequence
<220> FEATURE:
<223> OTHER INFORMATION: peptide

<400> SEQUENCE: 54

Trp Trp Trp Leu Arg Arg Arg Trp
1               5

<210> SEQ ID NO 55
<211> LENGTH: 8
<212> TYPE: PRT
<213> ORGANISM: Artificial Sequence
<220> FEATURE:
<223> OTHER INFORMATION: peptide

<400> SEQUENCE: 55

Trp Trp Trp Leu Arg Arg Ile Arg
1               5

<210> SEQ ID NO 56
<211> LENGTH: 8
<212> TYPE: PRT
<213> ORGANISM: Artificial Sequence
<220> FEATURE:
<223> OTHER INFORMATION: peptide

<400> SEQUENCE: 56

Arg Arg Arg Trp Trp Trp Trp Leu
1               5

<210> SEQ ID NO 57
<211> LENGTH: 8
<212> TYPE: PRT
<213> ORGANISM: Artificial Sequence
<220> FEATURE:
<223> OTHER INFORMATION: peptide

<400> SEQUENCE: 57

Arg Arg Arg Trp Trp Trp Trp Val
1               5

<210> SEQ ID NO 58
<211> LENGTH: 8
<212> TYPE: PRT
<213> ORGANISM: Artificial Sequence
<220> FEATURE:
<223> OTHER INFORMATION: peptide

<400> SEQUENCE: 58

Arg Arg Arg Trp Trp Trp Trp Ala
1               5

<210> SEQ ID NO 59
<211> LENGTH: 8
<212> TYPE: PRT
<213> ORGANISM: Artificial Sequence
<220> FEATURE:
<223> OTHER INFORMATION: peptide

<400> SEQUENCE: 59

```
Arg Arg Arg Arg Trp Trp Trp Leu
1               5

<210> SEQ ID NO 60
<211> LENGTH: 6
<212> TYPE: PRT
<213> ORGANISM: Artificial Sequence
<220> FEATURE:
<223> OTHER INFORMATION: peptide

<400> SEQUENCE: 60

Arg Arg Arg Trp Trp Trp
1               5

<210> SEQ ID NO 61
<211> LENGTH: 7
<212> TYPE: PRT
<213> ORGANISM: Artificial Sequence
<220> FEATURE:
<223> OTHER INFORMATION: peptide

<400> SEQUENCE: 61

Arg Arg Arg Trp Trp Trp Trp
1               5

<210> SEQ ID NO 62
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: 8
<223> OTHER INFORMATION: Xaa = any amino acid

<400> SEQUENCE: 62

Arg Arg Arg Trp Trp Trp Trp Xaa
1               5
```